United States Patent
Zeng

(10) Patent No.: US 11,155,636 B2
(45) Date of Patent: Oct. 26, 2021

(54) PRL3 ANTIBODY

(71) Applicant: Agency for Science, Technology and Research, Singapore (SG)

(72) Inventor: Qi Zeng, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 16/309,439

(22) PCT Filed: Jun. 14, 2017

(86) PCT No.: PCT/SG2017/050300
§ 371 (c)(1),
(2) Date: Dec. 12, 2018

(87) PCT Pub. No.: WO2017/217934
PCT Pub. Date: Dec. 21, 2017

(65) Prior Publication Data
US 2020/0181283 A1    Jun. 11, 2020

(30) Foreign Application Priority Data
Jun. 14, 2016   (SG) .............. 10201604834P

(51) Int. Cl.
| | | |
|---|---|---|
| *C07K 16/40* | (2006.01) | |
| *A61P 35/04* | (2006.01) | |
| *C07K 16/30* | (2006.01) | |
| *A61K 39/00* | (2006.01) | |

(52) U.S. Cl.
CPC .............. *C07K 16/40* (2013.01); *A61P 35/04* (2018.01); *C07K 16/3046* (2013.01); *A61K 2039/505* (2013.01); *A61K 2039/54* (2013.01); *C07K 2317/24* (2013.01); *C07K 2317/34* (2013.01); *C07K 2317/565* (2013.01)

(58) Field of Classification Search
CPC ............. C07K 16/40; C07K 16/3046; C07K 2317/24; C07K 2317/34; C07K 2317/565; C07K 2317/73; C07K 2317/92; A61P 35/04; A61P 35/00; A61K 2039/505; A61K 2039/54
See application file for complete search history.

(56) References Cited

U.S. PATENT DOCUMENTS

2005/0287644 A1    12/2005   Chiu et al.
2011/0206657 A1*   8/2011   Zeng ............... G01N 33/57496
                                                      424/130.1

FOREIGN PATENT DOCUMENTS

| WO | WO-2006/091326 A1 | 8/2006 |
| WO | WO-2008/136774 A1 | 11/2008 |
| WO | WO-2011/065923 A1 | 6/2011 |
| WO | WO-2015/119570 A1 | 8/2015 |

OTHER PUBLICATIONS

International Search Report for PCT/SG2017/050300, 8 pages (dated Aug. 23, 2017).
Ferrone, S., Hidden Immunotherapy Targets Challenge Dogma, Sci. Transl. Med., 3: 99ps38 1-3 (2011).
Guo, K. et al., Engineering the first chimeric antibody in targeting intracellular PRL-3 oncoprotein for cancer therapy in mice, Oncotarget, 3(2): 158-171 (2012).
Guo, K. et al., Monoclonal antibodies target intracellular PRL phosphatases to inhibit cancer metastases in mice, Cancer Biol. Ther., 7(5): 750-757 (2008).
Li, J. et al., Generation of PRL-3- and PRL-1-Specific Monoclonal Antibodies as Potential Diagnostic Markers for Cancer Metastases, Clin. Cancer. Res., 11(6): 2195-2204 (2005).
Thura, M. et al., PRL-3 zumab, a first-in-class humanized antibody for cancer therapy, JCI Insight, 1(9): e87607 1-15 (2016).
Weidle, U.H. et al., Intracellular Proteins Displayed on the Surface of Tumor Cells as Targets for Therapeutic Intervention with Antibody-related Agents, Cancer Genomics & Proteomics, 8: 49-64 (2011).
Weiner, L. M. et al., Antibody-Based Immunotherapy of Cancer, Cell, 148: 1081-1084 (2012).
Written Opinion for PCT/SG2017/050300, 9 pages (dated Aug. 23, 2017).

* cited by examiner

*Primary Examiner* — Brad Duffy
*Assistant Examiner* — Cheom-Gil Cheong
(74) *Attorney, Agent, or Firm* — Choate, Hall & Stewart LLP; Brian E. Reese; Michael L. Vetter

(57) ABSTRACT

The present invention relates to humanised antibodies that bind PRL3.

12 Claims, 39 Drawing Sheets

Specification includes a Sequence Listing.

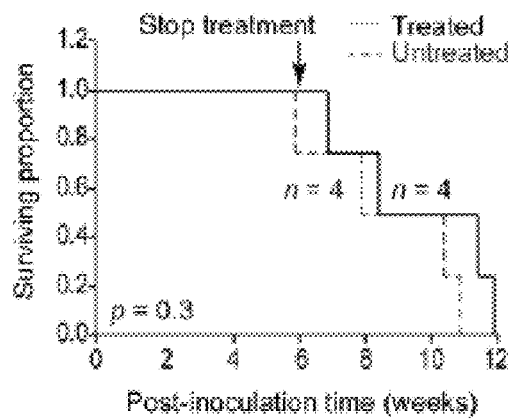
Figure 3C
| Cell line | PRL-3 status | Mean tumor volume ± SEM ($cm^3$) | | | | |
|---|---|---|---|---|---|---|
| | | Untreated | n | Treated | n | p-value |
| SNU-484 | PRL-3⁺ | 4.08 ± 0.54 | 8 | 0.23 ± 0.89 | 8 | 0.01 |
| NUGC-4 | PRL-3⁺ | 0.30 ± 0.1 | 4 | 0.02 ± 0.01 | 4 | 0.03 |
| IM-95 | PRL-3⁺ | 0.14 ± 0.03 | 6 | 0.01 ± 0.003 | 6 | 0.0008 |
| MKN45 | PRL-3⁻ | 0.19 ± 0.05 | 8 | 0.26 ± 0.08 | 8 | 0.45 |
| MKN45-PRL-3 | PRL-3⁺ | 0.39 ± 0.03 | 4 | 0.07 ± 0.02 | 5 | 0.00002 |
Figure 3D
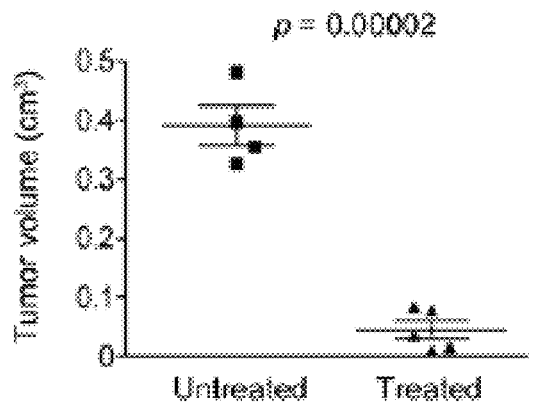
Figure 3E

|  |  |  | Mean values | | |
| --- | --- | --- | --- | --- | --- |
| Haematology | Ref. range | Unit | PRL3-zumab | PRL3-zumab + 5-FU | 5-FU alone |
| WBC count | 3.48 – 14.03 | × 10⁹/L | 4.83 | 1.10 | 0.60 |
| Neutrophils | 0.58 – 3.83 | × 10⁹/L | 1.65 | 0.04 | 0.03 |
| Lymphocytes | 2.22 – 9.83 | × 10⁹/L | 3.03 | 0.98 | 0.54 |
| Monocytes | 0.21 – 1.25 | × 10⁹/L | 0.16 | 0.03 | 0.03 |
| Eosinophils | 0.01 – 0.49 | × 10⁹/L | 0.00 | 0.02 | 0.00 |
| Basophils | 0.00 – 0.18 | × 10⁹/L | 0.01 | 0.04 | 0.01 |
| RBC count | 6.93 – 12.24 | × 10¹²/L | 6.97 | 5.07 | 4.87 |
| Haemoglobin | 12.6 – 20.5 | g/dL | 10.4 | 7.4 | 7.1 |
| MCV | 50.7 – 64.5 | fL | 58.3 | 49.3 | 47.7 |
| MCH | 13.2 – 17.6 | pg | 15.0 | 14.7 | 14.7 |
| MCHC | 23.3 – 32.7 | g/dL | 26.0 | 29.3 | 21.7 |
| Platelet | 420 – 1698 | × 10⁹/L | 1016 | 202 | 198 |

Figure 4C

>HZD_H1
QVQLVQSGAEVKKPGASVKVSCKASGYTFTNYYMHWVRQAPGQLEWMGWIYPGNVNTYYNEKFRGRVTIT
ADTSASTAYMLSSLRSEDTAVYYCASEEKNYPWFAYWGQGTLVTS     (SEQ ID NO: 16)

>HZD_H2
QVQLVQSGAEVKKPGASVKVSCKASGYTFTNYYMHWVRQAPGQLEWIGWIYPGNVNTYYNEKFRGRATLTA
DKSASTAYMLSSLRSEDTAVYYCASEEKNYPWFAYWGQGTLVTS     (SEQ ID NO: 17)

>HZD_H3
QVQLVQSGAEVKKPGASVKVSCKASGYTFTNYYMHWVRQAPGQLEWIGWIYPGNVNTYYNEKFRGRATITA
DTSASTAYMLSSLRSEDTAVYYCASEEKNYPWFAYWGQGTLVTS     (SEQ ID NO: 18)

>*HZD_H4*
QVQLVQSGAEVKKPGASVKVSCKASGYTFTNYYMHWVRQAPGQLEWIGWIYPGNVNTYYNEKFRGKATLTA
DKSASTAYMLSSLRSEDTAVYYCASEEKNYPWFAYWGQGTLVTS     (SEQ ID NO: 19)

>HZD_H5
QVQLVQSGAEVKKPGASVKVSCKASGYTFTNYYMHWVKQRPGQLEWIGWIYPGNVNTYYNEKFRGKATLTA
DKSASTAYMLSSLRSEDTAVYYCASEEKNYPWFAYWGQGTLVTS     (SEQ ID NO: 20)

>HZD_H6
QVQLVQSGAEVKKPGASVKVSCKASGYTFTNYYMHWVRQRPGQLEWIGWIYPGNVNTYYNEKFRGKATITA
DKSASTAYMLSSLRSEDTAVYYCASEEKNYPWFAYWGQGTLVTS     (SEQ ID NO: 21)

>HZD_H7
QVQLVQSGAEVKKPGASVKVSCKASGYTFTNYYMHWVRQAPGQGLEWIGWIYPGNVNTYYNEKFRGKATIT
ADTSASTAYMELSSLRSEDTAVYFCASEEKNYPWFAYWGQGTLVTS     (SEQ ID NO: 22)

>H1
QVQLVQSGAEVKKPGASVKVSCKAS<u>GYTFTNYYMH</u>WVRQRPGQGLEWIG<u>WIYPGNVNTYYNEKFRG</u>KATIT
ADKSASTAYMELSSLRSEDTAVYFCAS<u>EEKNYPWFAY</u>WGQGTLVTVSSAS     (SEQ ID NO: 23)

>H2
QVQLVQSGAEVKKPGASVKVSCKAS<u>GYTFTNYYMH</u>WVRQAPGQGLEWIG<u>WIYPGNVNTYYNEKFRG</u>KATIT
ADTSASTAYMELSSLRSEDTAVYFCAS<u>EEKNYPWFAY</u>WGQGTLVTVSSAS     (SEQ ID NO: 24)

>H3
QVQLVQSGAEVKKPGASVKVSCKAS<u>GYTFTNYYMH</u>WVRQAPGQGLEWIG<u>WIYPGNVNTYYNEKFRG</u>KATLT
ADKSASTAYMELSSLRSEDTAVYFCAS<u>EEKNYPWFAY</u>WGQGTLVTVSSAS     (SEQ ID NO: 25)

Heavy Chain
CDR1 GYTFTNYYMH (SEQ ID NO: 1)
CDR2 WIYPGNVNTYYNEKFRG (SEQ ID NO: 2)
CDR3 EEKNYPWFAY (SEQ ID NO: 3)

Figure 7A

Humanized light chain protein sequences

>HZD_K1
DTQLTQSPSSLSASVGDRVTICKASQSVEDDGENYMNWYQQKPGSPKLLIYAASNLESGIPARFSGSGSGTD
FTLTISSLPEDFATYYCQQSNEDPFTFGSGTKLEIK (SEQ ID NO: 7)

>HZD_K2
DTQLTQSPSSLSASVGDRVTICKASQSVEDDGENYMNWYQQKPGSPKLLIYAASNLESGIPARFSGSGSGTD
FTLTISSLPEDFATYYCQQSNEDPFTFGQGTKLEIK (SEQ ID NO: 8)

>HZD_K3
DTQLTQSPSSLSASVGDRVTICKASQSVEDDGENYMNWYQQKPGSPKLLIYAASNLESGVPSRFSGSGSGTD
FTLTISSLPEDFATYYCQQSNEDPFTFGQGTKLEIK (SEQ ID NO: 9)

>HZD_K4
DTQLTQSPSSLSASVGDRVTICKASQSVEDDGENYMNWYQQKPGSPKLLIYAASNLESGIPSRFSGSGSGTD
FTLTISSLPEDFATYYCQQSNEDPFTFGPGTKVDIK (SEQ ID NO: 10)

>HZD_K5
DTQLTQSPSSLSASVGDRVTICKASQSVEDDGENYMNWYQQKPGSPKLLIYAASNLESGIPSRFSGSGSGTD
FTLTISSLPEDFATYYCQQSNEDPFTFGPGTKVDIK (SEQ ID NO: 11)

>HZD_K6
DTVLTQSPSSLSASVGDRVTICKASQSVEDDGENYMNWYQQKPGSPKLLIYAASNLESGIPSRFSG
SGSGTDFTLTISSLPEDFATYYCQQSNEDPFTFGPGTKVDIK (SEQ ID NO: 12)

>K
DIQMTQSPSSLSASVGDRVTISCKASQSVEDDGENYMNWYQQKPGKSPKLLIYAASNLESGIPARF
SGSGSGTDFTLTISSLQPEDFATYYCQQSNEDPFTFGSGTKLEIKRT    (SEQ ID NO: 13)

>L1
DIQMTQSPSSLSASVGDRVTITCKASQSVEDDGENYMNWYQQKPGKAPKLLIYAASNLESGVPSRF
SGSGSGTDFTLTISSLQPEDFATYYCQQSNEDPFTFGPGTKVDIKRT    (SEQ ID NO: 14)

>L2
DTQLTQSPSSLSASVGDRVTITCKASQSVEDDGENYMNWYQQKPGKAPKLLIYAASNLESGIPSRF
SGSGSGTDFTLTISSLQPEDFATYYCQQSNEDPFTFGPGTKVDIKRT    (SEQ ID NO: 15)

Light Chain

CDR1 KASQSVEDDGENYMN (SEQ ID NO:4)

CDR2 AASNLES (SEQ ID NO:5)

CDR3 QQSNEDPFT (SEQ ID NO:6)

Figure 7B

*Antibody 223 sequences*

The amino acid sequence of the heavy chain of the variable region of monoclonal antibody 223:

EFMEWSWVILFLLSIIAGVHCQVQLQQSGPELVKPGASVRISCKASGYTFTSYYIHWVKQRPG
QGLEWIGWIYPGNVNTEYNEKFRGKATLTADKSSSTAYMQLSSLTSEDSAVYFCASEERNYPW
FAYWGQGTLVTVSAAKTTPPPVYPLVPGSLG (SEQ ID NO. 33)

The amino acid sequence of the light chain of the variable region of monoclonal antibody 223:

WEFMETDTLLLWLLLWVLLLWPGSTGDIVLTQSPASLAVSLGQRATISCKASQSVEDDGENYMNWY
QQKPGQSPKLLIYAASNLESGIPARFSGSGSGTDFTLNIHPVEEEDAATYYCQQSNEDPFTFGSGTKLEIKRADAAPTVSIFPPSSKLG
(SEQ ID NO. 34)

Figure 8A

*Antibody 318 sequences*

The amino acid sequence of the heavy chain of the variable region of monoclonal antibody 318 is as follows:
EFMEWSWVFLFLLSIIAGVHCQVQLQQSGPELVKPGASVRISCKASGYTFTNYYMHWVKQRPG
QGLEWIGWIYPGNVNTYYNEKFRARPH.LQTNPPAQPTCSSAA.PLRTLRSISVQVRRELPLV
CLLGPRDSGHCLCSQNDTPIRLSPGPWKLG (SEQ ID NO. 35)

The amino acid sequence of the light chain of the variable region of monoclonal antibody 318 is as follows:
LVDMESDTLLLWVLLLWVPGSTGDIVLTQSPASLAVSLGQRATISYRASKSVSTSGYSYMHWN
QQKPGQPPRLLIYLVSNLESGVPARFSGSGSGTDFTLNIHPVEEEDAATYYCQHIRELTRSEG
GPSWK(SEQ ID NO. 36)

Figure 8B

| 1 | marmnrpapv | evsykhmrfl | ithnptnatl | stfiedlkky | gattvvrvce | vtydktplek |
|---|---|---|---|---|---|---|
| 61 | dgitvvdwpf | ddgapppgkv | vedwlslvka | kfceapgscv | avhcvaglgr | apvlvalali |
| 121 | esgmkyedai | qfirqkrrga | inskqltyle | kyrpkqrlrf | kdphthktrc | cvm (SEQ ID NO. 37) |

Figure 9

Light Chain Alignments

```
HZD_K1    DTQLTQSPSSLSASVGDRVTI-CKASQSVEDDGENYMNWYQQKPG-SPKLLIYAASNLES (SEQ
ID NO. 40)
HZD_K2    DTQLTQSPSSLSASVGDRVTI-CKASQSVEDDGENYMNWYQQKPG-SPKLLIYAASNLES (SEQ
ID NO. 41)
HZD_K3    DTQLTQSPSSLSASVGDRVTI-CKASQSVEDDGENYMNWYQQKPG-SPKLLIYAASNLES (SEQ
ID NO. 42)
HZD_K4    DTQLTQSPSSLSASVGDRVTI-CKASQSVEDDGENYMNWYQQKPG-SPKLLIYAASNLES (SEQ
ID NO. 43)
HZD_K5    DTQLTQSPSSLSASVGDRVTI-CKASQSVEDDGENYMNWYQQKPG-SPKLLIYAASNLES (SEQ
ID NO. 44)
HZD_K6    DTVLTQSPSSLSASVGDRVTI-CKASQSVEDDGENYMNWYQQKPG-SPKLLIYAASNLES (SEQ
ID NO. 45)
K         DIQMTQSPSSLSASVGDRVTISCKASQSVEDDGENYMNWYQQKPGKSPKLLIYAASNLES (SEQ
ID NO. 46)
L1        DIQMTQSPSSLSASVGDRVTITCKASQSVEDDGENYMNWYQQKPGKAPKLLIYAASNLES (SEQ
ID NO. 47)
L2        DTQLTQSPSSLSASVGDRVTITCKASQSVEDDGENYMNWYQQKPGKAPKLLIYAASNLES (SEQ
ID NO. 48)

HZD_K1    GIPARFSGSGSGTDFTLTISSL-PEDFATYYCQQSNEDPFTFGSGTKLEIK--(SEQ ID NO.
49)
HZD_K2    GIPARFSGSGSGTDFTLTISSL-PEDFATYYCQQSNEDPFTFGQGTKLEIK--(SEQ ID NO.
50)
HZD_K3    GVPSRFSGSGSGTDFTLTISSL-PEDFATYYCQQSNEDPFTFGQGTKLEIK----(SEQ ID NO.
51)
HZD_K4    GIPSRFSGSGSGTDFTLTISSL-PEDFATYYCQQSNEDPFTFGPGTKVDIK----(SEQ ID NO.
52)
HZD_K5    GIPSRFSGSGSGTDFTLTISSL-PEDFATYYCQQSNEDPFTFGPGTKVDIK----(SEQ ID NO.
53)
HZD_K6    GIPSRFSGSGSGTDFTLTISSL-PEDFATYYCQQSNEDPFTFGPGTKVDIK----(SEQ ID NO.
54)
K         GIPARFSGSGSGTDFTLTISSLQPEDFATYYCQQSNEDPFTFGSGTKLEIKRT--(SEQ ID NO.
55)
L1        GVPSRFSGSGSGTDFTLTISSLQPEDFATYYCQQSNEDPFTFGPGTKVDIKRT--(SEQ ID NO.
56)
L2        GIPSRFSGSGSGTDFTLTISSLQPEDFATYYCQQSNEDPFTFGPGTKVDIKRT--(SEQ ID NO.
57)
```

Grey boxes indicate CDR regions

Important domain sequences:

QSPSSLSASVGDRVT (SEQ ID NO: 26)
KASQSVEDDGENYMNWYQQK (SEQ ID NO: 27)
SGSGSGTDFTLTISSLQPEDFATYYCQQSNEDPFT (SEQ ID NO: 28)

Figure 10A

Heavy Chain Alignments

```
HZD_H1      QVQLVQSGAEVKKPGASVKVSCKASGYTFTNYYMHWVRQAPGQ-LEWMGWIYPGNVNTYY--(SEQ
ID NO. 58)
HZD_H2      QVQLVQSGAEVKKPGASVKVSCKASGYTFTNYYMHWVRQAPGQ-LEWIGWIYPGNVNTYY--(SEQ
ID NO. 59)
HZD_H3      QVQLVQSGAEVKKPGASVKVSCKASGYTFTNYYMHWVRQAPGQ-LEWIGWIYPGNVNTYY--(SEQ
ID NO. 60)
HZD_H4      QVQLVQSGAEVKKPGASVKVSCKASGYTFTNYYMHWVRQAPGQ-LEWIGWIYPGNVNTYY--(SEQ
ID NO. 61)
HZD_H5      QVQLVQSGAEVKKPGASVKVSCKASGYTFTNYYMHWVKQRPGQ-LEWIGWIYPGNVNTYY--(SEQ
ID NO. 62)
HZD_H6      QVQLVQSGAEVKKPGASVKVSCKASGYTFTNYYMHWVRQRPGQ-LEWIGWIYPGNVNTYY--(SEQ
ID NO. 63)
HZD_H7      QVQLVQSGAEVKKPGASVKVSCKASGYTFTNYYMHWVRQAPGQGLEWIGWIYPGNVNTYY--(SEQ
ID NO. 64)
H1          QVQLVQSGAEVKKPGASVKVSCKASGYTFTNYYMHWVRQRPGQGLEWIGWIYPGNVNTYY--(SEQ
ID NO. 65)
H2          QVQLVQSGAEVKKPGASVKVSCKASGYTFTNYYMHWVRQAPGQGLEWIGWIYPGNVNTYY--(SEQ
ID NO. 66)
H3          QVQLVQSGAEVKKPGASVKVSCKASGYTFTNYYMHWVRQAPGQGLEWIGWIYPGNVNTYY--(SEQ
ID NO. 67)

HZD_H1      NEKFRGRVTITADTSASTAYM-LSSLRSEDTAVYYCASEEKNYPWFAYWGQGTLVTS-----(SEQ
ID NO. 68)
HZD_H2      NEKFRGRATLTADKSASTAYM-LSSLRSEDTAVYYCASEEKNYPWFAYWGQGTLVTS-----(SEQ
ID NO. 69)
HZD_H3      NEKFRGRATITADTSASTAYM-LSSLRSEDTAVYYCASEEKNYPWFAYWGQGTLVTS-----(SEQ
ID NO. 70)
HZD_H4      NEKFRGKATLTADKSASTAYM-LSSLRSEDTAVYYCASEEKNYPWFAYWGQGTLVTS-------
(SEQ ID NO. 71)
HZD_H5      NEKFRGKATLTADKSASTAYM-LSSLRSEDTAVYYCASEEKNYPWFAYWGQGTLVTS-------
(SEQ ID NO. 72)
HZD_H6      NEKFRGKATITADKSASTAYM-LSSLRSEDTAVYYCASEEKNYPWFAYWGQGTLVTS-------
(SEQ ID NO. 73)
HZD_H7      NEKFRGKATITADTSASTAYMELSSLRSEDTAVYFCASEEKNYPWFAYWGQGTLVTS-------
(SEQ ID NO. 74)
H1          NEKFRGKATITADKSASTAYMELSSLRSEDTAVYFCASEEKNYPWFAYWGQGTLVTVSSAS-----
(SEQ ID NO. 75)
H2          NEKFRGKATITADTSASTAYMELSSLRSEDTAVYFCASEEKNYPWFAYWGQGTLVTVSSAS-----
(SEQ ID NO. 76)
H3          NEKFRGKATLTADKSASTAYMELSSLRSEDTAVYFCASEEKNYPWFAYWGQGTLVTVSSAS-----
(SEQ ID NO. 77)
```

Heavy Chains

Grey boxes indicate CDR regions

Important domain sequences:

VQSGAEVKKPGASVKVSCKASGYTFTNYYMHWV    (SEQ ID NO: 29)
WIYPGNVNTYYNEKFR    (SEQ ID NO: 30)
ASTAYMELSSLRSE    (SEQ ID NO: 31)
ASEEKNYPWFAYWGQGTLVT    (SEQ ID NO: 32)

Figure 10B

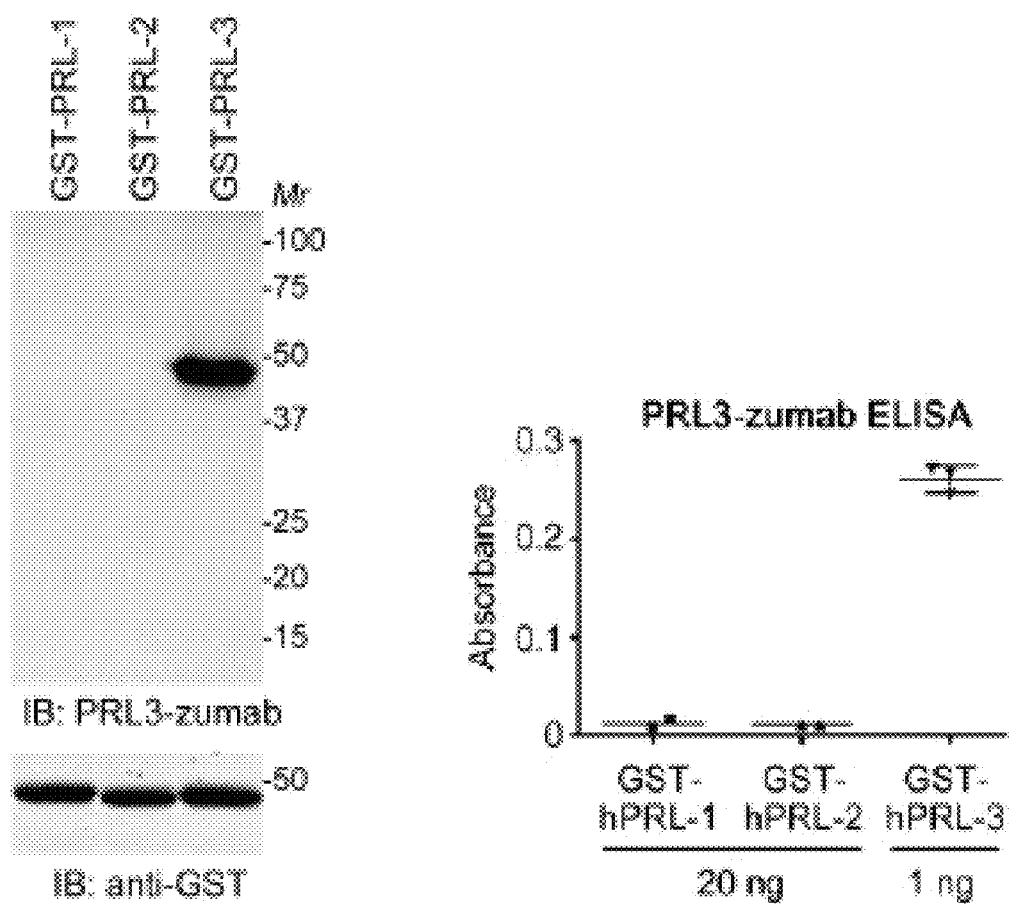
Figure 12A
Figure 12B
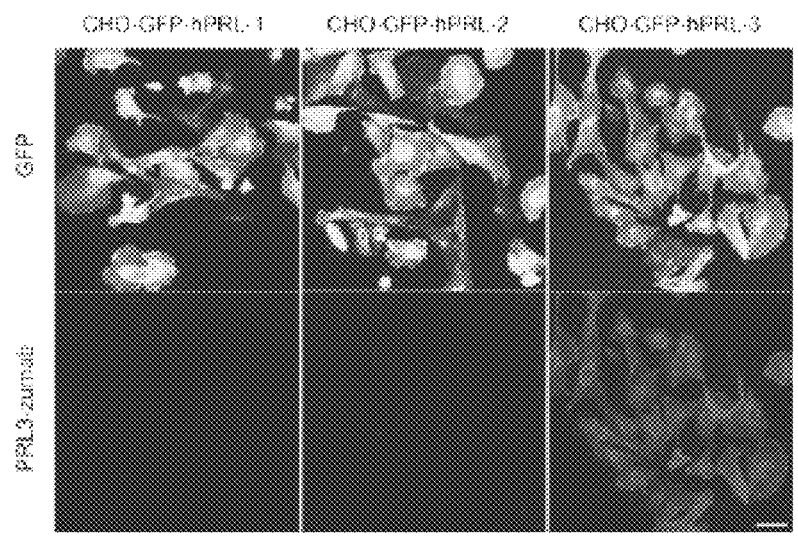
Figure 12C

Clinical characteristics of SGset1 GC patient cohort

|  | SGset1 (N = 185) |
|---|---|
| Age (years) | |
| range | 23.4 - 92.4 (1 missing) |
| mean ± S.D | 64 ± 12.9 (1 missing) |
| Gender (%) | |
| male | 68 (36.8) |
| female | 116 (62.7) |
| missing | 1 (0.54) |
| Stage (%) | |
| 1 | 29 (15.7) |
| 2 | 30 (16.2) |
| 3 | 66 (35.7) |
| 4 | 59 (31.8) |
| missing | 1 (0.54) |
| Lauren's histopathology (%) | |
| intestinal | 92 (49.7) |
| diffuse | 72 (38.9) |
| mixed/unclassifiable | 20 (10.8) |
| missing | 1 (0.54) |
| Helicobactor Pylori status (%) | |
| positive | 59 (31.9) |
| negative | 37 (20.0) |
| missing | 89 (48.1) |
| Median overall survival (months) | 22.5 (1 missing) |
| Number of overall death events | 110 (2 missing) |

Figure 17

Univariate and multivariate Cox regression analysis

|  | Category | HR (95% C.I.) | P-value |
|---|---|---|---|
| Univariate Cox (PRL-3 expression) | Med vs Low | 2.35 (1.42 - 3.87) | 0.0006 |
|  | High vs Low | 1.94 (1.17 - 3.21) | 0.01 |
| Multivariate Cox (PRL-3 expression, tumor stage) | Med vs Low | 1.99 (1.19 - 3.33) | 0.009 |
|  | High vs Low | 1.76 (1.76 - 2.95) | 0.03 |

Figure 18

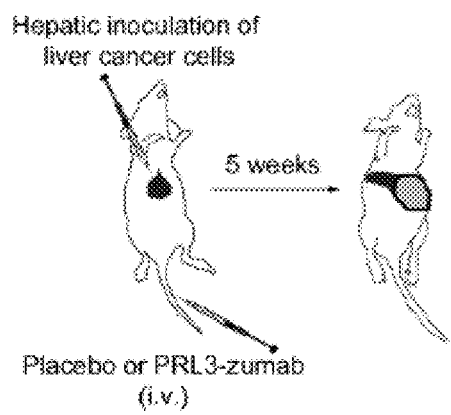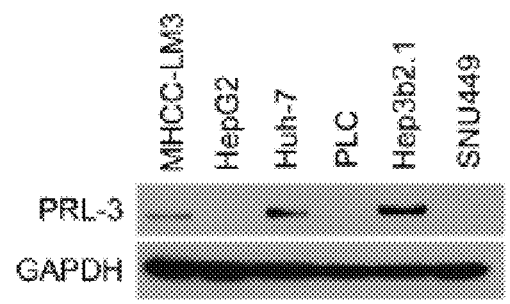
Figure 21A                Figure 21B
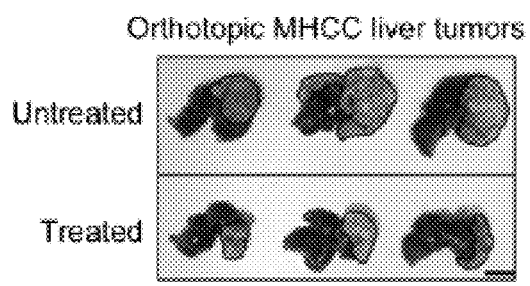
Figure 21C
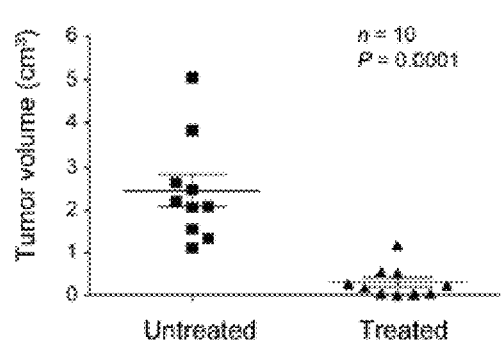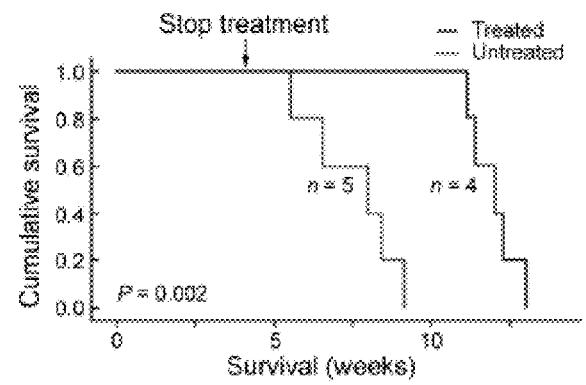
Figure 21D                Figure 21E

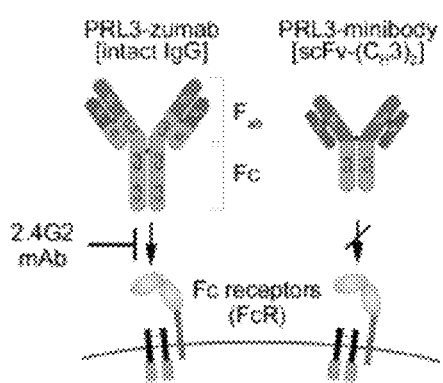
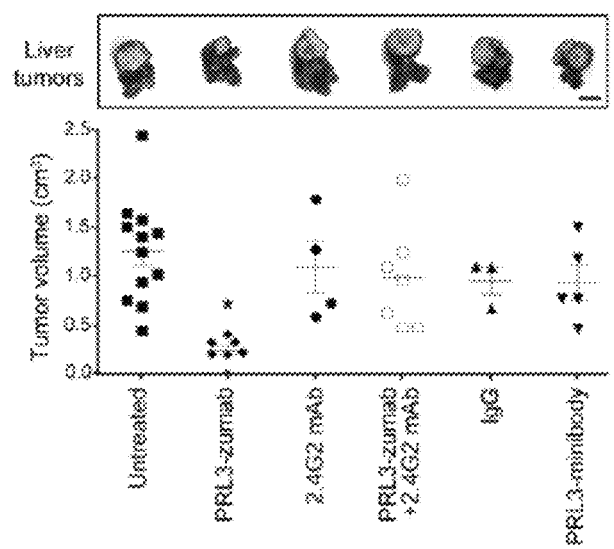
Figure 21F
Figure 21G

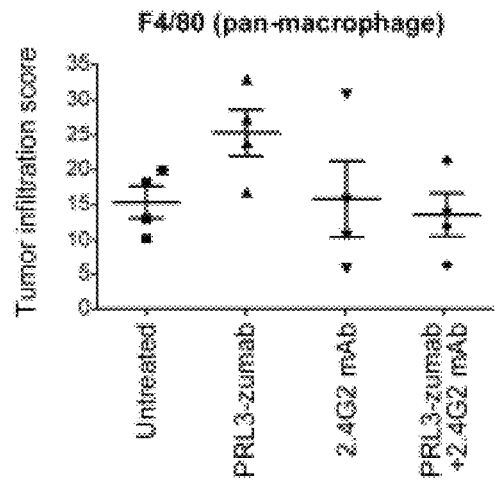
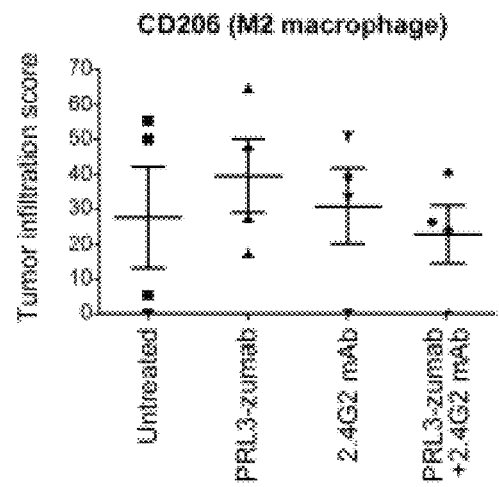
Figure 22A
Figure 22B
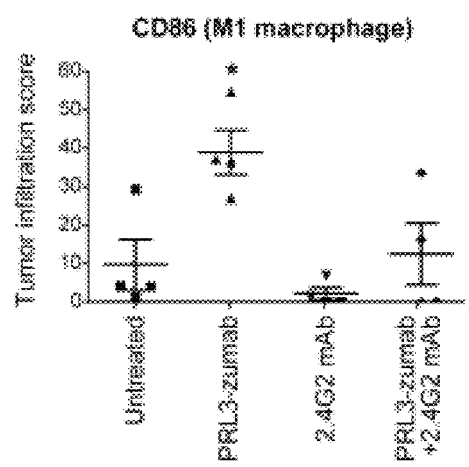
Figure 22C

PRL3 ANTIBODY

FIELD OF THE INVENTION

The present invention relates to humanised antibodies that bind PRL3.

SEQUENCE LISTING

The instant application contains a Sequence Listing which has been submitted electronically as .txt file named "2008187-0146_ST25.txt" The .txt file was created on Aug. 27, 2020 and is 55,041 bytes in size. The entire contents of the Sequence Listing are herein incorporated by reference.

BACKGROUND TO THE INVENTION

Cancer is fundamentally a disease of disordered gene expression leading to multistep progression towards metastasis (1), the major cause of cancer-related deaths (2). Accumulating evidence indicates that protein tyrosine phosphatases (PTPs) play important roles in driving metastatic progression (3). We identified phosphatase of regenerating liver-3 (PRL-3; also known as PTP4A3) in 1998 as a member of the PRL family of dual-specificity PTPs (4), which consists of three members: PRL-1, PRL-2, and PRL-3. In 2001, the Vogelstein group characterized PRL-3 as a metastasis-associated phosphatase specifically and highly upregulated in metastatic colorectal cancer samples, but not primary cancers and normal colorectal epithelia (5). PRL-3 was also identified as the most significant predictor of metastatic recurrence in patients with uveal melanoma in a recent independent global gene expression study (6). Clinically, elevated PRL-3 mRNA expression levels have been shown to correlate with higher metastatic potential and poor prognosis of multiple cancer types, including colorectal, gastric, breast, ovarian, and lung cancers (7).

PRLs are localized to the cytoplasmic face of the plasma membrane and endosomes via their prenylated C-termini (8). Mounting evidence suggests that PRL-3 promotes multiple stages of malignant transformation, including cellular proliferation, epithelial-mesenchymal transition (EMT), invasion, motility, angiogenesis, and survival (9). Molecularly, PRL-3 has been shown to activate the PI3K/Akt pathway indirectly through down-regulation of PTEN (10), and activate oncogenic ERK and SRC signaling via constitutive activation of multiple upstream receptor tyrosine kinases (11-13).

PRL-3 was first linked with GC progression in 2004 when it was found that higher PRL-3 levels correlated with increased GC invasiveness and metastasis (14). Since then, PRL-3 has been reported to be overexpressed in up to 70% of primary gastric carcinomas, with higher PRL-3 expression correlated to shorter post-operative survival at all tumor stages in GC patients (15,16). This prognostic potential of PRL-3 is particularly important as GC ranks as the third leading cause of cancer mortality worldwide with more than 700,000 gastric cancer-related deaths annually (2), largely due to delayed detection and the asymptomatic nature of the disease in its early stages, coupled to the high rate of recurrence after treatment (17). Despite high failure rates, radical surgery remains the standard form of therapy for GC, and adjuvant chemotherapy is often considered pre- and/or post-resection (18,19). Nonetheless, overall survival with chemotherapy remains poor and is accompanied with undesirable side effects due to non-specific targeting of other actively dividing, noncancerous cells (17). To this end, targeted therapy using tumor-specific biological agents has emerged as the focus of anti-cancer drug development due to their potential to selectively inhibit specific molecules involved in the growth and survival of cancer cells, whilst sparing normal cells. Current antibody therapies only target extracellular (cell-surface or secreted) proteins since antibodies are generally believed to be too large to enter cells, leaving a large pool of intracellular therapeutic targets, such as phosphatases, kinases, and transcription factors, untapped by antibody therapies. In GC, for example, the HER2/neu receptor antagonist trastuzumab (Herceptin) has been approved to target the 13-20% of GCs expressing cell-surface HER2/neu receptors, particularly metastatic gastric or gastroesophageal junction adenocarcinoma (20,21). However, despite moderate responses, patients often develop resistance to trastuzumab (22), hindering its efficacy. Alternative targeted therapies for GC are thus desperately needed and actively being sought after.

In 2008, we reported a novel approach of antibody therapy, targeting intracellular PRL-1 and PRL-3 oncoantigens (23). In that report, we showed that anti-PRL-3 antibodies inhibited experimental metastasis of cancer cells expressing PRL-3 (but not PRL-1) whilst anti-PRL-1 antibodies inhibited cancer cells expressing PRL-1 (but not PRL-3), thus establishing a stringent requirement for specific antibody-antigen recognition for therapeutic efficacy when targeting such intracellular oncoproteins. Following this, in 2011, we validated the feasibility and efficacy of this new concept, targeting additional endogenous and exogenous intracellular 'tumor-specific antigens' with antibody therapies or vaccinations in wild type C57BL/6 and transgenic spontaneous breast tumor MMTV-PyMT mice (24). We and Ferrone proposed three possible mechanisms for the antitumor activity of intracellular tumor antigen (TA)-specific antibodies, including antibody penetration into cells, antibody binding to externalized antigen and/or antibody recognition of MHC-bound antigen-derived peptides (25, 26).

Following the success of murine and, more recently, chimeric (27) anti-PRL-3 antibodies in targeting PRL-3-expressing tumors, we herein translate our approach into a more clinically-relevant setting with regards to four key aspects: 1) the use of PRL-3 humanized antibodies (PRL3-zumab) instead of mouse or chimeric antibodies; 2) targeting of human cancer cell lines instead of mouse cancer cell lines; 3) the development of more clinically-relevant orthotopic gastric tumor models instead of mouse tail vein metastatic models; and 4) the identification of a potential surrogate biomarker for monitoring of PRL3-zumab therapeutic efficacy. We demonstrate the first example of a new class of humanized antibody to block gastric tumorigenesis. Our findings reveal the potential of targeting intracellular oncoproteins with antibody therapy, ushering in a new era of cancer therapeutics.

SUMMARY OF THE INVENTION

Off-target effects are major clinical concerns for cancer therapies. We generated a first-in-class humanized antibody (PRL3-zumab) against tumor-specific intracellular PRL-3, an oncogenic phosphatase upregulated in multiple human cancers. We focused on gastric cancer (GC), providing independent evidence that elevated PRL-3 mRNA levels significantly correlate with shortened overall survival of GC patients. PRL-3 protein was overexpressed in 85% of fresh-frozen GC tumors, but not in patient-matched normal gastric tissues examined. Using human GC cell lines, we established clinically relevant orthotopic gastric tumor models and demonstrated that PRL3-zumab specifically blocked growth of PRL-3-positive (PRL-3+), but not PRL-3-negative (PRL-3−) tumors. PRL-3-zumab had better therapeutic efficacy as a monotherapy than in combination with 5-fluorouracil (5-FU), or 5-FU alone. PRL3-zumab was specifically enriched in PRL-3+ tumor tissues and promoted immune cell recruitment to PRL-3+ tumor microenvironments. Unexpectedly, we found secreted PRL-3 oncoprotein in 62% of multiple types of human cancer urines and in 100% of cancer urines derived from PRL-3+, but not PRL-3− tumor-bearing mice. Furthermore, urinary PRL-3 levels were significantly reduced after effective treatment with PRL3-zumab. The Urinary PRL-3 could be considered as a potential diagnostic and a surrogate biomarker for therapeutic response monitoring of PRL3-zumab therapy in multiple cancer types in future.

We also investigated the mechanism of action (MOA) to address how PRL-3 antibody could possibly bind to its intracellular PRL-3 antigen, and conclude that indeed 'Intracellular oncoprotein' can be re-localized to the cell surface as 'Extracellular oncoprotein' in cancer, thus follow a rational basis for tumor elimination via antibody conventional pathways against Extracellular Oncotargets.

Consistently, we found that PRL3-zumab blocks tumors expressing PRL-3 intracellular antigen, requiring host FcγII/III receptor interaction, full antibody activities, and increased M1 (but not M2) macrophages, B lymphocytes, natural killer cells to enhance host immunity. These results suggest the MOA of antibody targeting 'Intracellular oncoprotein' is indeed following the similar principles of targeting 'Extracellular Oncoprotein' via classical antibody-dependent cell cytotoxicity (ADCC) or phagocytotic (ADCP) pathways to eliminate tumors.

Finally, using 110 precious fresh-frozen human tumors or their matched normal tissues, we further showed that PRL-3 is an excellent tumor-specific oncotarget broadly overexpressed on an average ≥78% from 9 different human cancer types: liver, lung, colon, breast, stomach, bladder, prostate, AML, and kidney patient tumor samples, but not in matched normal tissues. PRL-3 may therefore be a useful biomarker of cancer, and a near-universal target for cancer therapy. PRL-3 may therefore provide a useful biomarker for solid cancers.

The present invention is concerned with antibodies, or antigen binding fragments, that bind to PRL3. Heavy and light chain polypeptides are also disclosed. The antibodies, antigen binding fragments and polypeptides may be provided in isolated and/or purified form and may be formulated into compositions suitable for use in research, therapy and diagnosis. In particular, the invention is concerned with humanized antibodies that bind PRL3, and in particular PRL3 antagonist antibodies.

In some cases, the antibodies of the invention inhibit a function of PRL3. In some cases, the antibodies inhibit a protein tyrosine phosphatase (PTP) function of PRL3. In some cases, the antibodies induce ADCC and/or ADCP. In some cases, the antibodies are capable of binding to Fc receptors, such as FcRII and/or FcRIII. In some cases, binding of the antibody to the cell leads to the recruitment of immune cells to the cell, such as B cells, NK cells, or macrophages, preferably M1 macrophages.

In one aspect of the present invention an antibody, or antigen binding fragment, is provided, the amino acid sequence of the antibody may comprise the amino acid sequences i) to iii), or the amino acid sequences iv) to vi), or preferably the amino acid sequences i) to vi):

| | | |
|---|---|---|
| i) | KASQSVEDDGENYMN | (SEQ ID NO:4) |
| ii) | AASNLES | (SEQ ID NO:5) |
| iii) | QQSNEDPFT | (SEQ ID NO:6) |
| iv) | GYTFTNYYMH | (SEQ ID NO:1) |
| v) | WIYPGNVNTYYNEKFRG | (SEQ ID NO:2) |
| vi) | EEKNYPWFAY | (SEQ ID NO:3) | or a variant thereof in which one or two or three amino acids in one or more of the sequences (i) to (vi) are replaced with another amino acid.

The antibody, or antigen binding fragment, may comprise at least one light chain variable region incorporating the following CDRs:

```
LC-CDR1: KASQSVEDDGENYMN       (SEQ ID NO:4)
LC-CDR2: AASNLES               (SEQ ID NO:5)
LC-CDR3: QQSNEDPFT             (SEQ ID NO:6)
```

The antibody, or antigen binding fragment, may comprise at least one heavy chain variable region incorporating the following CDRs:

```
HC-CDR1: GYTFTNYYMH            (SEQ ID NO: 1)
HC-CDR2: WIYPGNVNTYYNEKFRG     (SEQ ID NO: 2)
HC-CDR3: EEKNYPWFAY            (SEQ ID NO: 3)
```

The antibody may comprise at least one light chain variable region incorporating the CDRs shown in FIG. 7. The antibody may comprise at least one heavy chain variable region incorporating the CDRs shown in FIG. 7.

The antibody may comprise at least one light chain variable region ($V_L$) comprising the one of the amino acid sequences shown in FIG. 7 or an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to one of the amino acid sequences of the $V_L$ chain amino acid sequence shown in FIG. 7. The antibody may have a $V_L$ chain amino acid sequence having least 70%, more preferably one of at least 75%, 80%, 85%, 86%, 87%, 88%, 89%, 90%, 91%, 92%, 93%, 94%, 95%, 96%, 97%, 98%, 99%, or 100% sequence identity to one of the amino acid sequences shown in FIG. 7 and comprise the following CDR sequences:

```
LC-CDR1: KASQSVEDDGENYMN       (SEQ ID NO: 4)
```

LC-CDR2: AASNLES (SEQ ID NO: 5)

LC-CDR3: QQSNEDPFT (SEQ ID NO: 6)

The antibody may comprise at least one heavy chain variable region ($V_H$) comprising the one of the amino acid sequences shown in FIG. 7 or an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to one of amino acid sequences of the $V_H$ chain amino acid sequence shown in FIG. 7. The antibody may have a $V_H$ chain amino acid sequence having least 70%, more preferably one of at least 75%, 80%, 85%, 86%, 87%, 88%, 89%, 90%, 91%, 92%, 93%, 94%, 95%, 96%, 97%, 98%, 99%, or 100% sequence identity to one of the amino acid sequences shown in FIG. 7 and comprise the following CDR sequences:

HC-CDR1: GYTFTNYYMH (SEQ ID NO: 1)

HC-CDR2: WIYPGNVNTYYNEKFRG (SEQ ID NO: 2)

HC-CDR3: EEKNYPWFAY (SEQ ID NO: 3)

The antibody may comprise at least one light chain variable region comprising one of the amino acid sequences shown in FIG. 7 (or an amino acid sequence having at least 70%, more preferably one of at least 75%, 80%, 85%, 90%, 95%, 96%, 97%, 98%, 99% or 100%, sequence identity to one of the amino acid sequences of the $V_L$ chain amino acid sequence shown in FIG. 7) and at least one heavy chain variable region comprising one of the amino acid sequence shown in FIG. 7 (or an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to one of the amino acid sequences of the $V_H$ chain amino acid sequence shown in FIG. 7).

The antibody may bind PRL3. The antibody may optionally have amino acid sequence components as described above. The antibody may be an IgA, IgD, IgE, IgM or IgM, preferably an IgG. In one embodiment an in vitro complex, optionally isolated, comprising an antibody, or antigen binding fragment, as described herein, bound to PRL3 is provided.

In one aspect of the present invention an isolated heavy chain variable region polypeptide is provided, the heavy chain variable region polypeptide comprising the following CDRs:

HC-CDR1: GYTFTNYYMH (SEQ ID NO: 1)

HC-CDR2: WIYPGNVNTYYNEKFRG (SEQ ID NO: 2)

HC-CDR3: EEKNYPWFAY (SEQ ID NO: 3)

In one aspect of the present invention an antibody, or antigen binding fragment, is provided, the antibody, or antigen binding fragment, comprising a heavy chain and a light chain variable region sequence, wherein: the heavy chain comprises a HC-CDR1, HC-CDR2, HC-CDR3, having at least 85% overall sequence identity to HC-CDR1 sequence (SEQ ID NO:1), HC-CDR2 sequence (SEQ ID NO:2), HC-CDR3 sequence (SEQ ID NO:3), respectively, and the light chain comprises a LC-CDR1, LC-CDR2, LC-CDR3, having at least 85% overall sequence identity to LC-CDR1 sequence (SEQ ID NO:4), LC-CDR2 sequence (SEQ ID NO:5), LC-CDR3 sequence (SEQ ID NO:6), respectively.

In some embodiments the degree of sequence identity may be one of 86%, 87%, 88%, 89%, 90%, 91%, 92%, 93%, 94%, 95%, 96%, 97%, 98%, 99%, or 100%.

In another aspect of the present invention an antibody, or antigen binding fragment, optionally isolated, is provided comprising a heavy chain and a light chain variable region sequence, wherein:

the heavy chain sequence has at least 85% sequence identity to a heavy chain sequence set out in FIG. 7, and the light chain sequence has at least 85% sequence identity to a light chain sequence set out in FIG. 7

In some embodiments the degree of sequence identity may be one of 86%, 87%, 88%, 89%, 90%, 91%, 92%, 93%, 94%, 95%, 96%, 97%, 98%, 99%, or 100%.

In some embodiments the antibody, antigen binding fragment, or polypeptide further comprises variable region heavy chain framework sequences between the CDRs according to the arrangement HCFR1:HC-CDR1:HCFR2:HC-CDR2:HCFR3:HC-CDR3:HCFR4. The framework sequences may be derived from human consensus framework sequences.

In some cases, the antibody, antigen binding fragment, or polypeptide comprises a heavy chain sequence selected from:

VQSGAEVKKPGASVKVSCKASGYTFTNYYMHWV; (SEQ ID NO: 29)

WIYPGNVNTYYNEKFR; (SEQ ID NO: 30)

ASTAYMELSSLRSE; (SEQ ID NO: 31)

and/or

ASEEKNYPWFAYWGQGTLVT. (SEQ ID NO: 32)

In one aspect of the present invention an isolated light chain variable region polypeptide, optionally in combination with a heavy chain variable region polypeptide as described herein, is provided, the light chain variable region polypeptide comprising the following CDRs:

LC-CDR1: KASQSVEDDGENYMN (SEQ ID NO: 4)

LC-CDR2: AASNLES (SEQ ID NO: 5)

LC-CDR3: QQSNEDPFT (SEQ ID NO: 6)

In some embodiments the antibody, antigen binding fragment, or polypeptide further comprises variable region light chain framework sequences between the CDRs according to the arrangement LCFR1:LC-CDR1:LCFR2:LC-CDR2:LCFR3:LC-CDR3:LCFR4. The framework sequences may be derived from human consensus framework sequences.

In some cases, the antibody, antigen binding fragment, or polypeptide comprises a light chain sequence selected from:

```
                                    (SEQ ID NO: 26)
QSPSSLSASVGDRVT;

(SEQ ID NO: 27)
KASQSVEDDGENYMNWYQQK;
and/or (SEQ ID NO: 28)
SGSGSGTDFTLTISSLQPEDFATYYCQQSNEDPFT.
```

In some cases, the antibody, antigen binding fragment, or polypeptide comprises 2, 3, 4, 5, 6, or all of the amino acid sequences selected from:

```
                                    (SEQ ID NO: 29)
VQSGAEVKKPGASVKVSCKASGYTFTNYYMHWV;

(SEQ ID NO: 30)
WIYPGNVNTYYNEKFR;

(SEQ ID NO: 31)
ASTAYMELSSLRSE;

(SEQ ID NO: 32)
ASEEKNYPWFAYWGQGTLVT;

(SEQ ID NO: 26)
QSPSSLSASVGDRVT;

(SEQ ID NO: 27)
KASQSVEDDGENYMNWYQQK;
and/or (SEQ ID NO: 28)
SGSGSGTDFTLTISSLQPEDFATYYCQQSNEDPFT.
```

The antibody may comprise at least one light chain variable region ($V_L$) and/or a heavy chain variable region ($V_H$) comprising the one of the amino acid sequences shown in FIG. 7 or an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to one of the amino acid sequences shown in FIG. 7, and comprise the following CDR sequences:

```
                                    (SEQ ID NO: 4)
LC-CDR1: KASQSVEDDGENYMN (SEQ ID NO: 5)
LC-CDR2: AASNLES (SEQ ID NO: 6)
LC-CDR3: QQSNEDPFT (SEQ ID NO: 1)
HC-CDR1: GYTFTNYYMH (SEQ ID NO: 2)
HC-CDR2: WIYPGNVNTYYNEKFRG (SEQ ID NO: 3)
HC-CDR3: EEKNYPWFAY
``` and contain at least one of the following sequences:

```
                                    (SEQ ID NO: 29)
VQSGAEVKKPGASVKVSCKASGYTFTNYYMHWV;

(SEQ ID NO: 30)
WIYPGNVNTYYNEKFR;

(SEQ ID NO: 31)
ASTAYMELSSLRSE;

(SEQ ID NO: 32)
ASEEKNYPWFAYWGQGTLVT;

(SEQ ID NO: 26)
QSPSSLSASVGDRVT;

(SEQ ID NO: 27)
KASQSVEDDGENYMNWYQQK;
and/or (SEQ ID NO: 28)
SGSGSGTDFTLTISSLQPEDFATYYCQQSNEDPFT.
```

The antibody may comprise at least one light chain variable region ($V_L$) and/or a heavy chain variable region ($V_H$) comprising the one of the amino acid sequences shown in FIG. 7 or an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to one of the amino acid sequences shown in FIG. 7.

The antibody may comprise at least on light chain variable region ($V_H$) selected from: SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24 or SEQ ID NO: 25, or an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to amino acid sequence SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24 or SEQ ID NO: 25.

Preferably, the antibody comprises a light chain variable region ($V_H$) selected from: SEQ ID NO: 16, SEQ ID NO: 17, SEQ ID NO: 18, SEQ ID NO: 19, SEQ ID NO: 20, SEQ ID NO: 21 or SEQ ID NO: 22, or an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to amino acid sequence SEQ ID NO: 16, SEQ ID NO: 17, SEQ ID NO: 18, SEQ ID NO: 19, SEQ ID NO: 20, SEQ ID NO: 21 or SEQ ID NO: 22.

The antibody may comprise at least on light chain variable region ($V_L$) selected from: SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, or SEQ ID NO: 15, or an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to amino acid sequence SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, or SEQ ID NO: 15.

Preferably, the antibody comprises a light chain variable region ($V_L$) selected from: SEQ ID NO: 7, SEQ ID NO: 8, SEQ ID NO: 9, SEQ ID NO: 10, SEQ ID NO: 11 or SEQ ID NO: 12, or an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to amino acid sequence SEQ ID NO: 7, SEQ ID NO: 8, SEQ ID NO: 9, SEQ ID NO: 10, SEQ ID NO: 11 or SEQ ID NO: 12.

The antibody may comprise the following CDR sequences:

```
                                        (SEQ ID NO: 4)
    LC-CDR1: KASQSVEDDGENYMN (SEQ ID NO: 5)
    LC-CDR2: AASNLES (SEQ ID NO: 6)
    LC-CDR3: QQSNEDPFT (SEQ ID NO: 1)
    HC-CDR1: GYTFTNYYMH (SEQ ID NO: 2)
    HC-CDR2: WIYPGNVNTYYNEKFRG (SEQ ID NO: 3)
    HC-CDR3: EEKNYPWFAY
``` and contain at least one of the following sequences:

```
                                        (SEQ ID NO: 29)
    VQSGAEVKKPGASVKVSCKASGYTFTNYYMHWV;

(SEQ ID NO: 30)
    WIYPGNVNTYYNEKFR;

(SEQ ID NO: 31)
    ASTAYMELSSLRSE;

(SEQ ID NO: 32)
    ASEEKNYPWFAYWGQGTLVT;

(SEQ ID NO: 26)
    QSPSSLSASVGDRVT;

(SEQ ID NO: 27)
    KASQSVEDDGENYMNWYQQK;
    and/or (SEQ ID NO: 28)
    SGSGSGTDFTLTISSLQPEDFATYYCQQSNEDPFT.
``` and be capable of binding to PRL3, and antagonising a biological function of PRL3.

In some embodiments, the antibody, or antibody binding fragment, may further comprise a human constant region. For example selected from one of IgG1, IgG2, IgG3 and IgG4.

In some embodiments, the antibody, or antibody binding fragment, may further comprise a murine constant region. For example, selected from one of IgG1, IgG2A, IgG2B and IgG3.

The antibody is preferably a whole antibody, or an antibody or antibody fragment that includes an Fc domain. The antibody or antibody fragment may include one or both of a CH1 and a CH2 domain. Preferably, the antibody includes a CH2 domain. The antibody may contain both a CH1 and a CH2 domain. Preferably, the antibody is not a Fab', F(ab')$_2$ fragment, and/or is not an scFv and/or is not a minibody. Preferably, the antibody is an IgG immunoglobulin.

In some aspects, the individual to be treated is immunocompetent. The individual may have been determined to be immunocompetent. The individual may have been determined to produce NK cells, and/or B cells. The individual may be treated to stimulate the production and/or activation of NK cells and/or B cells, such as through the administration of cytokines, or by stopping the administration of agents known to reduce the production and/or activation of NK cells and/or B cells.

In another aspect of the present invention, a composition, e.g. a pharmaceutical composition or medicament, is provided. The composition may comprise an antibody, antigen binding fragment, or polypeptide as described herein and at least one pharmaceutically-acceptable carrier, excipient, adjuvant or diluent.

In another aspect of the present invention an isolated nucleic acid encoding an antibody, antigen binding fragment, or polypeptide as described herein is provided. The nucleic acid encode a sequence set out in FIG. 7, or a coding sequence which is degenerate as a result of the genetic code, or may have a nucleotide sequence having at least 70% identity thereto, optionally one of 75%, 80%, 85%, 86%, 87%, 88%, 89%, 90%, 91%, 92%, 93%, 94%, 95%, 96%, 97%, 98%, 99%, or 100%.

The antibody may bind to PRL3. The antibody may bind to an epitope comprising the amino acid sequence KAKFYN (SEQ ID NO. 38) and/or HTHKTR (SEQ ID NO. 39). The antibody may be capable of binding both sequences.

In one aspect of the present invention there is provided a vector comprising a nucleic acid described herein. In another aspect of the present invention, there is provided a host cell comprising the vector. For example, the host cell may be eukaryotic, or mammalian, e.g. Chinese Hamster Ovary (CHO), or human or may be a prokaryotic cell, e.g. *E. coli*.

In one aspect of the present invention a method for making an antibody, or antigen binding fragment or polypeptide as described herein is provided, the method comprising culturing a host cell as described herein under conditions suitable for the expression of a vector encoding the antibody, or antigen binding fragment or polypeptide, and recovering the antibody, or antigen binding fragment or polypeptide.

In another aspect of the present invention an antibody, antigen binding fragment or polypeptide is provided for use in therapy, or in a method of medical treatment. In another aspect of the present invention an antibody, antigen binding fragment or polypeptide as described herein is provided for use in the treatment of a T-cell dysfunctional disorder. In another aspect of the present invention, the use of an antibody, antigen binding fragment or polypeptide as described herein in the manufacture of a medicament or pharmaceutical composition for use in the treatment of a T-cell dysfunctional disorder is provided.

In another aspect of the present invention a method is provided, the method comprising contacting a sample containing, or suspected to contain, PRL3 with an antibody or antigen binding fragment, as described herein, and detecting the formation of a complex of antibody, or antigen binding fragment, and PRL3.

In another aspect of the present invention a method of diagnosing a disease or condition in a subject is provided, the method comprising contacting, in vitro, a sample from the subject with an antibody, or antigen binding fragment, as described herein, and detecting the formation of a complex of antibody, or antigen binding fragment, and PRL3.

In a further aspect of the present invention the use of an antibody, or antigen binding fragment, as described herein, for the detection of PRL3 in vitro is provided. In another aspect of the present invention the use of an antibody, or antigen binding fragment, as described herein, as an in vitro diagnostic agent is provided.

In methods of the present invention the antibody, antigen binding fragment or polypeptide may be provided as a composition as described herein.

In any aspect of the present invention the antibody preferably specifically binds PRL3 over other PRL phosphatases, such as PRL1 or PRL2.

The antibody may be an IgG. It may have a molecular weight of about 140 to 160 kDa, preferably about 150 kDa.

In some embodiments the antibody may be PRL3-ZUMAB.

Also disclosed herein is the use of a humanised antibody or antigen binding fragment as disclosed herein for the manufacture of a medicament for the treatment of cancer.

In other aspects, there is provided a humanised antibody or antibody binding fragment for use in a method of treating cancer. The antibody may be useful for inhibiting tumor formation, and/or inhibiting metastasis of tumor. The antibody may be useful for reducing the size of tumors. A treated individual may for example show a 1%, 2%, 3%, 4%, 5%, 6%, 7%, 8%, 9%, 10%, 15%, 20%, 25%, 30%, 40%, 50%, 60%, 70%, 80%, 90%, 100% or more decrease in tumour size of a particular tumour, or decrease in tumour number, or both, compared to an individual who has not been treated, or compared to that same individual prior to treatment.

Also provided are method of treating cancer comprising administering a humanised antibody or antibody binding fragment as disclosed herein.

The cancer may be a PRL3 expressing or overexpressing cancer. The cancer may be gastric cancer.

The humanised antibody or antibody binding fragment may be administered intravenously. It may be administered at a location distant to the cancer to be treated.

In some methods the patient has not previously received chemotherapy, particularly antimetabolite therapy, such as 5-FU. In some cases, the patient has not previously received such therapy before, or has not received such treatment for their cancer, such as for their gastric cancer. In some cases, the antibody is not co-administered with another agent (i.e. antibody monotherapy). In some cases, the antibody is not co-administered with 5-FU.

In some methods, the patient has been determined not to have an impaired immune system. In particular, the patient may have been determined to have a white blood cell count within normal range. In particular, the patient may have been determined to not have leukopenia. The patient may have been determined to have neturophil, lymphocyte, monocyte, red blood cell or platelet counts within normal range. The patient may have a white blood count, neturophil, lymphocyte, monocyte, red blood cell or platelet count that is not significantly different to a control, such as the count from an individual known to not have an impaired immune system, or to established normal values. For example, the patient may be determined to have between about 4,500 and about 10,000 white blood cells per microliter of blood.

In some aspects, the invention provides a method for selecting a patient for treatment with a humanised anti-PRL3 antibody or antibody fragment, the method comprising determining, in a sample of urine from the patient, the presence of PRL3. In some cases, the method involves determining the level of PRL3 in a urine sample from the patient. In some cases, the patient may have gastric, nasopharyngeal, bladder, lung, breast or prostate cancer.

In some cases, the individual has a family history of PRL3 overexpressing cancer, or has been identified as having a likelihood of developing a PRL3 overexpressing cancer. In some cases, the individual has a PRL3 overexpressing cancer, and is considered to be at risk of metastasis of that cancer.

In another aspect, provided herein are method involving determining the cellular localisation of PRL3. An increased proportion of cellular PRL3 on the cell surface may indicate that the individual has cancer. Provided herein is a method comprising determining the cellular localisation of PRL3 in a cell, wherein expression of PRL3 at the cell surface indicates that the cell is cancerous.

Methods include methods for the diagnosis of cancer, wherein the presence of, or an increase in PRL3 on the surface of a cell may indicate that the individual has cancer. In some cases, the amount of PRL3 in the cell is the same as a non-cancerous control sample, but the localisation of that PRL3 may be changed as compared to the non-cancerous control.

Other methods include a method for determining whether or not a cell is cancerous, the method comprising determining the presence of PRL3 at the surface of the cell. An increase in the level or proportion of PRL3 as compared to a control cell may indicate that the individual is, or will become, cancerous.

Methods may involve the selection of an individual for an anti-cancer therapy, based on the cellular localisation of PRL3 in the sample. In some cases, the methods involve administration of an anti-cancer therapy to an individual so selected.

In some cases, the method may comprise determining the cellular localisation of PRL3 in two or more samples from the patient, taken at two or more time points. A change in the amount of PRL3 on the surface of the cell may indicate an increase or decrease in the cancer in the individual. An increase in cell surface PRL3 over time may indicate that the individual has developed cancer, or the cancer has worsened. A decrease in cell surface PRL3 over time may indicate that the cancer has reduced, or that the therapy has resulted in treatment of the cancer. An increased or unchanged level of PRL3 at the cell surface may indicate that additional or alternative anti-cancer therapy is required. The level of PRL3 at the cell surface may therefore be used to select an individual for a further, or alternative, anti-cancer therapy.

An increase of 2-fold, 3-fold, 4-fold, 5-fold, 6-fold, 7-fold, 8-fold, 9-fold or 10-fold more PRL3 at the cell surface may indicate that the individual has cancer, and/or the cell is cancerous, or that the individual should be selected for treatment. The level of PRL3 at the cell surface may be compared to a control.

The sample may be a blood sample or a serum sample. The sample may be a urine sample. The cancer may be a sample of the tumor or of the tissue surrounding the tumor. The method may involve obtaining the sample, or the method may be performed on a sample previously obtained from the individual.

Methods of diagnosis and detection may be performed in vitro, or ex vivo, and in some cases do not involve the step of obtaining a sample from an individual.

DESCRIPTION

Antibodies

Antibodies according to the present invention preferably bind to PRL3 (the antigen), optionally with a Kd in the range 5 pM to 8 pM, preferably 6-7 pm, preferably about 6.3 pM. In some cases, the antibodies have an off rate of approximately $7 \times 10^{-5}$ s$^{-1}$. For example, between about $1 \times 10^{-5}$ s$^{-1}$ and $1 \times 10^{-6}$ s$^{-1}$.

In some embodiments, antibodies according to the present invention bind to PRL3, but not to PRL1 or PRL2.

Antibodies according to the present invention may be provided in isolated form.

By "antibody" we include a fragment or derivative thereof, or a synthetic antibody or synthetic antibody fragment.

In view of today's techniques in relation to monoclonal antibody technology, antibodies can be prepared to most antigens. The antigen-binding portion may be a part of an antibody (for example a Fab fragment) or a synthetic antibody fragment (for example a single chain Fv fragment [ScFv]). Suitable monoclonal antibodies to selected antigens may be prepared by known techniques, for example those disclosed in "Monoclonal Antibodies: A manual of techniques", H Zola (CRC Press, 1988) and in "Monoclonal Hybridoma Antibodies: Techniques and Applications", J G R Hurrell (CRC Press, 1982). Chimaeric antibodies are discussed by Neuberger et al (1988, 8th International Biotechnology Symposium Part 2, 792-799).

Monoclonal antibodies (mAbs) are useful in the methods of the invention and are a homogenous population of antibodies specifically targeting a single epitope on an antigen. Thus, mAbs binding PRL3 may be useful in the treatment of cancer.

Antigen binding fragments of antibodies, such as Fab and $Fab_2$ fragments may also be provided as can genetically engineered antibodies and antibody fragments. The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) Proc. Natl. Acad. Sd. USA 81, 6851-6855).

Antibodies and antibody binding fragments according to the invention have been humanised. Humanized antibodies are antibodies from non-human species whose protein sequences have been modified to increase their similarity to antibody variants produced naturally in humans. The process of "humanisation" is usually applied to monoclonal antibodies developed for administration to humans. The process of "humanisation" can be necessary when the process of developing a specific antibody involves generation in a non-human immune system, such as mice, as such antibodies may be immunogenic when administered to human patients. Humanisation may involve substitution of selective amino acids in the Fab portion of the molecule. Alternatively, humanisation may involve insertion of the appropriate CDR coding segments into a human antibody scaffold.

That antigenic specificity is conferred by variable domains and is independent of the constant domains is known from experiments involving the bacterial expression of antibody fragments, all containing one or more variable domains. These molecules include Fab-like molecules (Better et al (1988) Science 240, 1041); Fv molecules (Skerra et al (1988) Science 240, 1038); single-chain Fv (ScFv) molecules where the $V_H$ and $V_L$ partner domains are linked via a flexible oligopeptide (Bird et al (1988) Science 242, 423; Huston et al (1988) Proc. Natl. Acad. Sd. USA 85, 5879) and single domain antibodies (dAbs) comprising isolated V domains (Ward et al (1989) Nature 341, 544). A general review of the techniques involved in the synthesis of antibody fragments which retain their specific binding sites is to be found in Winter & Milstein (1991) Nature 349, 293-299.

By "ScFv molecules" we mean molecules wherein the $V_H$ and $V_L$ partner domains are covalently linked, e.g. by a flexible oligopeptide.

Fab, Fv, ScFv and dAb antibody fragments can all be expressed in and secreted from E. coli, thus allowing the facile production of large amounts of the said fragments.

Whole antibodies, and $F(ab)_2$ fragments are "bivalent". By "bivalent" we mean that the said antibodies and $F(ab')_2$ fragments have two antigen combining sites. In contrast, Fab, Fv, ScFv and dAb fragments are monovalent, having only one antigen combining site. Synthetic antibodies which bind to PRL3 may also be made using phage display technology as is well known in the art.

Antibodies may be produced by a process of affinity maturation in which a modified antibody is generated that has an improvement in the affinity of the antibody for antigen, compared to an unmodified parent antibody. Affinity-matured antibodies may be produced by procedures known in the art, e.g., Marks et al., Rio/Technology 10:779-783 (1992); Barbas et al. Proc Nat. Acad. Sci. USA 91:3809-3813 (1994); Schier et al. Gene 169:147-155 (1995); Yelton et al. J. Immunol. 155:1994-2004 (1995); Jackson et al., J. Immunol. 154(7):331 0-15 9 (1995); and Hawkins et al, J. Mol. Biol. 226:889-896 (1992).

Antibodies according to the present invention preferably exhibit specific binding to PRL3. An antibody that specifically binds to a target molecule preferably binds the target with greater affinity, and/or with greater duration than it binds to other targets. In one embodiment, the extent of binding of an antibody to an unrelated target is less than about 10% of the binding of the antibody to the target as measured, e.g., by a radioimmunoassay (RIA).

Antibodies according to the present invention preferably have a dissociation constant (Kd) of one of ≤1 µM, ≤100 nM, ≤1 nM or ≤100 pM. Binding affinity of an antibody for its target is often described in terms of its dissociation constant (Kd). Binding affinity can be measured by methods known in the art, such as by a radiolabeled antigen binding assay (RIA) performed with the Fab version of the antibody and antigen molecule.

Antibodies according to the present invention may be "antagonist" antibodies that inhibit or reduce a biological activity of the antigen to which it binds. Blocking of PRL3 may inhibit or reduce a phosphatase activity of PRL3. In some cases, the antibody binds to, but does not necessarily affect an activity of, PRL3.

In certain methods, the antibody is PRL3-ZUMAB, or a variant of PRL3-ZUMAB. PRL3-ZUMAB comprises the following CDR sequences:
Light chain:
LC-CDR1: (SEQ ID NO: 4)
LC-CDR2: (SEQ ID NO:5)
LC-CDR3: (SEQ ID NO:6)
Heavy chain:
HC-CDR1: (SEQ ID NO:1)
HC-CDR2: (SEQ ID NO:2)
HC-CDR3: (SEQ ID NO:3)
CDR sequences determined by Kabat definition.

The structure of an antibody molecule which has a CDR as described herein will generally be of a heavy or light chain sequence of an antibody molecule or substantial portion thereof in which the CDR is located at a location corresponding to the CDR of naturally occurring $V_H$ and $V_L$ antibody variable domains encoded by rearranged immunoglobulin genes. The structures and locations of immunoglobulin variable domains may be determined by reference to Kabat, E. A. et al, Sequences of Proteins of Immunological Interest. 4th Edition. US Department of Health and Human Services. 1987, and updates thereof. A number of academic and commercial on-line resources are available to query this database. For example, see Martin, A. C. R. Accessing the Kabat Antibody Sequence Database by Computer *PROTEINS: Structure, Function and Genetics*, 25 (1996), 130-133 and the associated on-line resource, currently at the world wide web address bioinf.org.uk/abs/simkab.html.

Antibodies according to the present invention may comprise the CDRs of PRL3-ZUMAB or one of SEQ ID NOs 1-6. In an antibody according to the present invention one or two or three or four of the six CDR sequences may vary. A variant may have one or two amino acid substitutions in one or two of the six CDR sequences.

Amino acid sequences of the $V_H$ and $V_L$ chains of ant-PRL3-ZUMAB clones are shown in FIG. 7.

The light and heavy chain CDRs may also be particularly useful in conjunction with a number of different framework regions. Accordingly, light and/or heavy chains having LC-CDR1-3 or HC-CDR1-3 may possess an alternative framework region. Suitable framework regions are well known in the art and are described for example in M. Lefranc & G. Lefranc (2001) "The Immunoglobulin FactsBook", Academic Press, incorporated herein by reference.

In this specification, antibodies may have $V_H$ and/or VL chains comprising an amino acid sequence that has a high percentage sequence identity to one or more of the $V_H$ and/or $V_L$ amino acid sequences of FIG. 7.

For example, antibodies according to the present invention include antibodies that bind PRL3 and have a $V_H$ chain that comprises an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to the $V_H$ chain amino acid sequence of one or the amino acid sequences shown in FIG. 7.

Antibodies according to the present invention may be detectably labelled or, at least, capable of detection. For example, the antibody may be labelled with a radioactive atom or a coloured molecule or a fluorescent molecule or a molecule which can be readily detected in any other way. Suitable detectable molecules include fluorescent proteins, luciferase, enzyme substrates, and radiolabels. The binding moiety may be directly labelled with a detectable label or it may be indirectly labelled. For example, the binding moiety may be an unlabeled antibody which can be detected by another antibody which is itself labelled. Alternatively, the second antibody may have bound to it biotin and binding of labelled streptavidin to the biotin is used to indirectly label the first antibody.

Although a variety of antibody fragments are described herein, the antibody is preferably a whole antibody, containing an antibody binding fragment (Fab), and a crystallisable fragment (Fc). The antibody may consist of two heavy chains and two light chains. It comprises a variable fragment (Fv), which provides the antigen specificity of the antibody, and a constant domain.

Antibody fragments according to the invention preferably include a CH2 domain. The CH2 domain of an antibody plays an important role in mediating effector functions and preserving antibody stability. Accordingly, the antibody fragments of the present invention are preferably not a Fab', F(ab)'$_2$, scFv or minibody.

Antibodies and fragments according to the invention are preferably able to interact with Fcγ (Fc-gamma) receptors, preferably FcγII (CD32) and FcγIII (CD16) receptors.

Methods of Detection

Antibodies, or antigen binding fragments, described herein may be used in methods that involve the binding of the antibody or antigen binding fragment to PRL3. Such methods may involve detection of the bound complex of antibody, or antigen binding fragment, and PRL3. As such, in one embodiment a method is provided, the method comprising contacting a sample containing, or suspected to contain, PRL3 with an antibody or antigen binding fragment as described herein and detecting the formation of a complex of antibody, or antigen binding fragment, and PRL3.

Suitable method formats are well known in the art, including immunoassays such as sandwich assays, e.g. ELISA. The method may involve labelling the antibody, or antigen binding fragment, or PRL3, or both, with a detectable label, e.g. fluorescent, luminescent or radio-label.

Methods of this kind may provide the basis of a method of diagnosis of a disease or condition requiring detection and or quantitation of PRL3. Such methods may be performed in vitro on a patient sample, or following processing of a patient sample. Once the sample is collected, the patient is not required to be present for the in vitro method of diagnosis to be performed and therefore the method may be one which is not practised on the human or animal body.

Such methods may involve determining the amount of PRL3 present in a patient sample. The method may further comprise comparing the determined amount against a standard or reference value as part of the process of reaching a diagnosis. Other diagnostic tests may be used in conjunction with those described here to enhance the accuracy of the diagnosis or prognosis or to confirm a result obtained by using the tests described here.

Detection in a sample of PRL3 may be used for the purpose of diagnosis a cancerous condition in the patient, diagnosis of a predisposition to a cancerous condition or for providing a prognosis (prognosticating) of a cancerous condition. The diagnosis or prognosis may relate to an existing (previously diagnosed) cancerous condition, which may be benign or malignant, may relate to a suspected cancerous condition or may relate to the screening for cancerous conditions in the patient (which may be previously undiagnosed).

A sample may be taken from any tissue or bodily fluid. The sample may comprise or may be derived from: a quantity of blood; a quantity of serum derived from the individual's blood which may comprise the fluid portion of the blood obtained after removal of the fibrin clot and blood cells; a tissue sample or biopsy; or cells isolated from said individual.

Methods according to the present invention are preferably performed in vitro. The term "in vitro" is intended to encompass experiments with cells in culture whereas the term "in vivo" is intended to encompass experiments with intact multi-cellular organisms.

Therapeutic Applications

Antibodies, antigen binding fragments and polypeptides according to the present invention and compositions comprising such agents may be provided for use in methods of medical treatment. Treatment may be provided to subjects having a disease or condition in need of treatment. The disease or condition may be cancer, including metastatic cancer.

Administration of an antibody, antigen binding fragment or polypeptide is preferably in a "therapeutically effective amount", this being sufficient to show benefit to the individual. The actual amount administered, and rate and timecourse of administration, will depend on the nature and severity of the disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

The methods and compositions described here suitably enable an improvement in a measurable criterion in an individual to whom the treatment is applied, compared to one who has not received the treatment.

For this purpose, a number of criteria may be designated, which reflect the progress of cancer or the well-being of the patient. Useful criteria may include tumour size, tumour dimension, largest dimension of tumour, tumour number, presence of tumour markers (such as alpha-feto protein), degree or number of metastates, etc.

Thus, as an example, a treated individual may show a decrease in tumour size or number as measured by an appropriate assay or test. A treated individual may for example show a 1%, 2%, 3%, 4%, 5%, 6%, 7%, 8%, 9%, 10%, 15%, 20%, 25%, 30%, 40%, 50%, 60%, 70%, 80%, 90%, 100% or more decrease in tumour size of a particular tumour, or decrease in tumour number, or both, compared to an individual who has not been treated.

The term proliferative disorder is used herein in a broad sense to include any disorder that requires control of the cell cycle. In particular, a proliferative disorder includes malignant and pre-neoplastic disorders. The methods and compositions described here are especially useful in relation to treatment or diagnosis of adenocarcinomas such as: small cell lung cancer, and cancer of the kidney, uterus, prostrate, bladder, ovary, colon and breast. For example, malignancies which may be treatable include acute and chronic leukemias, lymphomas, myelomas, sarcomas such as Fibrosarcoma, myxosarcoma, liposarcoma, lymphangioendotheliosarcoma, angiosarcoma, endotheliosarcoma, chondrosarcoma, osteogenic sarcoma, chordoma, lymphangiosarcoma, synovioma, mesothelioma, leimyosarcoma, rhabdomyosarcoma, colon carcinoma, ovarian cancer, prostate cancer, pancreatic cancer, breast cancer, squamous cell carcinoma, basal cell carcinoma, adenocarcinoma, sweat gland carcinoma, sebaceous 5 gland carcinoma, papillary carcinoma, papillary adenocarcinomas, cystadenocarcinoma, medullary carcinoma, bronchogenic carcinoma, choriocarcinoma, renal cell carcinoma, hepatoma, bile duct carcinoma seminoma, embryonal carcinoma, cervical cancer, testicular tumour, lung carcinoma, small cell lung carcinoma, bladder carcinoma, epithelial carcinoma, glioma, astrocytoma, ependymoma, pinealoma, 10 hemangioblastoma, acoustic neuoma, medulloblastoma, craniopharyngioma, oligodendroglioma, menangioma, melanoma, neutroblastoma and retinoblastoma.

For the purposes of this document, the term "cancer" can comprise any one or more of the following: acute lymphocytic leukemia (ALL), acute myeloid leukemia (AML), adrenocortical cancer, anal cancer, bladder cancer, blood cancer, bone cancer, brain tumor, breast cancer, cancer of the female genital system, cancer of the male genital system, central nervous system lymphoma, cervical cancer, childhood rhabdomyosarcoma, childhood sarcoma, chronic lymphocytic leukemia (CLL), chronic myeloid leukemia (CML), colon and rectal cancer, colon cancer, endometrial cancer, endometrial sarcoma, esophageal cancer, eye cancer, gallbladder cancer, gastric cancer, gastrointestinal tract cancer, hairy cell leukemia, head and neck cancer, hepatocellular cancer, Hodgkin's disease, hypopharyngeal cancer, Kaposi's sarcoma, kidney cancer, laryngeal cancer, leukemia, leukemia, liver cancer, lung cancer, malignant fibrous histiocytoma, malignant thymoma, melanoma, mesothelioma, multiple myeloma, myeloma, nasal cavity and paranasal sinus cancer, nasopharyngeal cancer, nervous system cancer, neuroblastoma, non-Hodgkin's lymphoma, oral cavity cancer, oropharyngeal cancer, osteosarcoma, ovarian cancer, pancreatic cancer, parathyroid cancer, penile cancer, pharyngeal cancer, pituitary tumor, plasma cell neoplasm, primary CNS lymphoma, prostate cancer, rectal cancer, respiratory system, retinoblastoma, salivary gland cancer, skin cancer, small intestine cancer, soft tissue sarcoma, stomach cancer, stomach cancer, testicular cancer, thyroid cancer, urinary system cancer, uterine sarcoma, vaginal cancer, vascular system, Waldenstrom's macroglobulinemia and Wilms' tumor.

The treatment may result in an alleviation of the symptoms of the cancer, or may result in the complete treatment of the cancer. The treatment may slow the progression of the cancer, or may prevent the worsening of the symptoms of the cancer.

Formulating Pharmaceutically Useful Compositions and Medicaments

Antibodies, antigen binding fragments and polypeptides according to the present invention may be formulated as pharmaceutical compositions for clinical use and may comprise a pharmaceutically acceptable carrier, diluent, excipient or adjuvant.

In accordance with the present invention methods are also provided for the production of pharmaceutically useful compositions, such methods of production may comprise one or more steps selected from: isolating an antibody, antigen binding fragment or polypeptide as described herein; and/or mixing an isolated antibody, antigen binding fragment or polypeptide as described herein with a pharmaceutically acceptable carrier, adjuvant, excipient or diluent.

For example, a further aspect of the present invention relates to a method of formulating or producing a medicament or pharmaceutical composition for use in the treatment of a T-cell dysfunctional disorder, the method comprising formulating a pharmaceutical composition or medicament by mixing an antibody, antigen binding fragment or polypeptide as described herein with a pharmaceutically acceptable carrier, adjuvant, excipient or diluent.

Cancer

A cancer may be any unwanted cell proliferation (or any disease manifesting itself by unwanted cell proliferation), neoplasm or tumor or increased risk of or predisposition to the unwanted cell proliferation, neoplasm or tumor. The cancer may be benign or malignant and may be primary or secondary (metastatic). A neoplasm or tumor may be any abnormal growth or proliferation of cells and may be located in any tissue. Examples of tissues include the adrenal gland, adrenal medulla, anus, appendix, bladder, blood, bone, bone marrow, brain, breast, cecum, central nervous system (including or excluding the brain) cerebellum, cervix, colon, duodenum, endometrium, epithelial cells (e.g. renal epithelia), gallbladder, oesophagus, glial cells, heart, ileum, jejunum, kidney, lacrimal glad, larynx, liver, lung, lymph, lymph node, lymphoblast, maxilla, mediastinum, mesentery, myometrium, nasopharynx, omentume, oral cavity, ovary, pancreas, parotid gland, peripheral nervous system, peritoneum, pleura, prostate, salivary gland, sigmoid colon, skin, small intestine, soft tissues, spleen, stomach, testis, thymus, thyroid gland, tongue, tonsil, trachea, uterus, vulva, white blood cells.

Tumors to be treated may be nervous or non-nervous system tumors. Nervous system tumors may originate either in the central or peripheral nervous system, e.g. glioma, medulloblastoma, meningioma, neurofibroma, ependymoma, Schwannoma, neurofibrosarcoma, astrocytoma and oligodendroglioma. Non-nervous system cancers/tumors may originate in any other non-nervous tissue, examples include melanoma, mesothelioma, lymphoma, myeloma, leukemia, Non-Hodgkin's lymphoma (NHL), Hodgkin's lymphoma, chronic myelogenous leukemia (CML), acute myeloid leukemia (AML), myelodysplastic syndrome (MDS), cutaneous T-cell lymphoma (CTCL), chronic lymphocytic leukemia (CLL), hepatoma, epidermoid carcinoma, prostate carcinoma, breast cancer, lung cancer, colon cancer, ovarian cancer, pancreatic cancer, thymic carcinoma, NSCLC, haematologic cancer and sarcoma.

In particularly preferred aspects, the cancer is a PRL3 expressing cancer. In some cases, the cancer is a PRL3 overexpressing cancer. That is, the cancer is associated with, or caused by, overexpression of PRL3. The PRL3 need not be functional in the cancer, but could instead be a label or artefact of the cancer cell. In particularly preferred aspects, the cancer is gastric cancer, nasopharyngeal cancer, bladder cancer, lung cancer, breast cancer or prostate cancer. The cancer may be acute myeloid leukemia, colon cancer or ovarian cancer. In some cases, the cancer is a metastatic cancer.

Simultaneous or Sequential Administration

Compositions may be administered alone or in combination with other treatments, either simultaneously or sequentially dependent upon the condition to be treated.

In this specification an antibody, antigen binding fragment or polypeptide of the present invention and an anti-infective agent or chemotherapeutic agent (therapeutic agent) may be administered simultaneously or sequentially.

In some embodiments, treatment with an antibody, antigen binding fragment or polypeptide of the present invention may be accompanied by chemotherapy.

Simultaneous administration refers to administration of the antibody, antigen binding fragment or polypeptide and therapeutic agent together, for example as a pharmaceutical composition containing both agents (combined preparation), or immediately after each other and optionally via the same route of administration, e.g. to the same artery, vein or other blood vessel.

Sequential administration refers to administration of one of the antibody, antigen binding fragment or polypeptide or therapeutic agent followed after a given time interval by separate administration of the other agent. It is not required that the two agents are administered by the same route, although this is the case in some embodiments. The time interval may be any time interval.

Chemotherapy

Chemotherapy refers to treatment of a cancer with a drug or with ionising radiation (e.g. radiotherapy using X-rays or γ-rays). In preferred embodiments chemotherapy refers to treatment with a drug. The drug may be a chemical entity, e.g. small molecule pharmaceutical, antibiotic, DNA intercalator, protein inhibitor (e.g. kinase inhibitor), or a biological agent, e.g. antibody, antibody fragment, nucleic acid or peptide aptamer, nucleic acid (e.g. DNA, RNA), peptide, polypeptide, or protein. The drug may be formulated as a pharmaceutical composition or medicament. The formulation may comprise one or more drugs (e.g. one or more active agents) together with one or more pharmaceutically acceptable diluents, excipients or carriers.

A treatment may involve administration of more than one drug. A drug may be administered alone or in combination with other treatments, either simultaneously or sequentially dependent upon the condition to be treated. For example, the chemotherapy may be a co-therapy involving administration of two drugs, one or more of which may be intended to treat the cancer.

The chemotherapy may be administered by one or more routes of administration, e.g. parenteral, intravenous injection, oral, or intratumoural.

The chemotherapy may be administered according to a treatment regime. The treatment regime may be a predetermined timetable, plan, scheme or schedule of chemotherapy administration which may be prepared by a physician or medical practitioner and may be tailored to suit the patient requiring treatment.

The treatment regime may indicate one or more of: the type of chemotherapy to administer to the patient; the dose of each drug or radiation; the time interval between administrations; the length of each treatment; the number and nature of any treatment holidays, if any etc. For a co-therapy a single treatment regime may be provided which indicates how each drug is to be administered.

Chemotherapeutic drugs may be selected from:
alkylating agents such as cisplatin, carboplatin, mechlorethamine, cyclophosphamide, chlorambucil, ifosfamide;
purine or pyrimidine anti-metabolites such as azathiopurine or mercaptopurine;
alkaloids and terpenoids, such as vinca alkaloids (e.g. vincristine, vinblastine, vinorelbine, vindesine), podophyllotoxin, etoposide, teniposide, taxanes such as paclitaxel (Taxol™), docetaxel;
topoisomerase inhibitors such as the type I topoisomerase inhibitors camptothecins irinotecan and topotecan, or the type II topoisomerase inhibitors amsacrine, etoposide, etoposide phosphate, teniposide;
antitumor antibiotics (e.g. anthracyline antibiotics) such as dactinomycin, doxorubicin (Adriamycin™), epirubicin, bleomycin, rapamycin;
antibody based agents, such as anti-TIM-3 antibodies, anti-VEGF, anti-TNFα, anti-IL-2, antiGpIIb/IIIa, anti-CD-52, anti-CD20, anti-RSV, anti-HER2/neu(erbB2), anti-TNF receptor, anti-EGFR antibodies, monoclonal antibodies or antibody fragments, examples include: cetuximab, panitumumab, infliximab, basiliximab, bevacizumab (Avastin®), abciximab, daclizumab, gemtuzumab, alemtuzumab, rituximab (Mabthera®), palivizumab, trastuzumab, etanercept, adalimumab, nimotuzumab
EGFR inhibitors such as erlotinib, cetuximab and gefitinib
anti-angiogenic agents such as bevacizumab (Avastin®
Further chemotherapeutic drugs may be selected from:
13-cis-Retinoic Acid, 2-Chlorodeoxyadenosine, 5-Azacitidine 5-Fluorouracil, 6-Mercaptopurine, 6-Thioguanine, Abraxane, Accutane®, Actinomycin-D Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Aranesp®, Aredia®, Arimidex®, Aromasin®, Arranon®, Arsenic Trioxide, Asparaginase, ATRA Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, Calcium Leucovorin, Campath®, Camptosar®, Camptothecin-11, Capecitabine, Carac™, Carboplatin, Carmustine, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine Cytosar-U®, Cytoxan®, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin, Diftitox, DepoCyt™, Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Eligard™, Ellence™, Eloxatin™, Elspar®, Emcyt®, Epirubicin, Epoetin Alfa, Erbitux, Erlotinib, Erwinia L-asparaginase, Estramustine, Ethyol Etopophos®, Etoposide, Etoposide Phosphate, Eulexin®, Everolimus, Evista®, Exemestane, Faslodex®, Femara®, Filgrastim, Floxuridine, Fludara®, Fludarabine, Fluoroplex®, Fluorouracil, Fluoxymesterone, Flutamide, Folinic Acid, FUDR®, Fulvestrant, Gefitinib, Gemcitabine, Gemtuzumab ozogamicin, Gleevec™, Gliadel® Wafer, Goserelin, Granulocyte-Colony Stimulating Factor, Granulocyte Macrophage Colony Stimulating Factor, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan, Idamycin®, Idarubicin, Ifex®, IFN-alpha, Ifosfamide, IL-11, IL-2, Imatinib mesylate, Imidazole Carboxamide, Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, Kidrolase, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilutamide, Nitrogen Mustard, Novaldex®, Novantrone®, Octreotide, Octreotide acetate, Oncospar®, Oncovin®, Ontak®, Onxal™, Oprevelkin, Orapred®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant Purinethol®, Raloxifene, Revlimid®, Rheumatrex®, Rituxan®, Rituximab, Roferon-A® (Interferon Alfa-2a), Rubex®, Rubidomycin hydrochloride, Sandostatin® Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, VP-16, Vumon®, Xeloda®, Zanosar®, Zevalin™, Zinecard®, Zoladex®, Zoledronic acid, Zolinza, Zometa®.

Routes of Administration

Antibodies, antigen binding fragments, polypeptides and other therapeutic agents, medicaments and pharmaceutical compositions according to aspects of the present invention may be formulated for administration by a number of routes, including but not limited to, parenteral, intravenous, intra-arterial, intramuscular, intratumoural and oral. Antibodies, antigen binding fragments, polypeptides and other therapeutic agents, may be formulated in fluid or solid form. Fluid formulations may be formulated for administration by injection to a selected region of the human or animal body.

In preferred aspects, the antibody is administered systemically. Intravenous administration is particularly contemplated.

In some cases, the antibody is applied at a location distant to cancerous cells, or distant to a known location of cancerous cells. In such cases, the antibodies may migrate within the body to the cancerous cells, such as migrating to a tumor.

In some aspects, the antibody is administered at the location of cancerous cells, such as applied directly to the tumor, or applied to a site of tumor resection. Administration may occur during resection surgery, or may occur after resection surgery. The tumor may be a primary cancer, or a metastatic cancer.

Administration may be performed with the intention of preventing a tumor regrowing at a site of tumor resection, or it may be performed with the intention of preventing cancerous cells forming at locations other than the resected tumor.

Dosage Regime

Multiple doses of the antibody, antigen binding fragment or polypeptide may be provided. One or more, or each, of the doses may be accompanied by simultaneous or sequential administration of another therapeutic agent.

Multiple doses may be separated by a predetermined time interval, which may be selected to be one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days, or 1, 2, 3, 4, 5, or 6 months. By way of example, doses may be given once every 7, 14, 21 or 28 days (plus or minus 3, 2, or 1 days).

Kits

In some aspects of the present invention a kit of parts is provided. In some embodiments the kit may have at least one container having a predetermined quantity of the antibody, antigen binding fragment or polypeptide. The kit may provide the antibody, antigen binding fragment or polypeptide in the form of a medicament or pharmaceutical composition, and may be provided together with instructions for administration to a patient in order to treat a specified disease or condition. The antibody, antigen binding fragment or polypeptide may be formulated so as to be suitable for injection or infusion to a tumor or to the blood.

In some embodiments the kit may further comprise at least one container having a predetermined quantity of another therapeutic agent (e.g. anti-infective agent or chemotherapy agent). In such embodiments, the kit may also comprise a second medicament or pharmaceutical composition such that the two medicaments or pharmaceutical compositions may be administered simultaneously or separately such that they provide a combined treatment for the specific disease or condition. The therapeutic agent may also be formulated so as to be suitable for injection or infusion to a tumor or to the blood.

Subjects

The subject to be treated may be any animal or human. The subject is preferably mammalian, more preferably human. The subject may be a non-human mammal, but is more preferably human. The subject may be male or female. The subject may be a patient. A subject may have been diagnosed with a disease or condition requiring treatment, or be suspected of having such a disease or condition.

Subject or Patient Selection

In some aspects, the patient has been selected for treatment with a humanised anti-PRL3 antibody or antibody fragment. In some cases, the patient has been determined to have a PRL3 expressing cancer. In some cases, the cancer is a PRL3 overexpressing cancer. In some cases, the patient is determined to have a functioning or active immune system, for example as indicated by the patient having a normal white blood cell count. In some methods, the patient has been determined not to have an impaired immune system. In particular, the patient may have been determined to have a white blood cell count within normal range. In particular, the patient may have been determined to not have leukopenia. The patient may have been determined to have neturophil, lymphocyte, monocyte, red blood cell or platelet counts within normal range. The patient may have a white blood count, neturophil, lymphocyte, monocyte, red blood cell or platelet count that is not significantly different to a control, such as the count from an individual known to not have an impaired immune system, or to established normal values. For example, the patient may be determined to have between about 4,500 and about 10,000 white blood cells per microliter of blood.

Some chemotherapeutic agents are associated with a decrease in white blood cell count, so in some cases, a patient is selected for treatment only if they have not received chemotherapy, or a particular chemotherapeutic agent in the past. In some cases, the patient has not received chemotherapeutic treatment for their cancer in the past. In some cases, the patient has not received antimetabolite chemotherapy. In some cases, the patient has not received thymidylate synthase inhibitor therapy. In some cases, the patient has not received 5-FU therapy.

The data provided herewith show that PRL3 found within the cells of a tumor or cancer may be present at adequate levels within the patient's urine to enable detection. Moreover, the inventors have found that PRL3 may be detected in urine at a very early stage in the development of the cancer. Thus, in some cases, the patient is selected for treatment based on detection or quantification of PRL3 in a sample of bodily fluid obtained from the patient, such as a sample of urine, saliva, blood or plasma, or any other bodily fluid, including breast milk. Preferably, the bodily fluid is urine. The presence or absence of the oncoprotein may involve an immunoassay, such as an ELISA or western blot based method. In some cases, PRL3 is detected in exosomes in the sample.

Cancers detectable by the methods disclosed herein include gastric cancer, bladder cancer, lung cancer, breast cancer, stomach cancer, nasopharyngeal cancer, prostate cancer (such as prostatic adenocarcinoma or prostatic hyperplasia, particularly being prostatic hyperplasia). The cancer may be distant from the source of the sample. The cancer may be one that is difficult and/or invasive to access for example to sample or biopsy. Thus, in one aspect disclosed herein, the patient may be diagnosed as having cancer through the detection of PRL3 in a sample of bodily fluid obtained from the patient, and then selected for treatment with humanised anti-PRL3 antibody. The cancer may be a solid cancer. As demonstrated herein, PRL3 is associated with a wide range of cancers.

As explained here, detection may involve determining the cellular localisation of PRL3, wherein an increase in cell surface PRL3 may indicate that the individual has cancer, or that the cell is cancerous.

Methods for the determination of the cellular localisation of PRL3 will be readily appreciated by those of skill in the art. In some cases, immunoassays are used to detect the target (e.g. PRL3) in a sample from the individual. Immunoassays use antibodies with specific affinity for the target molecule in conjunction with a detectable molecule. In some cases, the antibody is conjugated to the detectable molecule. The detectable molecule may be referred to as a label. The detectable molecule produces a detectable signal when the antibody is bound to the target molecule. The detectable signal may be a quantifiable signal. In some cases, an aptamer is used instead of, or together with, the antibody. Suitable methods include immunohistochemistry, such as in situ hybridization, fluorescence activated cell sorting (FACS) or flow cytometry. Methods may utilise a binding agent such as an antibody or aptamer that binds to PRL3, such as PRL3zumab. The methods may involve exposing the sample to the binding agent, such that cell surface PRL3 is bound by the binding agent, allowing detection of the binding agent.

Protein Expression

Molecular biology techniques suitable for the producing polypeptides according to the invention in cells are well known in the art, such as those set out in Sambrook et al., Molecular Cloning: A Laboratory Manual, New York: Cold Spring Harbor Press, 1989

The polypeptide may be expressed from a nucleotide sequence. The nucleotide sequence may be contained in a vector present in a cell, or may be incorporated into the genome of the cell.

A "vector" as used herein is an oligonucleotide molecule (DNA or RNA) used as a vehicle to transfer exogenous genetic material into a cell. The vector may be an expression vector for expression of the genetic material in the cell. Such vectors may include a promoter sequence operably linked to the nucleotide sequence encoding the gene sequence to be expressed. A vector may also include a termination codon and expression enhancers. Any suitable vectors, promoters, enhancers and termination codons known in the art may be used to express polypeptides from a vector according to the invention. Suitable vectors include plasmids, binary vectors, viral vectors and artificial chromosomes (e.g. yeast artificial chromosomes).

In this specification the term "operably linked" may include the situation where a selected nucleotide sequence and regulatory nucleotide sequence (e.g. promoter and/or enhancer) are covalently linked in such a way as to place the expression of the nucleotide sequence under the influence or control of the regulatory sequence (thereby forming an expression cassette). Thus a regulatory sequence is operably linked to the selected nucleotide sequence if the regulatory sequence is capable of effecting transcription of the nucleotide sequence. Where appropriate, the resulting transcript may then be translated into a desired protein or polypeptide.

Any cell suitable for the expression of polypeptides may be used for producing peptides according to the invention. The cell may be a prokaryote or eukaryote. Suitable prokaryotic cells include E. coli. Examples of eukaryotic cells include a yeast cell, a plant cell, insect cell or a mammalian cell. In some cases the cell is not a prokaryotic cell because some prokaryotic cells do not allow for the same post-translational modifications as eukaryotes. In addition, very high expression levels are possible in eukaryotes and proteins can be easier to purify from eukaryotes using appropriate tags. Specific plasmids may also be utilised which enhance secretion of the protein into the media.

Methods of producing a polypeptide of interest may involve culture or fermentation of a cell modified to express the polypeptide. The culture or fermentation may be performed in a bioreactor provided with an appropriate supply of nutrients, air/oxygen and/or growth factors. Secreted proteins can be collected by partitioning culture media/fermentation broth from the cells, extracting the protein content, and separating individual proteins to isolate secreted polypeptide. Culture, fermentation and separation techniques are well known to those of skill in the art.

Bioreactors include one or more vessels in which cells may be cultured. Culture in the bioreactor may occur continuously, with a continuous flow of reactants into, and a continuous flow of cultured cells from, the reactor. Alternatively, the culture may occur in batches. The bioreactor monitors and controls environmental conditions such as pH, oxygen, flow rates into and out of, and agitation within the vessel such that optimum conditions are provided for the cells being cultured.

Following culture of cells that express the polypeptide of interest, that polypeptide is preferably isolated. Any suitable method for separating polypeptides/proteins from cell culture known in the art may be used. In order to isolate a polypeptide/protein of interest from a culture, it may be necessary to first separate the cultured cells from media containing the polypeptide/protein of interest. If the polypeptide/protein of interest is secreted from the cells, the cells may be separated from the culture media that contains the secreted polypeptide/protein by centrifugation. If the polypeptide/protein of interest collects within the cell, it will be necessary to disrupt the cells prior to centrifugation, for example using sonification, rapid freeze-thaw or osmotic lysis. Centrifugation will produce a pellet containing the cultured cells, or cell debris of the cultured cells, and a supernatant containing culture medium and the polypeptide/protein of interest.

It may then be desirable to isolate the polypeptide/protein of interest from the supernatant or culture medium, which may contain other protein and non-protein components. A common approach to separating polypeptide/protein components from a supernatant or culture medium is by precipitation. Polypeptides/proteins of different solubilities are precipitated at different concentrations of precipitating agent such as ammonium sulfate. For example, at low concentrations of precipitating agent, water soluble proteins are extracted. Thus, by adding increasing concentrations of precipitating agent, proteins of different solubilities may be distinguished. Dialysis may be subsequently used to remove ammonium sulfate from the separated proteins.

Other methods for distinguishing different polypeptides/proteins are known in the art, for example ion exchange chromatography and size chromatography. These may be used as an alternative to precipitation, or may be performed subsequently to precipitation.

Once the polypeptide/protein of interest has been isolated from culture it may be necessary to concentrate the protein. A number of methods for concentrating a protein of interest are known in the art, such as ultrafiltration or lyophilisation.

Medicaments and pharmaceutical compositions according to aspects of the present invention may be formulated for administration by a number of routes, including but not limited to, parenteral, intravenous, intra-arterial, intramuscular, intratumoural, oral and nasal. The medicaments and compositions may be formulated for injection.

Administration is preferably in a "therapeutically effective amount", this being sufficient to show benefit to the individual. The actual amount administered, and rate and time-course of administration, will depend on the nature and severity of the disease being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Sequence Identity

Alignment for purposes of determining percent amino acid or nucleotide sequence identity can be achieved in various ways known to a person of skill in the art, for instance, using publicly available computer software such as ClustalW 1.82, T-coffee or Megalign (DNASTAR) software. When using such software, the default parameters, e.g. for gap penalty and extension penalty, are preferably used. The default parameters of ClustalW 1.82 are: Protein Gap Open Penalty=10.0, Protein Gap Extension Penalty=0.2, Protein matrix=Gonnet, Protein/DNA ENDGAP=−1, Protein/DNA GAPDIST=4.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Controls

In some cases, the method involves comparing cellular localisation of oncoprotein in a sample from an individual to one or more control samples.

The comparison may not require the analysis of the control sample to be simultaneously or sequentially performed with the analysis of the sample from the individual. Instead, the comparison may be made with results previously obtained from a control sample, such as results stored in a database.

The control sample may be a sample obtained from the individual prior to the onset of cancer, or prior to the observation of symptoms associated with cancer, or prior to the administration of anti-cancer therapy.

The control sample may be a sample obtained from another individual, such as an individual who does not have cancer. The individual may be matched to the individual according to one or more characteristics, for example, sex, age, medical history, ethnicity, weight or expression of a particular marker. The control sample may have been obtained from the bodily location, or be of the same tissue or sample type as the sample obtained from the individual.

The control sample may be a collection of samples, thereby providing a representative value across a number of different individuals or tissues.

In some cases, the control may be a reference sample or reference dataset. The reference may be a sample that has been previously obtained from a subject with a known degree of suitability for a particular treatment. The reference may be a dataset obtained from analyzing a reference sample.

Controls may be positive controls in which the target molecule is known to be present, or expressed at high level, or negative controls in which the target molecule is known to be absent or expressed at low level.

Controls may be samples of tissue that are from subjects who are known to benefit from the treatment. The tissue may be of the same type as the sample being tested. For example, a sample of tumor tissue from a subject may be compared to a control sample of tumor tissue from a subject who is known to be suitable for the treatment, such as a subject who has previously responded to the treatment.

In some cases the control may be a sample obtained from the same individual as the test sample, but from a time when the subject known to be healthy, such as a time when the subject was known to be free from cancer. Thus, a sample of cancerous tissue from a subject may be compared to a non-cancerous tissue sample.

In some cases, the control is a cell culture sample.

BRIEF DESCRIPTION OF THE FIGURES

Embodiments and experiments illustrating the principles of the invention will now be discussed with reference to the accompanying figures in which:

FIG. 7. Humanised Antibody Sequences showing location of CDRs. (A) Heavy chain sequences (B) Light chain sequences.

FIG. 8. Sequences for murine antibody clones (A) clone #223 and (B) clone #318

FIG. 9. Human PRL3 sequence

FIG. 10. PRL-3zumab sequence analysis. (A) light chain sequence alignment of humanized sequences identifying CDR regions (grey boxes) and identifying important domain sequences (clear boxes). (B) heavy chain sequence alignment of humanized sequences identifying CDR regions (grey boxes) and identifying important domain sequences (clear boxes).

FIG. 12. PRL3-zumab specifically binds to PRL-3, but not closely-related PRL-1 or PRL-2. (A-C) human isoforms of PRL-1, PRL-2 and PRL-3 proteins were used for analysis of PRL3-zumab specificity. (a) Western blotting of recombinant GST-PRL1, GST-PRL2, and GST-PRL3 probed with PRL3-zumab or anti-GST antibodies. (b) ELISA for PRL3-zumab using recombinant GST-PRL1, GST-PRL-2 and GST-PRL-3 proteins. (c) Immunofluorsecence staining of Chinese Hamster Ovary (CHO) cells overexpressing GFP-PRL1, GFP-PRL2 or GFP-PRL3 cells with PRL3-zumba. Bar 40 um.

FIG. 17. Clinical characteristics of SGSet1 patient cohort.

FIG. 18. Univariate and multivariate Cox regression analysis of PRL-3 expression in SGSet1 patient cohort.

FIG. 21. PRL3-zumab suppression of orthotopic liver tumors requires host FcγII/III receptor engagement. (a) Outline of orthotopic liver tumor model. (b) Western blot of PRL-3 expression in six human cancer cell lines. GAPDH, loading control. (c) Mice carrying orthotopic PRL-3+ MHCC-LM3 liver tumors had reduced tumor burden after 5 weeks of bi-weekly 100 ug/dose PRL3-zumab administration (Treated) compared to placebo (Untreated). Bar, 10 mm. (d) Mean liver tumor volumes in untreated and treated groups at Day 35. p=0.0001, t-test; data representing mean±SEM. (e) Kaplan Meier survival analysis of untreated (red lines) and treated (black lines) groups of mice. p=0.002, log-rank test. (f) Cartoon depicting domain architecture of PRL3-zumab versus PRL3-minibody, and their ability to engage Fc receptors (FcR) on host immune cells. The 2.42G2 monoclonal antibody (mAb) functions as an FcR-blocker, preventing intact IgG from binding FcRs. (g) Excised livers from mice treated with placebo (Untreated), PRL3-zumab alone, 2.4G2 mAb, PRL3-zumab+2.4G2 mAb combination therapy, human IgG, or PRL3-minibody at Day 35 were photographed and tumor volumes measured. Orthopic tumor areas framed with black lines. Bar, 10 mm. Mean liver tumor volumes in each group at Day 35. p=0.003, one-way ANOVA; data representing mean±SEM.

EXAMPLES

Example 1 Generation of PRL3-Zumab

Figure 1A:
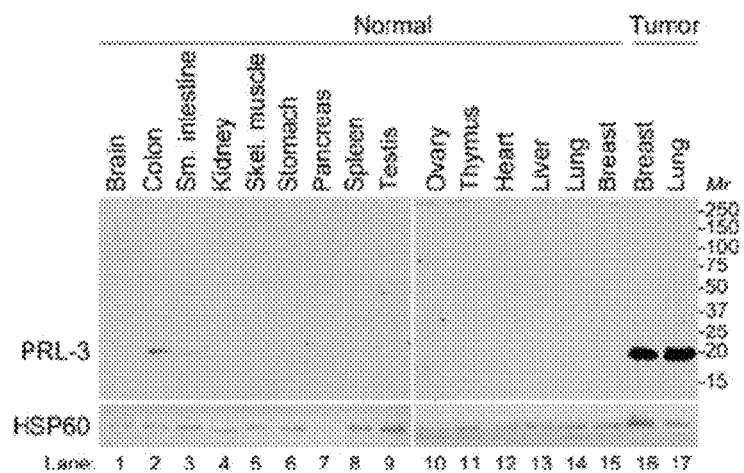
FIG. 1. PRL-3 is a novel oncotarget highly expressed in gastric tumors. (A) Western blot of PRL-3 in various normal tissues of FVB/wild-type mice (lanes 1 to 15) and spontaneous breast and metastatic lung tumors from FVB/MMTV-PyMT mice (lanes 16 and 17). Blots were probed with PRL3-zumab antibody. HSP70, loading control. (B) Kaplan-Meier survival analysis of PRL-3 mRNA expression in the SGSet1 GC patient cohort. n=183; p=0.002, log-rank test. (C) Full western blot analysis of PRL-3 in 20 pairs of human primary gastric tumors (T) versus patient-matched normal tissue (n) from GC patients. Mr, relative molecular mass (kDa).

The PRL3-zumab construct was engineered from a previously characterized murine anti-PRL-3 antibody clone. We engaged two independent contract research organizations (CROs) from US to humanise or clone, using a proprietary modification of the method described by Queen et al (60).

Briefly, the Complementarity Determining Regions (CDR) of the heavy (IgG1) and light (kappa) chains of the mouse antibody were grafted onto "acceptor" human sequence frameworks, where the framework is defined as the segment of the variable regions excluding the CDRs. The choice of human acceptor frameworks was made by aligning the mouse framework sequences against a database of human framework sequences to find the closest human homolog for each chain (typically 65-70% sequence identity).

In addition to grafting the CDRs from the mouse sequence, about three amino acid positions from the mouse sequence (in addition to the CDRs) were also grafted into the human acceptor sequence. This preserved the original murine anti-PRL-3 antibody's CDR, which specifically recognizes an epitope within a C-terminal region conserved between both mouse and human PRL-3, but not PRL-1 or PRL-2.

We invited Sapidyne Instruments Inc. (700 W Diamond St Boise, Id. 83705) to test PRL3-zumab affinity binding to PRL-3 antigen. Binding affinity analysis, using a kinetic exclusion assay (Drake et al., 2004), characterized purified PRL3-zumab to be tight binder with a Kd of 6.29 pM to purified human PRL-3, with an on rate (Kon) and off rate (Koff) of approximately $1 \times 10^7$ M-1s-1 and $7 \times 10^{-5}$ s-1, respectively (Table 1).

TABLE 1

Summary of KinExA PRL3-zumab binding affinity analysis.

| Results | PRL3-zumab | 95% confidence interval |
|---|---|---|
| $K_d$ | 6.29 pM | 5.38 pM to 7.31 pM |
| Concentration Calculated for: | PRL-3 | |
| Activity | 40% | 28.9% to 52.3% |
| Hill coefficient | 1.77 | 1.51 to 2 |
| On rate ($M^{-1}s^{-1}$) | $1.0^6 \times 10^7$ | $8.38 \times 10^6$ to $1.34 \times 10^7$ |
| Off rate ($s^{-1}$) | $6.68 \times 10^{-5}$ | |

Example 2: Use of PRL-Zumab to Treat Gastric Cancer

Material and Methods
Preparation of Tissue and Cell Lysates

Multiple normal mouse organs were harvested from FVB/wild-type mice, whereas breast and metastatic lung tumors were dissected from the isogenic FVB/MMTV-PyMT mice strain—a well-established spontaneous model of metastatic breast cancer driven by transgenic overexpression of mammary-specific Polyoma virus middle T oncogene (28). For tissues, excised samples (5 mm$^3$) were suspended in RIPA lysis buffer (Sigma) containing a protease-phosphatase inhibitor cocktail (Pierce), and disrupted completely with a tissue homogenizer (Polytron). Lysates were clarified by centrifugation at 13,000×g for 40 min at 4° C. For cell lines, $5 \times 10^6$ cells were lysed in RIPA lysis buffer containing a protease-phosphatase inhibitor and clarified as described above. Protein concentrations were estimated using a bicinchoninic assay kit (Pierce). After addition of 2× Lamelli buffer, samples were boiled and used immediately for western blotting or stored at −20° C. till use.

Western Blotting

200 µg of lysates were resolved in separate wells of 12% SDS-polyacrylamide gels and transferred to nitrocellulose membranes before blocking and probing with the indicated primary antibodies at a 1:1,000 dilution overnight at 4° C. After thorough washing with TBS-T buffer (20 mM Tris pH 7.6, 140 mM NaCl, 0.2% Tween-20), the membrane was incubated with the respective horseradish peroxidase (HRP)-conjugated secondary antibodies at a 1:5,000 dilution for 1 h, washed with TBS-T, and visualized using a chemiluminescent substrate (Pierce).

Cell Culture

The 22 human GC cell lines studied were obtained from the following sources: MKN7, MKN74, NUGC-3, OCUM-1 (Health Science Research Resources Bank); YCC-1, YCC-3, YCC-7, YCC-17 cells (Yonsei Cancer Centre); AGS, CRL-5822, KATO-III, SNU-1, SNU-5 (American Type Culture Collection, ATCC); HGC27, NUGC-4, OE19 (Sigma-Aldrich); MKN28, MKN45 (RIKEN BioResource Center); IM-95, SCH (Japanese Collection of Research Bioresources Cell Bank); SNU-484, SNU-719 (Korean Cell Line Bank). CHO cells were purchased from ATCC. The generation of CHO cells stably expressing GFP-tagged PRL-1, PRL-2 or PRL-3 fusion proteins have been previously described (23). Luciferase-expressing HCT116-luc2 human adenocarcinoma cells (Caliper Life Sciences) were established by stably transducing lantivirus containing luciferase 2 gene under the control of human ubiquitin C promotor (pGL4 luc2) into parental HCT116 cells (ATCC). Cell lines were cultured in RMPI-1640 medium (Gibco) supplemented with 10% heat-inactivated fetal bovine serum (Hyclone) and 1% penicillin-streptomycin (Life Technologies) and maintained in a 37° C. incubator supplemented with 5% $CO_2$.

Analysis of PRL-3 mRNA Expression

We analyzed a publically-available GC microarray dataset (GSE15459) from the Gene Expression Omnibus (GEO) database, consisting of 200 primary gastric cancer specimens profiled on Affymetrix Human Genome U133 Plus 2.0 Genechip arrays. Data pre-processing was carried out using the 'affyPLM' R package (v2.15). Outliers were excluded, giving a total of 185 tumor samples available for downstream analyses (SGset1; patient characteristics are provided in FIG. 17). Survival analyses, with overall survival as the outcome metric, were performed to compare tumors (n=183; 2 samples missing survival data) with "low", "medium" and "high" expression of the respective genes, i.e., "low" and "high" expression groups correspond to samples with lower than the 33.3 percentile and greater than the 66.7 percentile expression levels respectively, while the middle percentile was classified as "medium".

Preparation of Recombinant GST-Tagged Proteins

The preparation of recombinant GST-PRL-1, GST-PRL-2, and GST-PRL-3 fusion proteins have been described previously (53).

ELISA

ELISA assays was performed as described previously (53). Briefly, 96-well plates coated overnight with GST-PRL-1 (20 ng), GST-PRL-2 (20 ng) or GST-PRL-3 (1 ng, 20 ng) were blocked with 3% bovine serum albumin in PBS-0.05% Tween-20 prior to incubation with 200 ng PRL3-zumab for 2 h at 37° C. After extensive washing, HRP-conjugated anti-mouse antibody (Pierce) was added for 1 h at 37° C. Colorimetric development was performed using a Turbo-TMB substrate (Pierce) and stopped by acidification with 2M $H_2SO_4$. Absorbance was measured at 450 nm using a plate reader (Dynatech).

Animal Models and Treatments

Eight-week old male Balb/C nude mice obtained from the Biological Resource Centre (A*STAR, Singapore) were used for all animal models in this study. Mice were anesthetized with 2.5% avertin (100 µl/10 g body weight) i.p. Orthotopic gastric cancer model: Abdomen of anesthetized mice was opened in layers by a 1 cm midline incision starting from 0.5 cm below the xiphoid sternum. The stomach was taken out through the abdominal incision by surgical forceps, and cancer cells were injected into the subserosa layer. Subsequently, the stomach was placed back and the abdomen was sutured back in layers. The cell numbers required to induce orthotropic gastric tumors for each cell line and the duration of experiments were confirmed after preliminary experiments: $3 \times 10^6$ cells for SNU-484 tumors or $5 \times 10^6$ cells for IM-95, NUGC-4 and MKN-45 tumors. The treatment regime commenced on day 2 post-inoculation of cancer cells in the gastric subserosa layer. Mice were administered intravenous (i.v.) with 100 µg of PRL3-zumab (Wuxi Pharmatech) in 100 uL PBS twice a week, for a total of eight times (SNU-484 and NUGC-4 tumors) or ten times (IM-95 and MKN45 tumors). PBS was used as a control in "untreated" mice. Because of the different growth rates of the individual tumors, the duration of experiments were as follows: 4 weeks for SNU-484 and NUGC-4 tumors, 8 weeks for MKN-45 tumors, and 12 weeks for IM-95 tumors. Tumor volumes were calculated using the formula: volume=0.4×tumor length×tumor width×tumor width. Xenograph tumor model: $3 \times 10^6$ SNU-484 cells in 150 µl of PBS were injected to both flanks of anesthetized mice. After 3 weeks, the resultant tumors (5-10 mm) were surgically removed under anesthesia and mice were divided into 2 groups, receiving either PRL3-zumab (100 µg in 100 µL PBS, i.v.) or PBS (100 µL) biweekly after tumor removal. Tumor relapse was analyzed weekly in both untreated and treated group up till 7 weeks post-resection. Tumor growth was monitored carefully in both groups. Secondary gastric metastasis model: $3 \times 10^6$ HCT116-luc2 cells were directly implanted into the gastric serosa of anesthetized mice as described. Mice were divided into treated (PRL3-zumab, 100 ug in 100 uL PBS) or untreated (100 uL PBS) groups, and tumor growth in vivo at weeks 1, 2 and 3 post-implantation was monitored by IVIS imaging under 2% isofluorane anaesthesia 15 minutes after intraperitoneal injection of 150 mg/kg luciferin (Caliper Life Sciences).

Analysis of Mice Blood Samples

WBC staining of mouse blood smears: After smearing a thin layer from a drop of fresh mouse blood on a glass slide, slides were baked at 37° C. for 1 h before flooding with modified Wright Giemsa stain (Sigma) for 1 min followed by washing with deionized water for 3 min. After drying, the stained slide was observed under microscope, with WBCs stained blue. Estimation of total WBC was performed under light microscopy (Olympus) by counting in ten visual fields in each slide and calculation using the equation WBCs/µl= (total number of counted WBC/number of fields)×2000. Full blood counts: Hematological analysis of mice samples was conducted by Quest Laboratories (Singapore).

Antibodies

HSP70 (cat #EXOAB-Hsp70A) antibodies were purchased from System Biosciences, Inc. Calnexin (cat #2679) antibody was purchased from Cell Signaling. CD63 (cat #sc-15363) antibody was purchased from Santa Cruz Biotechnoloy. GAPDH (clone MAB374) antibody was purchased from Millipore. B cell marker (CD45/CD220, clone RA3-6B2) and NK cell marker (CD335/Nkp46, clone 29A1.4) were purchased from BD Pharmingen.

Immunofluorescence Imaging

Preparation of cell slides: Cells were seeded directly onto glass coverslips and grown for 48 h. After washing twice with PBSCM (PBS pH 7.0, 1 mM $MgCl_2$, 1 mM $CaCl_2$), cells were fixed in 3% paraformaldehyde for 20 min at room temperature (RT), washed and permeabilized for 15 min with PBS-0.1% saponin (Sigma). Preparation of tissue section slides: Fresh-frozen specimens of SNU-484 and MKN45 orthotopic gastric tumors were sectioned into 10 μm slices using a cryostat (Leica) at −18° C. The slides were fixed with 4% paraformaldehyde for 20 min, washed with PBS-0.05% Tween-20, and blocked in PBS-FDB (PBS pH 7.0, 2% BSA, 5% goat serum, 5% fetal bovine serum) for 1 h at RT. Slides were subsequently incubated with the indicated primary antibodies at a 1:200 dilution at RT for 4 h, washed, and incubated for 2 h with the corresponding fluorochrome-conjugated secondary antibodies (Life Technologies). Washed slides were mounted with a DAPI-containing anti-fade mounting reagent (Vector Laboratories) and sealed using nail polish. Confocal imaging was performed with an LSM 510 confocal microscope (Zeiss AG).

Immunohistochemistry for PRL3-Zumab

10 μm-thick cryosection slides were fixed with 4% formalin for 20 min and incubated with 1% $H_2O_2$-PBS in the dark for 5 min. Washed slides were then blocked in PBS containing 10% goat serum and 1% BSA (Sigma) for 1 h at RT. Subsequently, slides were washed four times in PBS-0.05% Tween-20 with gentle shaking and incubated with goat anti-human labeled polymer-HRP (Dako) for 2 h before washing extensively and incubating with substrate-chromogen solution (Dako) for 10-20 min in the dark. Mounted slides were examined using a brightfield microscope (Olympus) and representative images were captured.

Statistical Analysis

For human studies, the log-rank test was used to assess the significance of the Kaplan-Meier analysis of overall GC patients' survival, based on PRL-3 mRNA expression grouping. Univariate and multivariate analyses were performed using Cox proportional hazards regression. For mouse studies, the log-rank test was used to assess significant differences of the Kaplan-Meier analysis of overall survival between 'untreated' and 'treated' mice groups. The Student's t-test was used to calculate statistical significant differences in orthotopic tumor volumes. SPSS software v19.0 (IBM) was used for statistical calculations. In all instances, p values <0.05 were considered significant.

Results

PRL-3 is a Tumor-Specific Target

Figure 11A:
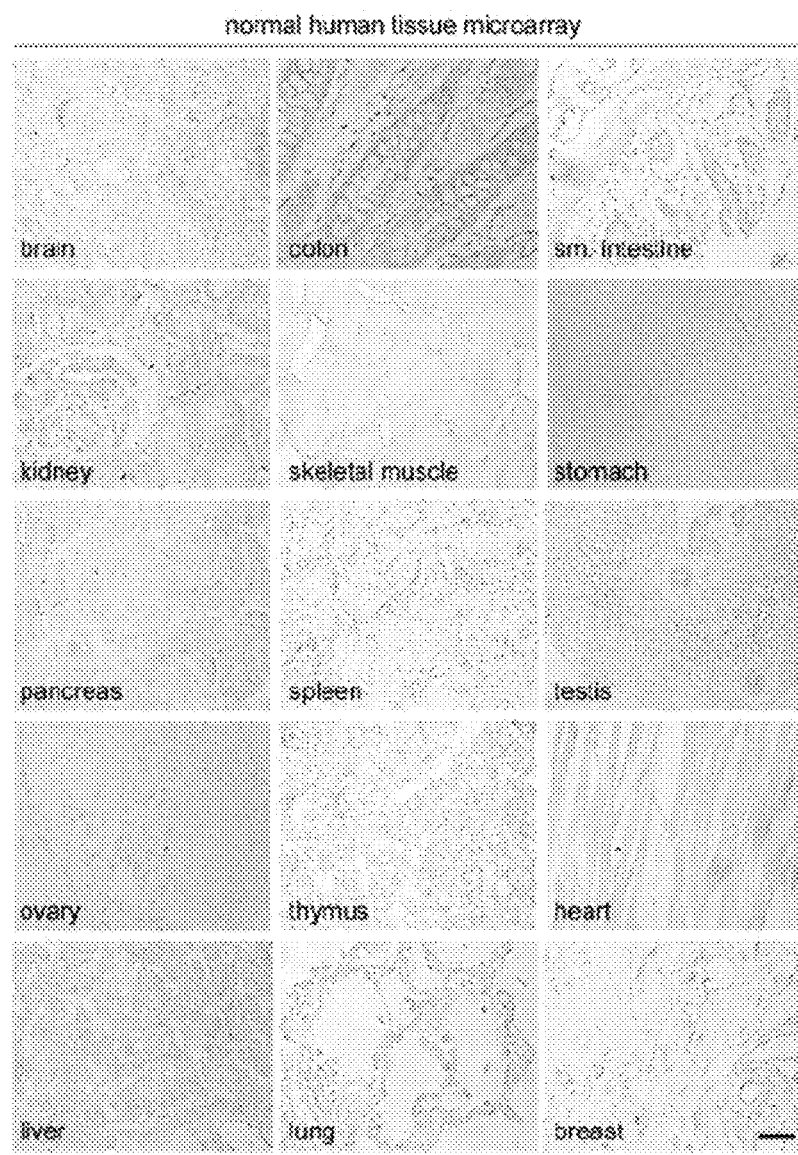
FIG. 11. PRL-3 is not expressed in normal adult human tissues yet strongly expressed in human gastric tumors. (A) immunohistochemistry of (a) multiple normal human tissues from various organs and (b) matched gastric tumor and normal stomach tissues from a GC patient for PRL-3 expression. Bar 50 um.
Figure 11B:
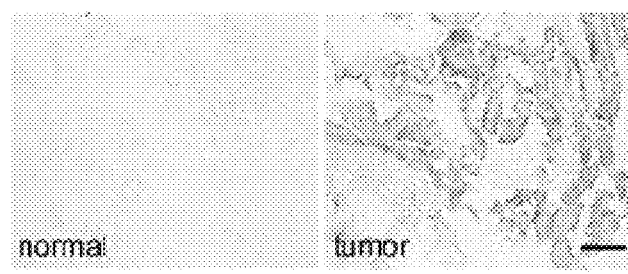
Figure 13A:
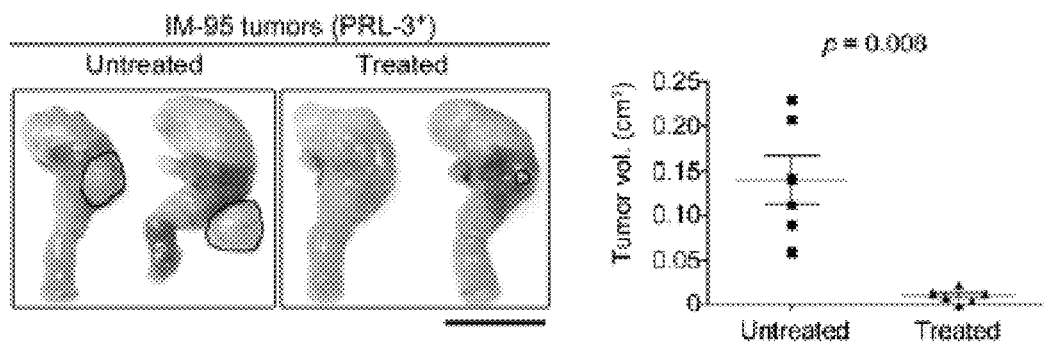
FIG. 13. PRL3-zumab inhibits the tumor growth of PRL-3+ orthotopic gastric tumors in mice. 8 week old male BALB/C nude mice were implanted with PRL-3-positive NUGC-4 or IM-95 cell lines to induce orthotopic gastric tumors. At the end of the experiment, visible tumors (outlined in black) were measured and volumes compared. (a) Stomachs with IM-95 tumors from untreated and PRL3-zumab-treated mice. Rightmost panel, chart indicating the mean tumor volume of IM-95 tumors in untreated and PRL3-zumab treated mice. p=0.008, t-test n=6, data representing mean±S.D. Bar 10 mm (b) Stomachs with NUGC-4 tumors from untreated and PRL3-zumab treated mice. Rightmost panel, mean tumor volumes of NUGC-4 tumors in untreated and PRL3-zumab-treated mice. p=0.003, t-test; n=4, data representing mean±S.D. bar, 10 mm. (C) PRL3-zumab, but not human IgG isotype control, suppresses PRL3 positive gastric tumor growth in vivo. Eight week old male BALB/C nude mice were implanted with PRL3 positive SNU-484 tumors in untreated, human IgG-treated (hIgG), and PRL3-zumab-treated mice. P<0.001, one-way ANOVA; n=4 per group, data representing mean±SEM. *** p<0.001, Tukey's post-hoc test (untreated vs treated groups).
Figure 13B:
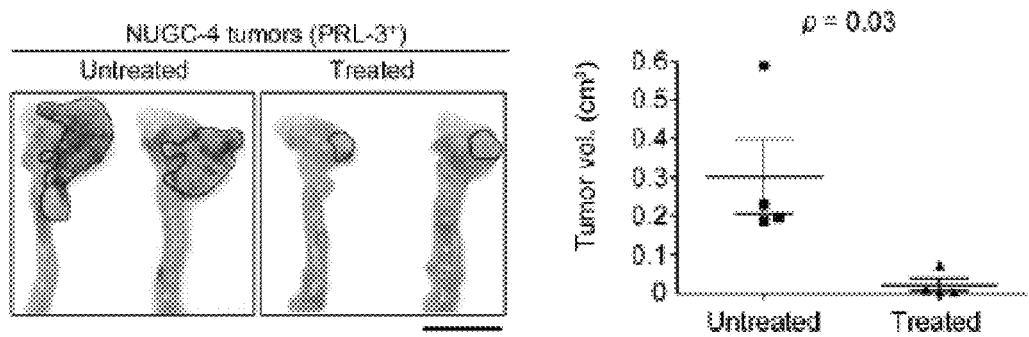
Figure 13C:
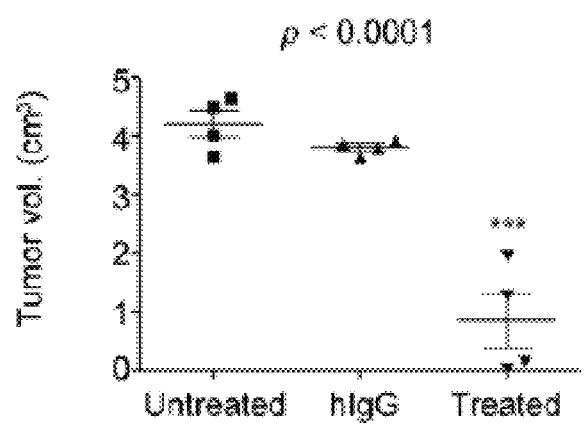

A pertinent challenge in the development of anti-cancer targeted therapy is the identification of 'tumor-specific antigens' that are exclusively expressed in tumors, but not in normal tissues, so as to avoid undesirable off-target effects. We first screened normal murine tissues from all major organs by western blotting for endogenous PRL-3. In these full blots, a single ~20 kDa endogenous protein corresponding to PRL-3's predicted molecular weight was detected (FIG. 1A). We did not observe any non-specific bands, confirming PRL-3 antibody did not cross-react with other molecules (27). Although PRL-3 protein was weakly detected in normal colon (FIG. 1A, lanes 2), it was undetectable in 14 other major normal murine tissues examined (FIG. 1A, lanes 1, 3-15), including breast and lung tissues (FIG. 1A, lanes 14-15). In contrast, PRL-3 was abundantly expressed in spontaneously-developed breast and lung tumors (FIG. 1A, lanes 16-17) from MMTV-PyMT mice (28). Importantly, PRL-3 protein was also undetectable in 15 major normal Human Organs examined by immunohistochemistry (FIG. 11A). Furthermore, in patient-matched tissue samples, PRL-3 was undetectable in noncancerous gastric tissues (FIG. 11B, panel a), but highly expressed in gastric tumor sections (FIG. 11B, panel b), again, showing tumor-specific upregulation. Taken together with published literature on the high frequency of PRL-3 overexpression in cancers (29), and the recent observation that PRL-3-conditional knockout mice appear grossly normal (30), the specific expression of PRL-3 in cancerous tissues but not in normal tissues validates PRL-3 as an appropriate tumor-specific target.

PRL-3 Oncoprotein is Overexpressed in 85% of Gastric Tumors Examined

Figure 1B:
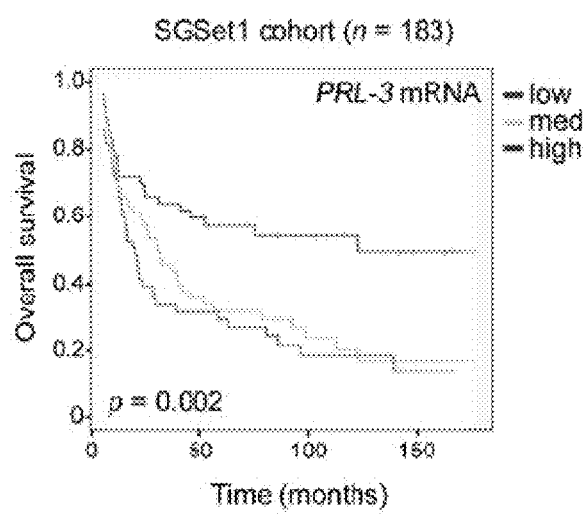
Figure 1C:
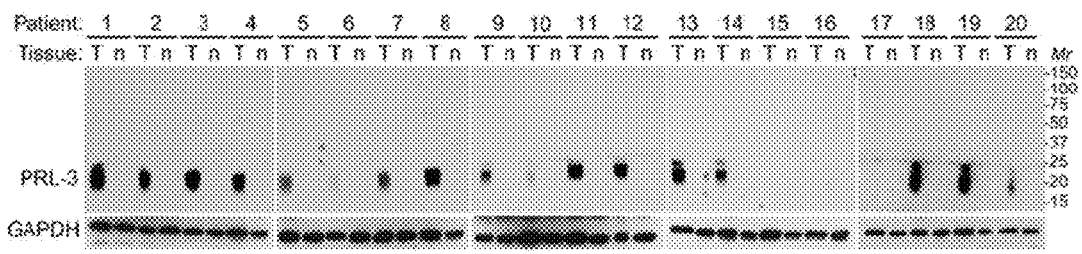

Over the past decade, a number of studies have demonstrated that elevated PRL-3 expression is a negative prognostic factor for gastric cancer (14,31,32). We further studied the clinical significance of elevated PRL-3 mRNA levels in an independent cohort of 185 GC patients (clinical characteristics given in FIG. 17). Kaplan-Meier survival analyses revealed that elevated PRL-3 mRNA levels in tumors were associated with shorter overall survival (p=0.002; FIG. 1B). In multivariate Cox analysis, high PRL-3 mRNA expression was also significantly associated with higher tumor grades (FIG. 18). Next, we examined the levels of PRL-3 protein using 20 matched, fresh-frozen biopsy tissue sample pairs (tumor vs adjacent normal tissue) from GC patients admitted to the National University Hospital of Singapore. Western blots clearly showed endogenous PRL-3 overexpressed in 17/20 (85%) gastric tumors (T; FIG. 1C), but not in any of the matched normal gastric tissues (n; FIG. 1C), validating the tumor-specific expression of PRL-3. Notably, PRL-3 protein appeared as a broad band between 20 to 25 kDa in these blots, suggesting potential post-translational modifications of PRL-3 (~20 kDa) in human tumor samples that are yet to be defined. Collectively, our clinical data characterize PRL-3 oncoprotein overexpression as a common phenomenon in human GC correlating with disease severity, reaffirming its suitability as a candidate for targeted therapy.

Generation of a Novel PRL-3-Targeting Humanized Antibody, PRL3-Zumab

We previously demonstrated the high efficacy of murine and chimeric PRL-3 antibodies against tumors expressing intracellular PRL-3 in both nude and wild type C57BL/6 mice (24,27). In these studies, mice receiving PRL-3 monoclonal antibodies gained weight continuously and displayed normal activities, suggesting minimal off-target side effects. To translate these early findings towards a clinical application in humans, we generated a humanized monoclonal anti-PRL-3 antibody referred to as 'PRL3-zumab'. Similar to its predecessor, engineered PRL-3-zumab specifically recognized PRL-3 and did not cross-react with the PRL-3 homologues PRL-1 or PRL-2 by western blotting, ELISA, and immunofluorescence analysis (FIGS. 12A-C). Subsequently, we used PRL3-zumab for all further experiments described in this report.

Figure 2A:
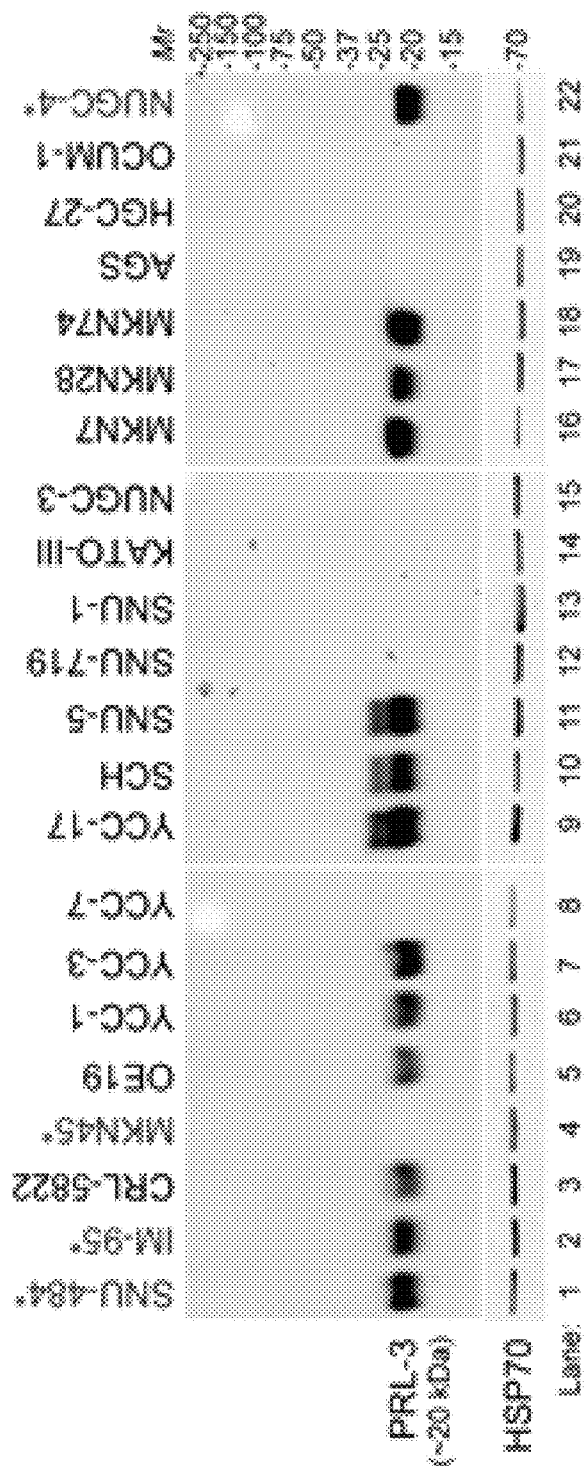
FIG. 2. PRL3-zumab specifically blocks PRL-3$^+$ orthotopic gastric tumors. (A) Western blot for endogenous PRL-3 in 22 human GC cell lines. Tumorigenic PRL-3$^+$ and PRL-3$^-$ cell lines selected for subsequent animal models are indicated in red with an asterisk (*). Mr, relative molecular mass (kDa). (B) Outline of the experimental orthotopic GC model in Balb/C nude mice. (C) PRL3-zumab treatment inhibits PRL-3$^+$ SNU-484 orthotopic gastric tumor growth. Panels a-b, mice appearance at the end of the experiment (Day 28). Arrows highlight abdominal distention in untreated mice. Panels c-d, excised stomachs with tumor areas framed with a black line. Bar, 10 mm. (D) Mean gastric tumor volumes in untreated and PRL3-zumab-treated groups at Day 28. n=8 per group; p=0.01, t-test; data representing mean±S.D. (E) Kaplan Meier survival analysis of untreated (red lines) and PRL3-zumab-treated (black lines) groups of mice. n=4 per group; p=0.006, log-rank test. p-values <0.05 were considered statistically significant.
Figure 2B:
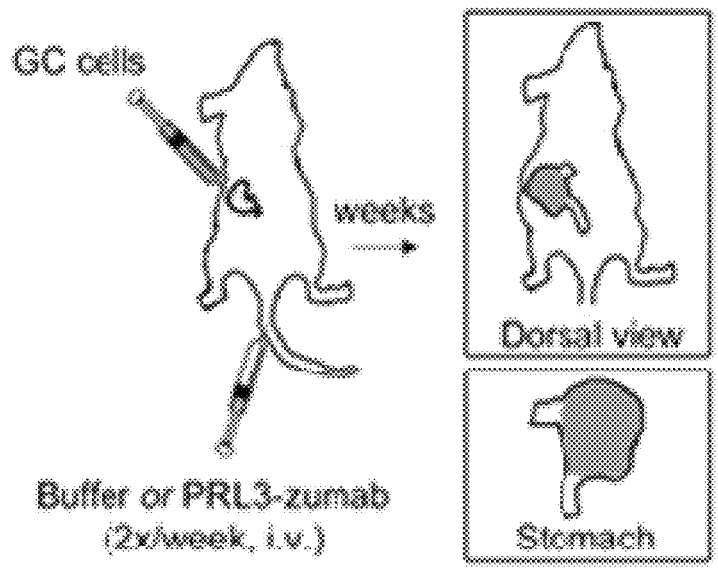

PRL3-Zumab Specifically Blocks Growth of PRL-3-Positive (PRL-3+) but not PRL-3-Negative (PRL-3) Orthotopic Gastric Tumors Human cancer cells growing in their natural (orthotopic) locations in mouse tumor models replicate human disease with high fidelity. More importantly, tumor responses to therapy have been shown to vary dramatically depending on whether cancer cells are implanted in a subcutaneous versus orthotopic location (33), highlighting the requirement of choosing the right model for assaying therapeutic efficacies of anti-tumor agents. To establish a relevant preclinical orthotopic mouse model to examine the efficacy of PRL3-zumab against gastric tumors, we first screened a panel of 22 human GC cell lines for PRL-3 protein expression status, and subsequently tested their tumorigenic capacity within the subserosa layer of stomachs in mice. PRL-3 protein was detected in 13 out of 22 (59%) human GC cell lines analyzed (FIG. 2A). However, only a subset of GC cell lines grew well in culture and formed orthotopic tumors within manageable time frames (<2 months). Based on these criterion, three PRL-3$^+$ cell lines (SNU-484, NUGC-4 and IM-95) and one PRL-3$^-$ cell line (MKN45) were selected for developing orthotopic GC models to assess the anti-tumor efficacy of PRL3-zumab. Cells from these lines were inoculated into the subserosa layer of the stomach, and subsequently treated following the protocol outlined in FIG. 2B. At the end of the experiment, stomachs were harvested from mice and analyzed for gastric tumor burden.

Figure 2C:
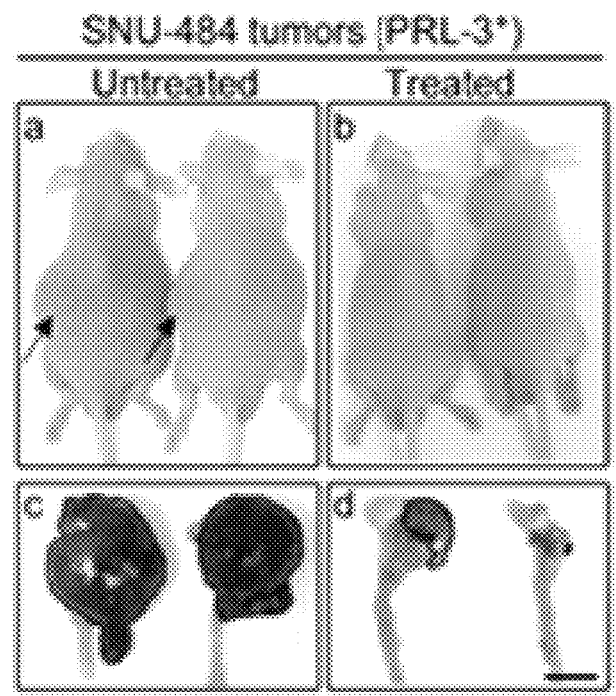

We first studied the effect of PRL3-zumab treatment on the SNU-484 GC cell line, which served as an excellent PRL-3$^+$ orthotopic gastric tumor model due to its high expression of PRL-3 protein (FIG. 2A, lane 1), rapid growth in cultures, and reproducible gastric tumor formation within 3-4 weeks. Over the course of the experiment, untreated mice developed pronounced abdominal distention (FIG. 2C, panel a, arrows) and displayed reduced physical activity and food intake, whereas PRL3-zumab treated mice appeared grossly normal (FIG. 2C, panel b) and maintained normal physical activity with regular food intake patterns. Upon dissection, orthotopic tumor formation was visibly reduced in the PRL3-zumab-treated group compared to the untreated group (FIG. 2C, panels c-d).

Figure 2D:
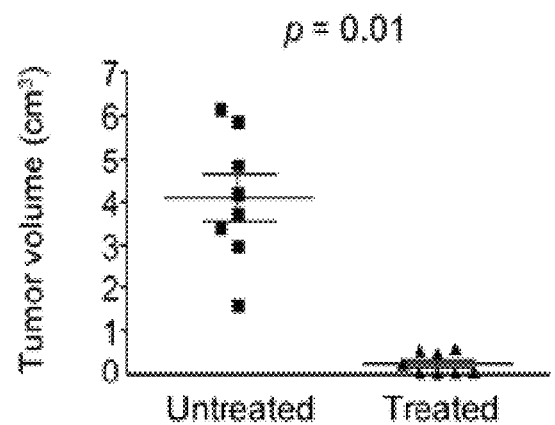
Figure 2E:
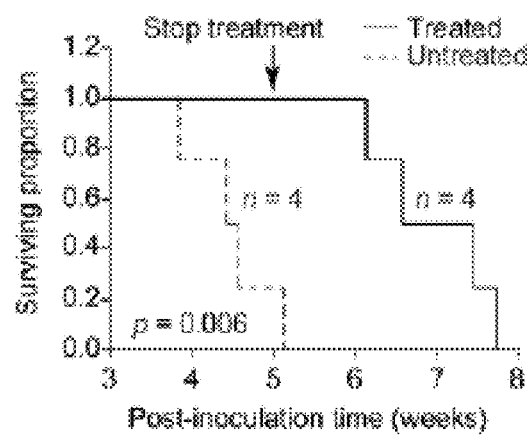

Measurement of tumor volume revealed a significant, 20-fold reduction of tumor burden in the PRL3-zumab treated group (0.23±0.25 cm$^3$) compared to the untreated group (4.08±1.52 cm$^3$; p=0.01; FIG. 2D). In line with reduced tumor burden, Kaplan-Meier analysis revealed a significantly longer survival time in PRL3-zumab-treated mice compared to untreated mice with a median survival time of 7 versus 4.5 weeks, respectively (p=0.006; FIG. 2E), confirming that mice carrying PRL-3$^+$ SNU-484 gastric tumors responded effectively to PRL3-zumab anti-tumor therapy. To validate this finding, orthotopic GC mouse models were generated using two additional PRL-3$^+$ GC cell lines, IM-95 and NUGC-4 (FIG. 2A, lanes 2 and 22 respectively). Similar to SNU-484 orthotropic tumors, PRL3-zumab treatment significantly suppressed the growth of gastric tumors formed by either PRL-3$^+$ IM-95 cells (p=0.008; FIG. 513A) or PRL-3$^+$ NUGC-4 cells (p=0.03; FIG. 513B).

Figure 3A:
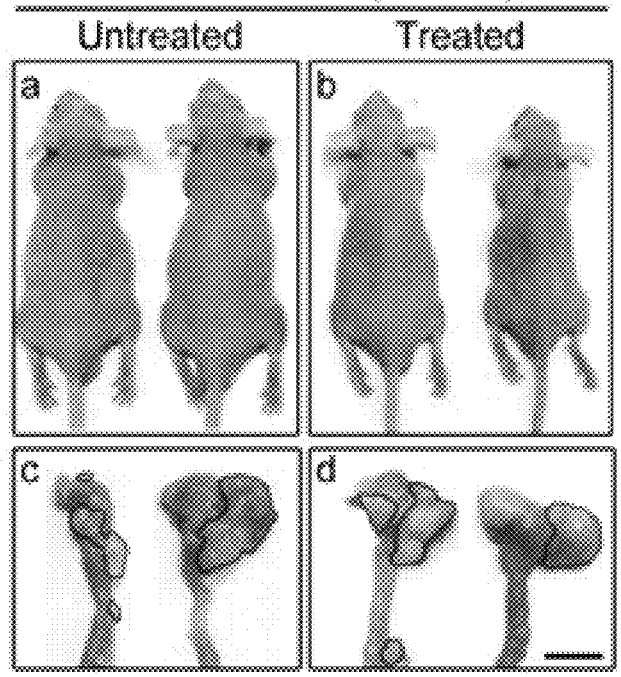
FIG. 3. PRL3-zumab has no therapeutic effect on PRL-3$^-$ orthotopic gastric tumors. (A) PRL3-zumab treatment could not block PRL-3$^-$ MKN45 orthotopic gastric tumor growth. Panels a-b, mice appearance at the end of the experiment (Day 56). Panels c-d, excised stomachs with tumor areas framed with a black line. Bar, 10 mm. (B) Mean gastric tumor volumes in untreated and PRL3-zumab-treated groups at Day 56. n=5 per group; p=0.4, t-test; data representing mean±S.D. (C) Kaplan Meier survival analysis of untreated (red lines) and PRL3-zumab-treated (black lines) groups of mice. n=4 per group; p=0.3, log-rank test. (D) Summary of PRL3-zumab treatment outcomes in orthotopic models of 4 human GC cell lines. p-values <0.05 were considered statistically significant. (E) Mean gastric tumor volumes fat day 28 from MKN45-PRL3 orthotopic gastric tumor growth. N=4 (untreated) or 5 (treated) 'p=0.00002, t-test' data representing mean±SEM.
Figure 3B:
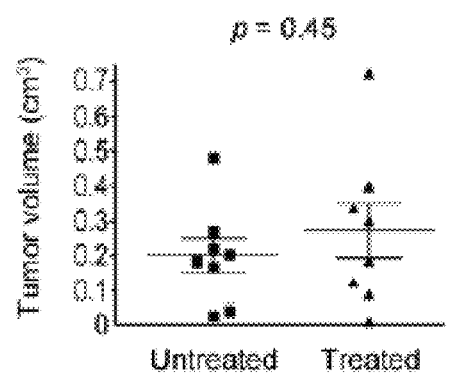

In striking contrast, gastric tumors formed by MKN45, a PRL-3$^-$ GC cell line (FIG. 2A, lane 4), showed no response to PRL3-zumab treatment, with pronounced abdominal distention (FIG. 3A, panels a-b) and orthotopic tumor formation (FIG. 3A, panels c-d) present in mice from both treated and untreated groups. No difference in mean orthotopic tumor volume was found between treated (0.17±0.20 cm$^3$) and untreated (0.13±0.19 cm$^3$) groups (p=0.4; FIG. 3B). Kaplan-Meier survival analysis revealed no significant difference in overall survival between untreated and treated groups, with median survival at 9.25 weeks in the untreated group versus 10 weeks in PRL3-zumab treated group (p=0.3; FIG. 3C). The results from PRL3-zumab treatment of orthotopic tumors derived from these four cell lines (summarized in FIG. 3D) cement a fundamental principle we previously proposed regarding PRL-3 antibody therapy (24)—only PRL-3$^+$ tumors respond to PRL3-zumab therapy, while tumors lacking PRL-3 oncoprotein expression do not.

Figure 4A:
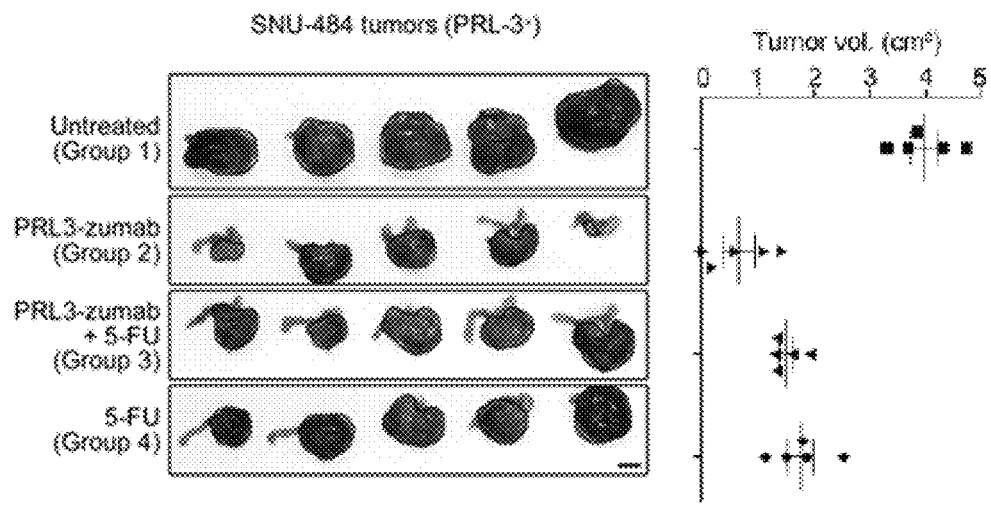
FIG. 4. PRL3-zumab is more effective as a monotherapy rather than in combination therapy with 5-fluorouracil (5-FU), or 5-FU alone. Four treatment groups were used to treat PRL-3$^+$ SNU-484 orthotopic tumors: PBS control (Group 1), PRL3-zumab monotherapy (Group 2), PRL3-zumab+5-FU combination therapy (Group 3), or 5-FU monotherapy (Group 4). (A) Excised mice stomachs from each treatment group at Day 28, with orthotopic tumor areas framed with a black line. Bar, 10 mm. Right panel, mean gastric tumor volumes in each group at Day 28. n=5 per group; p-values indicated for each group when compared to Group 1, t-test; data representing mean±S.D. (B) Representative images of Giemsa-stained blood smears from treated mice groups before the start of therapy (Day 0) and at the end of the experiment (Day 28). White blood cells (WBCs) are stained blue. Bar, 40 µm. Right panel, mean WBC count from blood smears from each mouse at Day 28. n=5 per group; p-values indicated for each group when compared to Group 1, t-test; data representing mean±S.D. p-values <0.05 were considered statistically significant. (C) Haematological profiles of mice groups at the end of the various treatment regimens (Day 28). Values highlighted in red indicate outliers from the normal reference range for BALB/c nude mice (35).

PRL3-Zumab is More Effective as a Monotherapy than a Combination Therapy with 5-Fluorouracil (5FU) or 5-FU Alone Since 5-FU is a chemotherapeutic drug used as first line treatment of gastric cancer (17), we studied whether PRL3-zumab may be more effective in combination with 5-FU in inhibiting orthotopic tumor growth. We tested four treatment protocols: PBS control (Group 1), PRL3-zumab monotherapy (Group 2), PRL3-zumab+5-FU combination therapy (Group 3), or 5-FU monotherapy (Group 4). According to the treatment protocol, bi-weekly doses of PRL3-zumab (100 µg/dose) or 5-FU (30 mg/kg/dose) were administered individually, or in combination, intravenously into groups of nude mice carrying orthotopic PRL-3$^+$ SNU-484 gastric tumors. During the course of the experiment, we observed a reduction in overall animal activity in 5-FU-treated mice (Groups 3 and 4). Analysis of tumor volumes indicated that PRL3-zumab monotherapy (Group 2) had the highest therapeutic efficacy, with the lowest mean tumor volume of 0.67±0.59 cm$^3$, followed by the PRL3-zumab+5-FU combination treatment (Group 3; 1.49±0.27 cm$^3$), the 5-FU monotherapy (Group 4; 1.76±0.52 cm$^3$), and, finally, the PBS control (Group 1; 3.98±0.60 cm$^3$; FIG. 4A). These results suggest that PRL3-zumab is more effective at reducing gastric tumors when used without the chemotherapeutic agent, 5-FU.

Figure 4B:
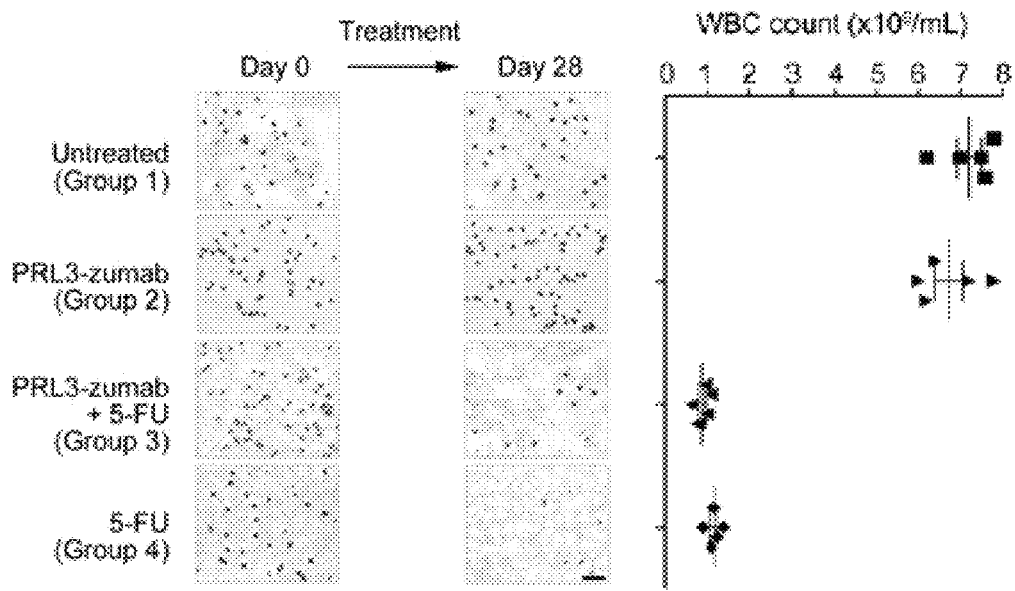

Previously, we emphasized a critical role of the host immune system in the efficacy of PRL-3 antibody therapy (24). In light of the known side effects of 5-FU treatment in causing a non-specific reduction in the numbers of white blood cells (WBC) (34), we investigated whether the reduction in therapeutic efficacy observed might be due to this phenomenon. In whole blood smears, we found a 5-fold reduction in peripheral WBC counts after 5-FU treatment (Groups 3 and 4) compared to control (Group 1) or PRL3-zumab monotherapy (Group 2; FIG. 4B). To validate these results, we performed full blood counts of mice samples to analyze the haematological effects of the different treatment regimens at the end of the experiment (Day 28). Whereas mice receiving PRL3-zumab had a general haematological profile within the normal range for the BALB/c nude strain (35), those receiving 5-FU in combination with PRL3-zumab, or 5-FU alone, displayed reduced neutrophil, lymphocyte, and monocyte counts, together with marked reductions in red blood cell and platelet counts (FIG. 4C). Taken together, our results suggest that the reduction in immune function as a result of 5-FU treatment may account for the reduced efficacy of PRL3-zumab when used in combination with 5-FU, and supports our previous finding that PRL-3 antibody therapy requires a stronger immune system.

Postoperative PRL3-Zumab Therapy Suppresses Recurrence of PRL-3$^+$ Tumors

Figure 19A:
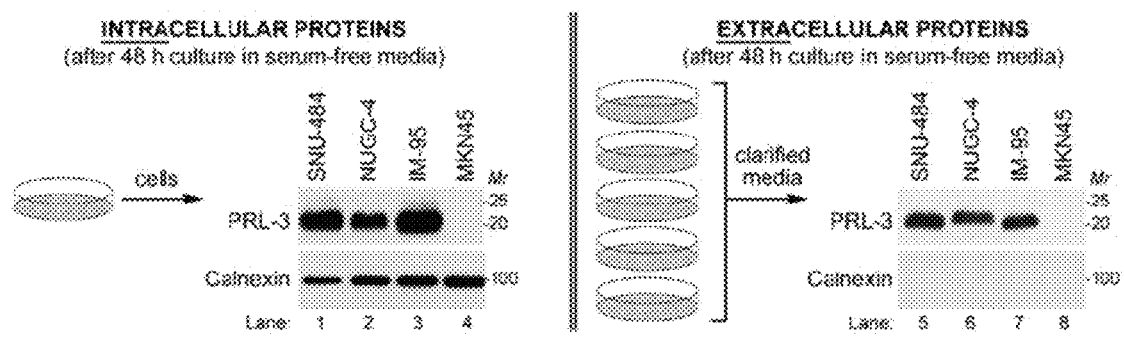
FIG. 19. PRL3 oncoprotein may be secreted out of cancer cells and act as bait for PRL3-zumab. (A) Analysis of PRL3 protein expression in intracellular protein pools (cell lysate) and extracellular protein pools (concentrated conditioned media) after culturing gastric cancer (GC) cells in serum-free media for 48 h. For extracellular protein analysis, conditioned media (50 mL) from five dishes of GC cells were first cleared of dead cells and cellular debris, followed by centrifugal concentration (final volume ~0.2 mL). (B) Orthotopic SNU-484 and MKN45 tumor tissue cryo-sections from mice subject to various treatments were analysed by immunohistochemistry for PRL3-zumab using anti-human IgG antibodies. Bar 20µ<µM.
Figure 19B:
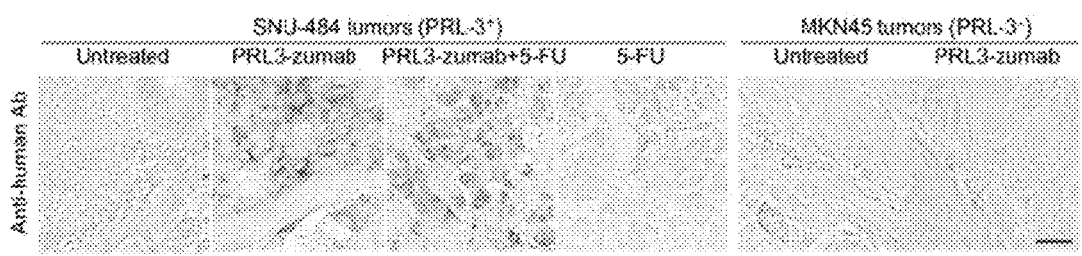

Although surgery is the cornerstone in the treatment of GC, nearly 80% of patients die within a short period of time largely due to locoregional recurrence and/or, to a lower extent, distant metastasis (36). In light of PRL3-zumab's ability to suppress PRL-3$^+$ GC growth in vivo, we investigated if PRL3-zumab also had efficacy as a postoperative adjuvant treatment to suppress tumor recurrence. Using PRL-3$^+$ SNU-484 GC cells, we first established xenograft tumors (between 5-10 mm width) in both flanks of nude mice over the course of 3 weeks (FIG. 19, panel a). The resulting solid tumors were then completely removed via careful surgery (FIG. 19, panel b), and mice were divided into 2 groups for bi-weekly injections with control antibody (untreated), or PRL3-zumab (treated). Local tumor recurrence was then monitored weekly. By 7 weeks post-surgery, the untreated group had developed large local tumors at resection sites (FIG. 19, panel c). In contrast, over the same period, no visible tumor growth was observed at resection sites in mice receiving PRL3-zumab therapy (FIG. 19, panel d). This was confirmed upon dissection—whereas large solid tumors could be harvested from the untreated group (FIG. 19, panel e), no solid tumors were found in the PRL3-zumab-treated group at resection sites (FIG. 19, panel f). Collectively, these results show that PRL3-zumab has efficacy in suppressing postoperative local tumor recurrence, suggesting a possible avenue for clinical translation of this drug as an adjuvant therapy.

Figure 14A:
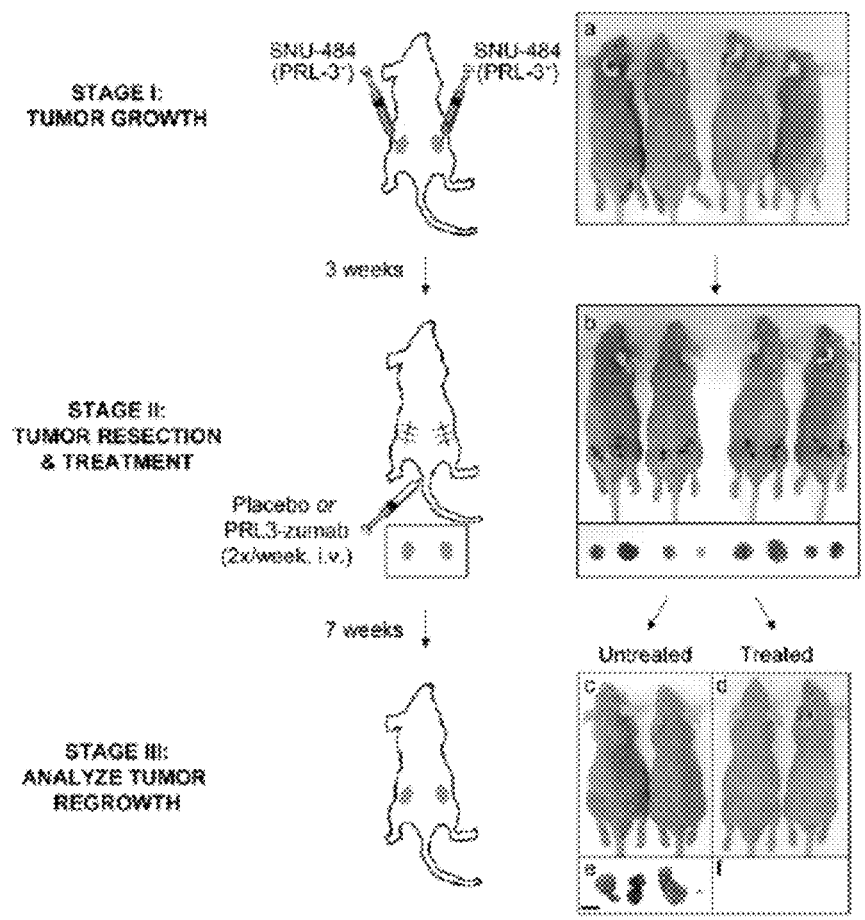
FIG. 14. Postoperative PRL3-zumab therapy suppresses recurrence of PRL-3+ tumors. (A) Xenograft tumors formed by PRL-3+ SNU-484 cells were grown for 3 weeks before tumor resection. Mice were subsequently divided into placebo (untreated) or PRL3-zumab (treated) groups, and treated bi-weekly for 7 weeks to monitor tumor regrowth. Panel a, tumor-bearing mice appearance at the end of 3 weeks. Panel b, mice appearance after surgical resection of tumors, with dissected tumors shown in lower panel. Panels c-d, mice appearance 7 weeks after resection and treatment. Panel e, dissected tumors which recurred at resection sites. Panel f, no tumor recurrence in treated mice. Bar, 10 mm. (B) Kaplan Meier recurrence-free survival analysis of untreated (n=10) and treated (n=8) groups of mice. P<0.001, log-rank test.
Figure 14B:
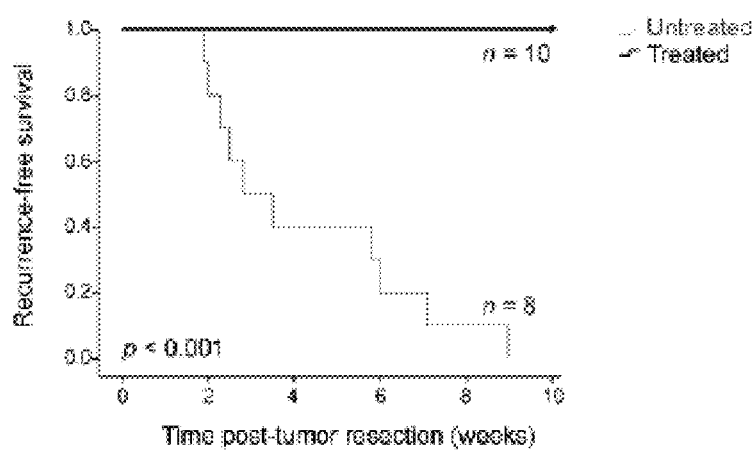
Figure 15A:
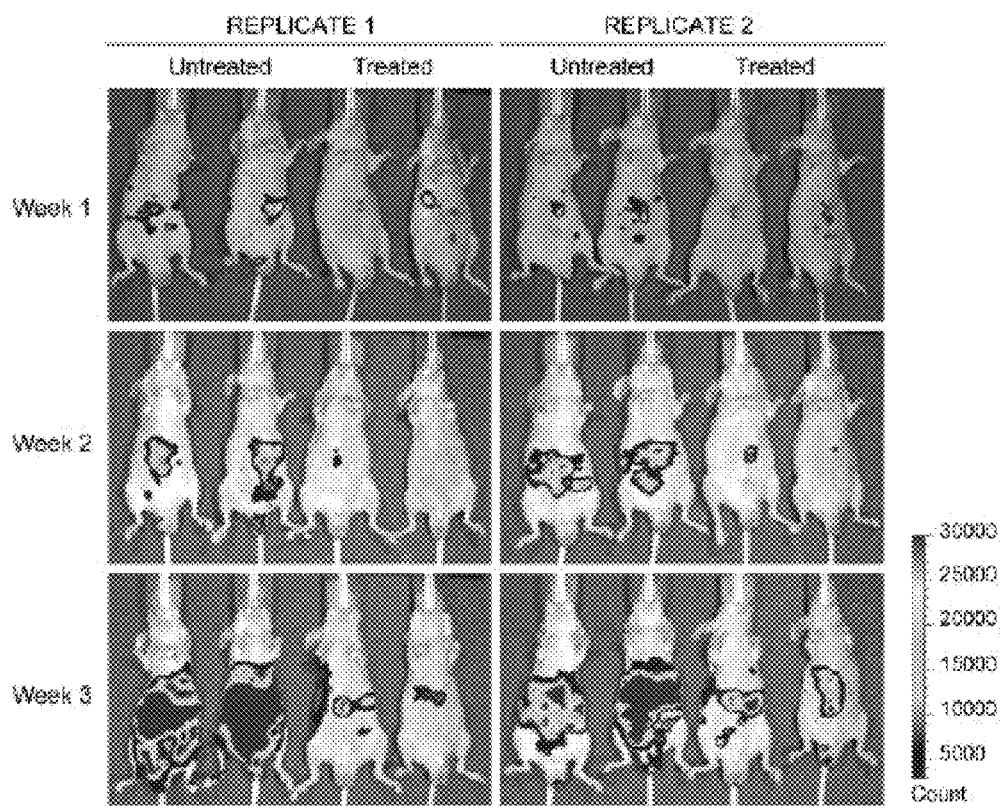
FIG. 15. PRL3-zumab inhibits local and metastatic abdominal tumors formed by PRL-3+ HCT116 colorectal cancer cells implanted within the stomach. HCT116-luc2 cells were implanted into the gastric subserosa layer of mice stomachs to mimic secondary colorectal cancer metastasis to the gastric niche. PRL3-zumab treatment reduced growth of HCT116-luc2 tumors in the gastric niche. (A) IVIS imaging of global in vivo tumor growth over 3 weeks post-inoculation. (B) Mice from (A) were analyzed for whole-animal IVIS intensity changes over time. n=4 per group; p<0.001, two-way ANOVA. (C) Tumor burden in excised stomachs at the end of week 3. (D) Stomachs from (C) were analyzed for differences in IVIS intensity. n=4 per group; p=0.01, t-test; data representing mean±SEM. (E) Metastatic tumor burden within abdominal walls at the end of week 3. (F) Stomachs from (E) were analyzed for differences in IVIS intensity. n=4 per group; p=0.0003, t-test; data representing mean±SEM.
Figure 15B:
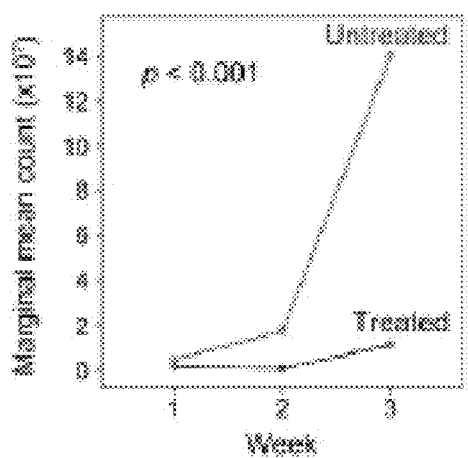
Figures 15C, 15E:
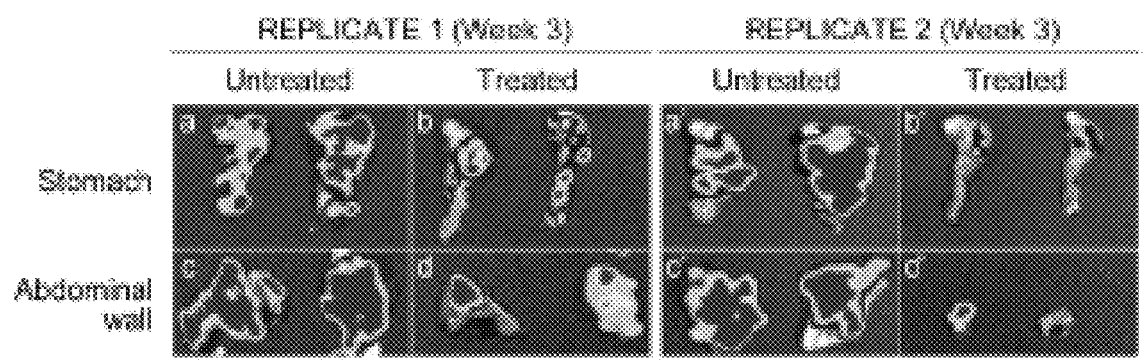
Figure 15D:
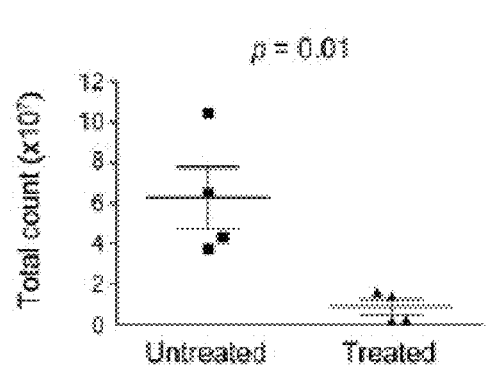
Figure 15F:
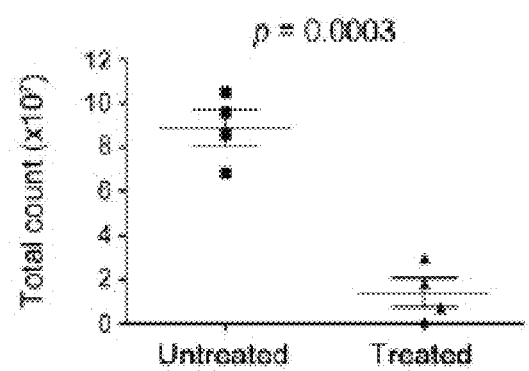

PRL3-Zumab Suppresses Growth of Secondary PRL-$3^+$ Tumor Metastasis in the Stomach The presence of metastasis in the stomach is a rare condition (37-39) which is almost invariably associated with poor prognosis (40,41). To address if PRL3-zumab could block metastatic tumor formation, we developed an experimental model of colorectal cancer metastasis to the stomach using PRL-$3^+$ HCT116-luc2 colorectal cancer cells surgically injected into the gastric subserosa layer of mice. We used HCT116-luc2 cells for two primary reasons: 1) gastric metastasis from colon cancer has been described in humans (38,39,42), and 2) HCT116-Luc2 constitutively express firefly luciferase, allowing monitoring of tumor growth using an In Vivo Imaging System (IVIS). In 2 separate experimental replicates, whereas PRL-$3^+$ HCT116-luc2 tumors grew rapidly in untreated mice, PRL3-zumab-treated mice had much reduced PRL-$3^+$ HCT116-luc2 tumor growth over the same period (FIG. 14A). Upon dissection, heavy tumor burden was observed in stomachs of untreated mice (FIG. 14B, panels a, a'). In contrast, PRL3-zumab treated mice had much lower stomach tumor burden (FIG. 14B, panels b, b'). In addition, the extensive metastatic dissemination to abdominal walls was seen in untreated mice (FIG. 14B, panels c, c') was also greatly reduced in treated mice (FIG. 14B, panels d, d'). Collectively, these results suggested that PRL3-zumab could reduce growth and metastases of PRL-$3^+$ HCT116-luc2 colorectal cancer tumors in and around the gastric niche.

Figures 5A, 5B:
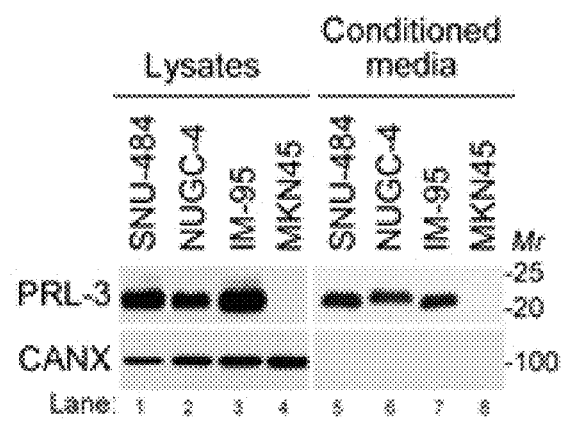
FIG. 5. Intracellular PRL-3 oncoprotein can be secreted into cell culture media and is present in 62% of cancer urines, but not in normal urines. (A) Western blotting of PRL-3 in matched lysates and conditioned culture media of the indicated GC cell lines. CANX, calnexin. (B) Summary of % PRL-3 positivity in urine samples from all cancer patients and normal individuals studied. (C-F) Representative western blots for PRL-3 in the urines of (C) normal individuals and GC patients, (D) nasopharyngeal cancer patients, (E) bladder cancer patients, and (F) lung cancer patients. Mr, relative molecular mass (kDa).

Intracellular PRL-3 Oncoprotein can be Secreted Out and is Present in 62% of Cancer Urines, but not in Normal Urines Having demonstrated the antitumor efficacy of PRL3-zumab in various cancer models, we next sought a simple method to identity PRL-$3^+$ cancer patients for PRL3-zumab therapy. Previously, we reported that anti-PRL-3 antibodies could be internalized by PRL-$3^+$ tumor cells in vitro (23). However, it was unclear how, and where, antibody recognition of "intracellular" PRL-3 antigens occurred. Herein, we report a previously unrecognized natural phenomenon that PRL-3 protein can be secreted and detected in concentrated culture media from corresponding PRL-$3^+$, but not PRL-$3^-$, cancer cell lines in vitro (FIG. 5A, lanes 1-4). To rule out non-specific contamination by dead cells or cellular debris, we detected the ER-localized protein, calnexin (CANX), as a control, exclusively in lysates (FIG. 5A, lanes 5-8) but not in conditioned media (FIG. 5A, lanes 1-4).

Figure 5C:
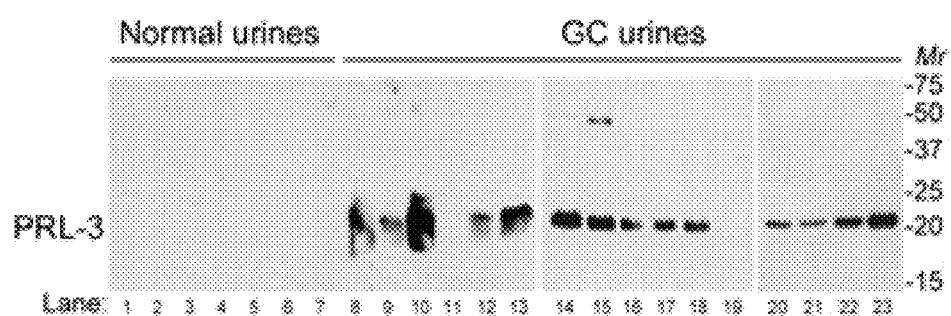
Figure 5D:
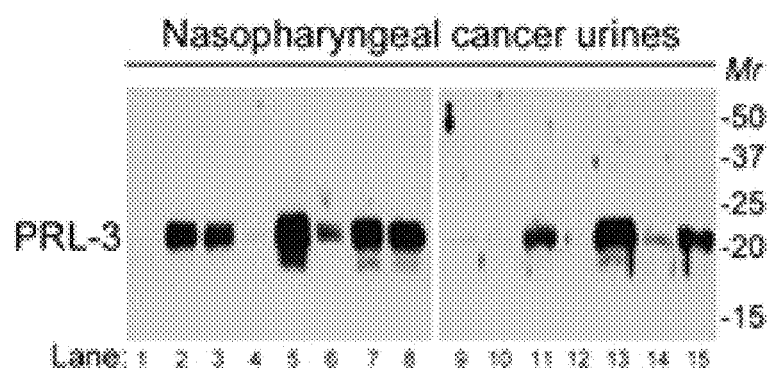
Figure 5E:
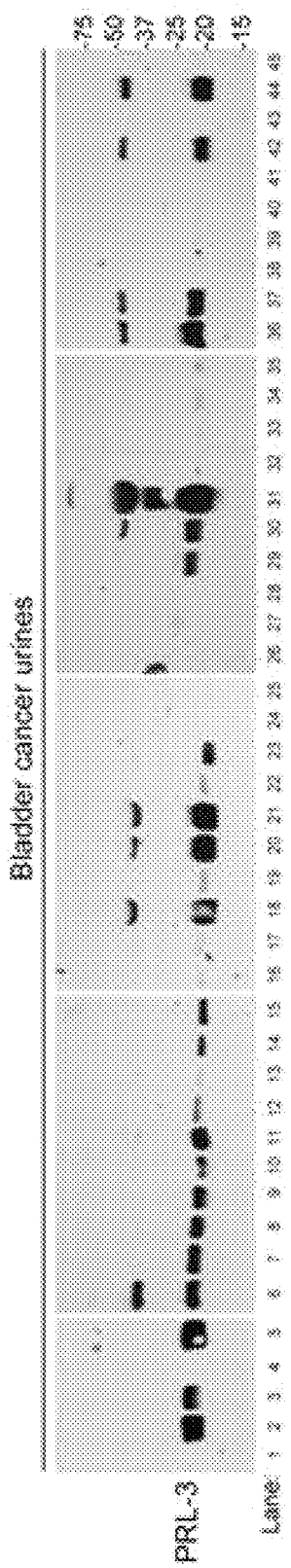
Figure 5F:
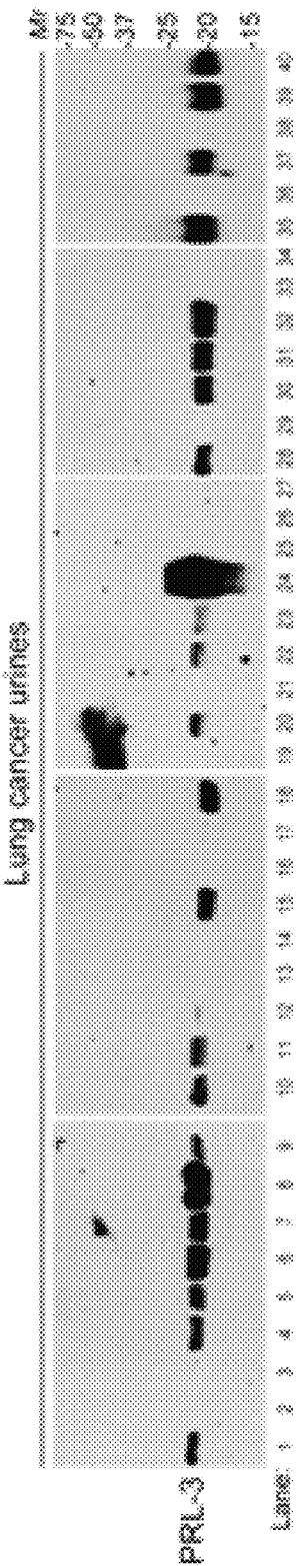

Since PRL-3 has promising cancer biomarker potential based on microarray and histological studies (7), we proceeded to investigate if "secreted" PRL-3 might have clinical relevance as a biomarker by analyzing urine samples from both healthy individuals and cancer patients. A total of 15 urine samples from healthy individuals and 199 urine samples from cancer patients were analyzed by western blot to detect PRL-3 protein. Encouragingly, PRL-3 was readily detected in an average of 62% (123 out of 199) of urine samples from patients with different types of cancer (FIG. 5B), yet completely absent in normal urine samples (FIG. 5C, lanes 1-7). Specifically, urinary PRL-3 protein was detected in up to 14/16 (88%) of gastric cancer patients (FIG. 5C, lanes 8-23), 12/17 (70%) of nasopharyngeal cancer patients (FIG. 5D), 30/67 (45%) of bladder cancer patients (FIG. 5E), 56/85 (66%) of lung cancer patients (FIG. 5F), 8/10 (80%) of breast cancer patients, and 3/4 (75%) of prostate cancer patients (data not shown). Our results from these 214 urine samples identify PRL-3 as a common cancer-specific urinary protein.

Figure 16:
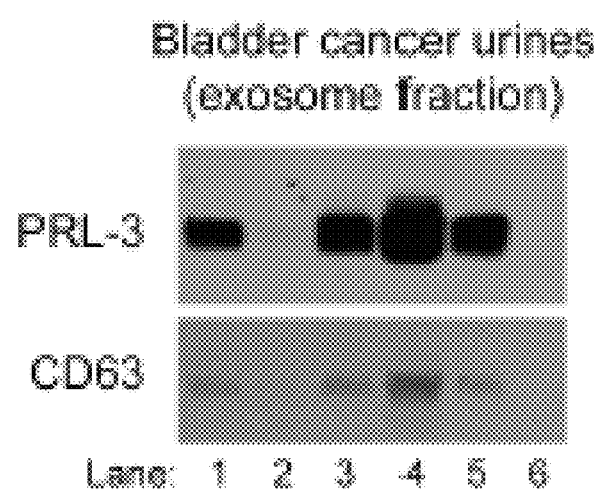
FIG. 16. Exosome-associated PRL-3 is present in the urines of bladder cancer patients. Purified exosome fractions from bladder cancer patient urine samples were analyzed with antibodies against PRL3 CD63 exosome marker.

Since PRL-3 protein does not have a sequence peptide for classical secretion via the ER/Golgi pathway, we considered whether it might be secreted via non-classical exosome secretion. Exosomes are cell-membrane and/or endosomal-derived vesicles between 50 and 150 nm present in many biological fluids and cell culture media (43). We performed exosome fractionation of urine samples from patients with different types of cancer, using tetraspanin CD63 as a control exosomal marker (44). Surprisingly, we detected exosomal PRL-3 exclusively in urine from patients with bladder cancer (FIG. 16), but not from other types of cancers (data not shown). Thus, urinary PRL-3 exists as cancer-specific marker comprising of at least two forms—a soluble, 'free' form (urines from multiple cancer patients), and an exosome-associated form (urines from Bladder cancers patients only).

Figure 6A:
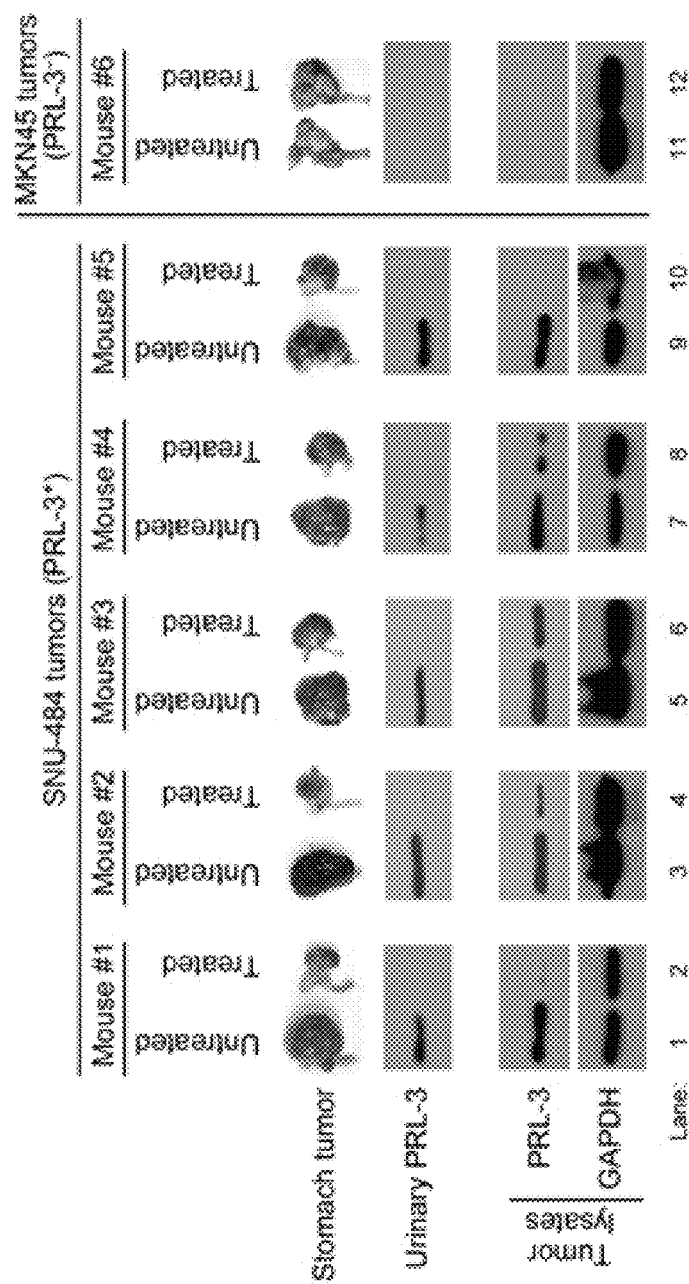
FIG. 6. Effective PRL3-zumab treatment results in a loss of urinary PRL-3, and mechanistically involves intra-tumoral accumulation and recruitment of immune effectors. (A) Western blotting for PRL-3 protein in matched urine and tumor samples from untreated or PRL3-zumab-treated mice harboring PRL-3+ SNU484 or PRL-3− MKN45 orthotopic gastric tumors. Upper panels, excised stomachs at Day 28 (SNU-484) or Day 56 (MKN45). (B) Orthotopic SNU-484 and MKN45 tumor tissue cryo-sections from mice subject to various treatments were analyzed by immunohistochemistry for PRL3-zumab (panels a-f; bar, 20 µm), or immunofluorescence for B cells (panels e-l) and NK cell markers (panels m-r; bar, 50 µm). Green, CD45R/B220 and CD335/Nkp46 staining of B and NK cell markers, respectively; blue, DAPI nuclear stain. (C) Model depicting the proposed mechanism of action of PRL3-zumab on PRL-3+ cancer cells: 1) PRL-3 antigens, externalized via unconventional secretion (exosomal PRL-3), or spontaneous leakage from necrotic PRL-3+ tumor cells (free PRL-3), act as a bait for 2) PRL3-zumab binding and immune complex accumulation within tumor niches, subsequently resulting in 3) recruitment and activation of effector NK and B cells for anti-tumor effects.

Urinary PRL-3 could be a Potential Surrogate Biomarker for Therapeutic Response Monitoring of PRL3-Zumab Therapy Since PRL-3 could be frequently detected in urine samples from cancer patients, we questioned if urinary PRL-3 was reflective of the presence of genuine PRL-$3^+$ tumors in vivo. Due to the difficulty in obtaining clinical matched tumor-urine samples to validate this relationship, we instead used PRL-$3^+$ SNU-484 and PRL-$3^-$ MKN45 orthotopic gastric mouse models to compare the expression of PRL-3 in matched tumor-urine pairs. In addition, each orthotopic model was sub-divided into 2 groups—untreated, or PRL3-zumab (treated)—to elucidate the relationship between PRL3-zumab therapy and urinary PRL-3 expression. In untreated PRL-$3^+$ SNU-484 tumor-bearing mice, PRL-3 protein was highly abundant in urine samples (FIG. 6A, odd lanes 1-9). However, urinary PRL-3 was no longer detectable in all mice after PRL3-zumab treatment, in line with a decrease in intratumoral expression of PRL-3 (FIG. 6A, even lanes 2-10). Importantly, the loss of urinary PRL-3 signal from PRL3-zumab treated mice corresponded with stomach tumor shrinkage in each case (FIG. 6A, upper panels), suggesting that urinary PRL-3 could be useful as a surrogate biomarker of PRL3-zumab therapeutic efficacy. In contrast, we did not detect urinary PRL-3 in mice carrying PRL-$3^-$ MKN45 orthotopic tumors, regardless of PRL3-zumab therapy or not (FIG. 6A, lanes 11-12). Thus, urinary PRL-3 is specifically detected in mice carrying PRL-$3^+$ but not PRL-$3^-$ cancers, and diminishes upon treatment with PRL3-zumab in parallel with reduced tumor burden.

Figure 6B:
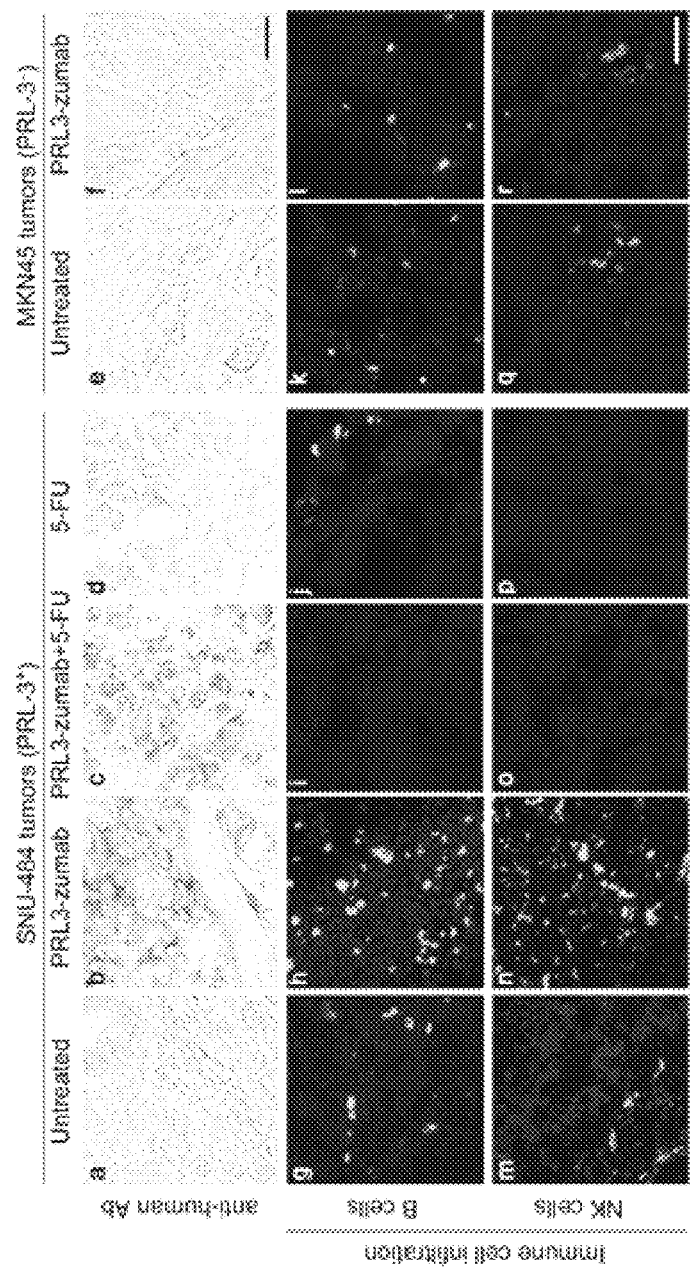

Increased B and NK Cell Infiltration in PRL-3+ Tumors Following PRL3-Zumab Treatment An important consideration in clinical antibody development is the bio-distribution of antibody between tumor and normal (or non-antigen expressing) tissues in vivo (46). In light of this, we explored the distribution of PRL3-zumab at tumor sites in our orthotopic model. Following PRL3-zumab treatment, we detected enrichment of PRL3-zumab within PRL-$3^+$ SNU484 tumors (FIG. 6B, panels b-c) but not in PRL-$3^-$ MKN45 tumors (FIG. 6B, panel f). As a control, no signals were seen in untreated mice (FIG. 6B, panel a) or 5-FU alone (FIG. 6B, panel d). These results indicated a specific accumulation of PRL3-zumab in the microenvironment of PRL-3-expressing tumors. Recognition of antibodies by immune effector cells occurs via immunoglobulin receptors (FcRs), which bind the Fc portion of antibodies, resulting in recruitment and activation of these effector cells (47). To determine whether accumulation of PRL3-zumab in tumor tissues resulted in infiltration of immune cells, immunofluorescence was performed on PRL-3$^+$ SNU-484 gastric tumor sections using specific antibodies against B cells and NK cells, two FcR-bearing immune cell types suggested to be critical for the efficacy of intracellular antibody therapy (26). In PRL-3$^+$ SNU-484 orthotopic tumor sections, compared to untreated tumor sections (FIG. 6B, panels g and m), the numbers of infiltrating B cells and NK cells were visibly higher in PRL3-zumab-treated tumors (FIG. 6B, panels h and n). Strikingly, we consistently observed a lack of B or NK cell infiltration in mice subjected to combination therapy with PRL3-zumab and 5-FU (FIG. 6B, panels i and o) and in 5-FU treated mice (FIG. 6B, panels j and p), likely due to the decrease in lymphocyte population upon 5-FU administration (FIG. 4C). In PRL-3$^-$ MKN45 tumor sections, no differences in B cells or NK cell infiltration was observed, regardless of PRL3-zumab treatment (FIG. 6B, panels k-l and q-r). Based on these findings, we propose a novel mechanism for how PRL3-zumab and PRL-3 antigen might interact to elicit therapeutic effects in vivo (FIG. 6C): 1) PRL-3 antigens, externalized via unconventional secretion (exosomal PRL-3), or spontaneous leakage from necrotic or apoptotic PRL-3$^+$ tumor cells (free PRL-3), act as a bait for 2) PRL3-zumab binding and immune complex accumulation within tumor niches, subsequently resulting in 3) recruitment and activation of effector NK and B cells, for antitumor effects.

Possible Mechanism of Action for PRL3-Zumab Suppression of PRL-3+ Tumors

Studies on autoimmune pathologies have shown that autoantibodies can bind specific intracellular antigens and accumulate within the cytoplasm and nuclear compartments of antigen-expressing cells (47). Likewise, we have observed that anti-PRL-3 antibodies can be internalized by PRL-3+ tumor cells in vitro (4). However, the mode of antibody uptake remains poorly defined. Here, we uncover two new findings by which intracellular PRL-3 antigens might engage antibodies for specific binding and tumor suppression: 1) Intracellular PRL-3 oncoprotein can be secreted out. In tumor cells, several classically "intracellular" proteins have been reported to be externalized via secretion and/or cell surface relocalization, thereby making them accessible to therapeutic intervention using antibodies (48, 49). We investigated if PRL-3 might likewise be externalized as a target antigen for PRL3-zumab binding by comparing PRL-3 intracellular and extracellular PRL-3 expression in three PRL-3+ cell lines: SNU-484, NUGC-4, IM-95, and one PRL-3− cell line, MKN45. PRL-3 expression was compared with the non-secreted, ER-anchored protein, calnexin, as a control. PRL-3 protein was detected both in intracellular protein fractions (cell lysates) of PRL-3+ GC cells (FIG. 6A, lanes 1-3), as well as extracellular protein pools (concentrated conditioned media) of PRL-3+ GC cells (FIG. 6A, lanes 5-7), but not PRL-3− GC cell lines (FIG. 6A, lanes 4, 8). In contrast, calnexin was exclusively present in intracellular pools of both PRL-3+ and PRL-3− PRL GC cells (FIG. 6A, lanes 1-4), but not in extracellular pools (FIG. 6A, lanes 5-8). This observation ruled out non-specific contamination by dead cells or cellular debris, and characterizes PRL-3 as a novel secreted protein. 2) Externalized PRL-3 may serve as bait for PRL3-zumab binding. We next investigated the tumor sections from treated orthotopic GC mice and analyzed the distribution of PRL3-zumab within tumor niche. As a control, no signals were seen in untreated mice (FIG. 6B, leftmost panels). Following treatments, PRL3-zumab was enriched within the microenvironment of PRL-3+ SNU-484 tumors, but not those receiving 5-FU monotherapy, or PRL-3− MKN45 tumors (FIG. 6B). These results indicated a specific accumulation of PRL3-zumab in the microenvironment of PRL-3+ tumors, but not PRL-3− tumors.

Discussion

This study further demonstrates the previously unrecognized potential of tumor-specific intracellular oncoproteins as viable molecular targets for cancer targeted immunotherapies with minimal side-effects. Our results characterized PRL-3 as an excellent tumor-specific oncotarget and demonstrated the specific antitumor efficacy of PRL3-zumab in a clinically relevant setting, using human gastric cancer cell lines to generate orthotopic tumor models. PRL3-zumab specifically inhibited the growth of orthotopic PRL-3$^+$ (but not PRL-3$^-$) gastric tumors, establishing the suitability of PRL3-zumab for treatment of PRL-3$^+$ gastric cancer. In addition, secreted urinary PRL-3 can be used as biomarker for diagnostic and treatment response monitoring.

To create a clinically-relevant orthotopic GC model using human GC cell lines, we employed immunodeficient nude mice but not severely immunocompromised mice strains, such as NOD/SCID, BALB/c-RAG2$^{null}$, or their derivatives (48). These latter strains have little or no endogenous immune system intact, creating a gap in translating research findings to immunocompetent human patients. The use of a more clinically relevant mouse model also overcomes the limitations of in vitro drug screening in culture dishes, which are unable to recapitulate the complex interactions within the body and are poorly predictive of in vivo toxicity (49). Indeed, anti-PRL-3 antibodies have been shown to lack anticancer efficacy in immunocompromised SCID mice (24), or when directly added to PRL-3$^+$ cancer cells in vitro (27), indicating the importance of the interaction of the therapeutic agent with immune effectors for successful treatment. Here, we demonstrated the therapeutic efficacy of PRL3-zumab in inhibiting primary and metastatic gastric tumor growth, as well as its value for postoperative adjuvant therapy to prevent cancer relapse. Furthermore, we extend these findings by demonstrating accumulation of PRL3-zumab and increased infiltration of B and NK cells in PRL-3$^+$ tumor niches upon PRL3-zumab treatment, reinforcing the involvement of these key immune effectors in PRL3-zumab's antitumor activity. PRL-3 was recently shown to promote secretion of ULBP2, an NKG2D ligand, resulting in reduced tumor recognition and cytolysis by NK cells (50). This finding suggests that increased NK cell infiltration into PRL-3$^+$ tumor niches observed in PRL3-zumab-treated mice might be synergistically accompanied by increased NK cytolytic activity, resulting in more efficient immune targeting of PRL-3$^+$ tumors.

Figure 6C:
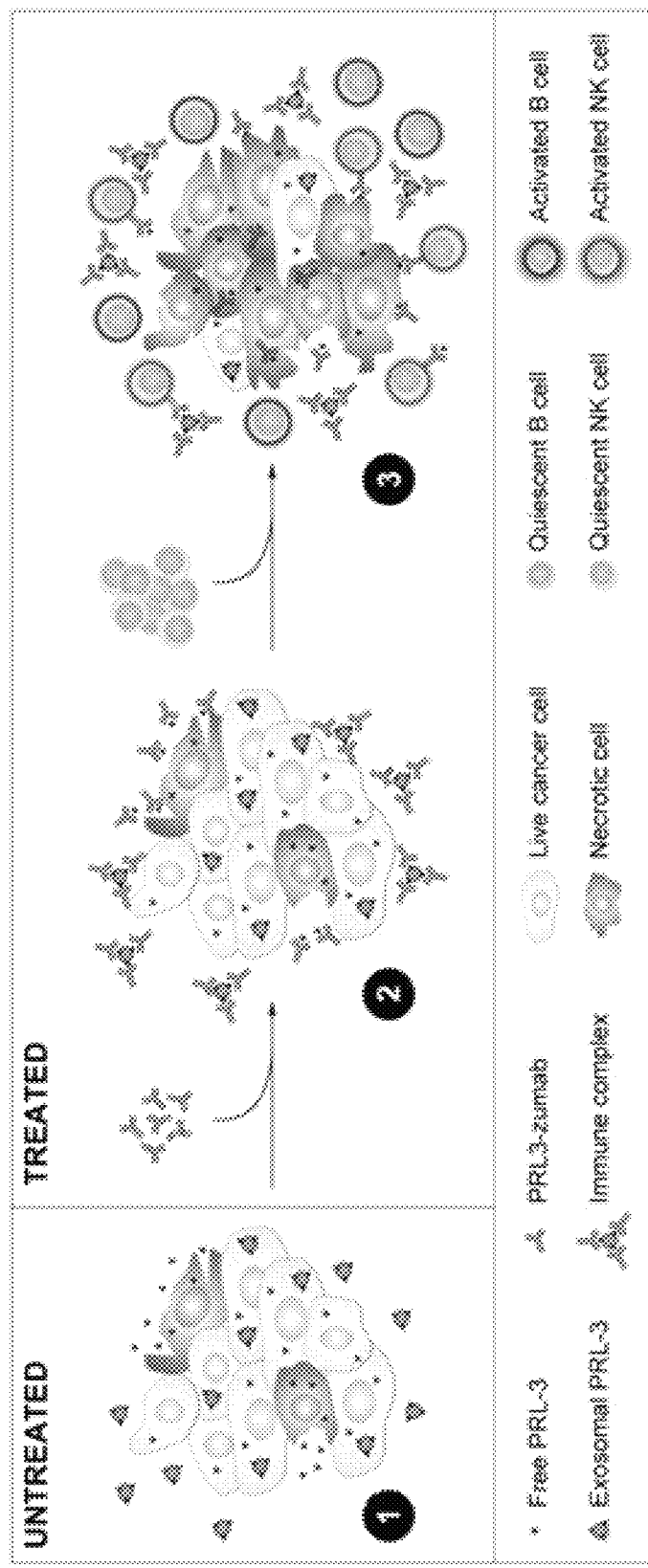

The discovery of PRL-3 in secreted form lends weight to the specific antibody-antigen interaction required for immune cell recruitment to PRL-3$^+$ tumor sites and PRL3-zumab's antitumor efficacy. Interestingly, although soluble PRL-3 was detected in urines from multiple cancer patients, we detected exosome-associated PRL-3 only in the urines of bladder cancer patients, but not in urines from patients with other malignancies. A likely explanation for this is the physical exclusion limit imposed by renal glomerular filtration, which only allows passage of proteins smaller than 70 kDa from the plasma into the Bowman's capsule for urinary excretion (45). Our results indirectly indicate that PRL-3 can be secreted from tumor cells in at least two forms in vivo: 1) Firstly, as a soluble, filterable form present in multiple types of cancer urines. Such 'free PRL-3' may leak out into body fluids during tumor necrosis, apoptosis, or tumor cell lysis, and with its low molecular weight of 20-25 kDa, likely passes through the glomeruli and get excreted in urine. 2) Secondly, as 'exosomal PRL-3', exclusively found in urines of bladder cancer patients since bladder cancer cells with unhindered access to the bladder urinary system could shed such PRL-3-containing exosomes directly into urine pool. However, circulating exosomes from other cancer tissues (such as gastric, liver, lung) cannot pass through glomerular filtration, yet budding exosomes from PRL-3$^+$ cancer cells could serve as anchor points within tumor areas for PRL3-zumab recognition in vivo to initiate for cascade immune response (FIG. 6C).

Recently a large number of FDA-approved cancer drugs were shown to have poor target selectivity (51). In our study, more than 400 clinical cancer samples were studied for expression of PRL-3 at either mRNA level or protein level in tumor tissues and/or cancer urines. On average, PRL-3 oncoprotein was overexpressed in 62% of the multiple types of cancers (gastric, liver, lung, nasopharyngeal, kidney, breast, colon, bladder) examined. With such a high PRL-3 tumor positivity, the development of PRL3-zumab-targeted therapy against tumor-specific PRL-3 is an exciting step towards the personalized medicine. By maximizing therapeutic benefits, whilst minimizing off-target side effects (PRL-3 is not expressed at detectable levels in most normal adult tissues), PRL3-zumab justifies clinical validation and development as a precision anti-cancer drug.

We summarize herein five key findings regarding PRL3-zumab cancer therapy: 1) PRL3-zumab specifically recognizes PRL-3 tumor-specific antigen. PRL3-zumab is highly specific—it does not cross-react with its two homologues (PRL-1 or PRL-2) those share >75% amino acid sequence identity. Furthermore, PRL3-zumab specifically recognizes PRL-3 antigen in tumor tissues but not in normal tissues, suggesting low toxicity and minimal off-target side effects. 2) PRL3-zumab specifically inhibits the growth of PRL-3$^+$ orthotopic gastric tumors and prevents postoperative PRL-3$^+$ tumor relapse. PRL-3 protein expression within tumors is an absolute requirement for a therapeutic response, indicating the necessity for specific antigen-antibody recognition for tumor inhibition. 3) PRL3-zumab is more effective as a monotherapy than in combination with chemotherapy. Collectively, our results indicate that PRL3-zumab treatment outcome depends on the host immune system, as chemotherapy-induced immunosuppression (34) reduces the therapeutic efficacy of PRL3-zumab. 4) PRL3-zumab should have broad utility in multiple PRL-3 positive cancers. Although our results here focus on multiple GC models as a case study for PRL3-zumab efficacy, PRL-3 has also been extensively linked to multiple cancer types of tumor metastasis and poor prognosis, with higher PRL-3 expression associated with shorter overall survival (7). Based on the principle that PRL3-zumab exerts its effects only upon recognizing PRL-3 antigen, it is envisaged to have efficacy in targeting most, if not all, PRL-3-positive cancers in immunologically uncompromised patients, opening a new therapeutic avenue in general cancer therapy. 5) Urinary PRL-3 could be a potential novel biomarker for cancer diagnosis and therapeutic response monitoring. We detected urinary PRL-3 in an average of 62% of multiple human cancer patients. The close correlation between tumor and urinary PRL-3 expression observed in mouse models indicated that urinary PRL-3 expression could have utility as a prospective diagnostic biomarker for PRL-3-targeted cancer therapies (including PRL3-zumab) in a variety of human malignancies. In addition, our data suggests that urinary PRL-3 could possibly function as a surrogate biomarker, providing a fast and simple qualitative method for clinicians to infer PRL3-zumab therapeutic efficacy. Although the biomarker value of urinary PRL-3 will require further validation, the potential for the development of such a 'companion diagnostic' for PRL3-zumab would accelerate its drug development process by allowing for robust hypothesis testing in early clinical trials (52).

Herein, we demonstrate PRL3-zumab as the first humanized antibody against intracellular oncotarget to block PRL-3$^+$ human cancers. Collectively, our results here and elsewhere (23,24,27) challenge the dogma that intracellular oncoantigens are inaccessible to therapeutic antibodies for anti-cancer effects. We suggest other intracellular oncoproteins could also have tremendous potential to serve as targeted immunotherapy A myriad of candidate tumor-specific intracellular oncoantigens should now be reconsidered for their potential as viable molecular targets for future clinical trials.

References

1. D. Hanahan, R. A. Weinberg, Hallmarks of cancer: the next generation. *Cell* 144, 646-674 (2011).
2. J. Ferlay, I. Soerjomataram, R. Dikshit, S. Eser, C. Mathers, M. Rebelo, D. M. Parkin, D. Forman, F. Bray, Cancer incidence and mortality worldwide: sources, methods and major patterns in GLOBOCAN 2012. *Int J Cancer* 136, E359-E386 (2015).
3. S. G. Julien, N. Dubé, S. Hardy, M. L. Tremblay, Inside the human cancer tyrosine phosphatome. *Nat Rev Cancer* 11, 35-49 (2011).
4. Q. Zeng, W. Hong, Y. H. Tan, Mouse PRL-2 and PRL-3, two potentially prenylated protein tyrosine phosphatases homologous to PRL-1. *Biochem Biophys Res Commun* 244, 421-427 (1998).
5. S. Saha, A. Bardelli, P. Buckhaults, V. E. Velculescu, C. Rago, B. S. Croix, K. E. Romans, M. A. Choti, C. Lengauer, K. W. Kinzler, B. Vogelstein, A phosphatase associated with metastasis of colorectal cancer. *Science* 294, 1343-1346 (2001).
6. C. Laurent, F. Valet, N. Planque, L. Silveri, S. Maacha, O. Anezo, P. Hupe, C. Plancher, C. Reyes, B. Albaud, A. Rapinat, D. Gentien, J. Couturier, X. Sastre-Garau, L. Desjardins, J. P. Thiery, S. Roman-Roman, B. Asselain, E. Barillot, S. Piperno-Neumann, S. Saule, High PTP4A3 phosphatase expression correlates with metastatic risk in uveal melanoma patients. *Cancer Res* 71, 666-674 (2011).
7. D. C. Bessette, D. Qiu, C. J. Pallen, PRL PTPs: mediators and markers of cancer progression. *Cancer and Metastasis Reviews* 27, 231-252 (2008).
8. Q. Zeng, X. Si, H. Horstmann, Y. Xu, W. Hong, C. J. Pallen, Prenylation-dependent association of protein-tyrosine phosphatases PRL-1, -2, and -3 with the plasma membrane and the early endosome. *J Biol Chem* 275, 21444-21452 (2000).
9. A. Q. O. Al-Aidaroos, Q. Zeng, PRL-3 phosphatase and cancer metastasis. *J Cell Biochem* 111, 1087-1098 (2010).
10. H. Wang, S. Y. Quah, J. M. Dong, E. Manser, J. P. Tang, Q. Zeng, PRL-3 down-regulates PTEN expression and signals through PI3K to promote epithelial-mesenchymal transition. *Cancer Res* 67, 2922-2926 (2007).

11. A. Q. O. Al-Aidaroos, H. F. Yuen, K. Guo, S. D. Zhang, T. H. Chung, W. J. Chng, Q. Zeng, Metastasis-associated PRL-3 induces EGFR activation and addiction in cancer cells. *J Clin Invest* 123, 3459-3471 (2013).
12. M. W. Zimmerman, K. E. McQueeney, J. S. Isenberg, B. R. Pitt, K. A. Wasserloos, G. E. Homanics, J. S. Lazo, Protein-tyrosine phosphatase 4A3 (PTP4A3) promotes vascular endothelial growth factor signaling and enables endothelial cell motility. *J Biol Chem* 289, 5904-5913 (2014).
13. C. D. Walls, A. Iliuk, Y. Bai, M. Wang, W. A. Tao, Z. Y. Zhang, Phosphatase of Regenerating Liver 3 (PRL3) Provokes a Tyrosine Phosphoproteome to Drive Prometastatic Signal Transduction. *Mol Cell Proteomics* 12, 3759-3777 (2013).
14. U. A. Miskad, S. Semba, H. Kato, H. Yokozaki, Expression of PRL-3 phosphatase in human gastric carcinomas: close correlation with invasion and metastasis. *Pathobiology* 71, 176-184 (2004).
15. Z. R. Li, Z. Wang, B. H. Zhu, Y. L. He, J. S. Peng, S. R. Cai, J. P. Ma, W. H. Zhan, Association of tyrosine PRL-3 phosphatase protein expression with peritoneal metastasis of gastric carcinoma and prognosis. *Surg Today* 37, 646-651 (2007).
16. N. Dai, A. P. Lu, C. C. Shou, J. Y. Li, Expression of phosphatase regenerating liver 3 is an independent prognostic indicator for gastric cancer. *World J Gastroenterol* 15, 1499-1505 (2009).
17. M. Orditura, G. Galizia, V. Sforza, V. Gambardella, A. Fabozzi, M. M. Laterza, F. Andreozzi, J. Ventriglia, B. Savastano, A. Mabilia, E. Lieto, F. Ciardiello, F. De Vita, Treatment of gastric cancer. *World J Gastroenterol* 20, 1635-1649 (2014).
18. J. S. Macdonald, S. R. Smalley, J. Benedetti, S. A. Hundahl, N. C. Estes, G. N. Stemmermann, D. G. Haller, J. A. Ajani, L. L. Gunderson, J. M. Jessup, J. A. Martenson, Chemoradiotherapy after surgery compared with surgery alone for adenocarcinoma of the stomach or gastroesophageal junction. *N Engl J Med* 345, 725-730 (2001).
19. D. Cunningham, W. H. Allum, S. P. Stenning, J. N. Thompson, C. J. H. Van de Velde, M. Nicolson, J. H. Scarffe, F. J. Lofts, S. J. Falk, T. J. Iveson, D. B. Smith, R. E. Langley, M. Verma, S. Weeden, Y. J. Chua, MAGIC Trial Participants, Perioperative chemotherapy versus surgery alone for resectable gastroesophageal cancer. *N Engl J Med* 355, 11-20 (2006).
20. M. Terashima, K. Kitada, A. Ochiai, W. Ichikawa, I. Kurahashi, S. Sakuramoto, H. Katai, T. Sano, H. Imamura, M. Sasako, ACTS-GC Group, Impact of expression of human epidermal growth factor receptors EGFR and ERBB2 on survival in stage II/III gastric cancer. *Clin Cancer Res* 18, 5992-6000 (2012).
21. Y. Y. Janjigian, D. Werner, C. Pauligk, K. Steinmetz, D. P. Kelsen, E. Jager, H. M. Altmannsberger, E. Robinson, L. J. Tafe, L. H. Tang, M. A. Shah, S. E. Al-Batran, Prognosis of metastatic gastric and gastroesophageal junction cancer by HER2 status: a European and USA International collaborative analysis. *Ann Oncol* 23, 2656-2662 (2012).
22. S. Shimoyama, Unraveling trastuzumab and lapatinib inefficiency in gastric cancer: Future steps (Review). *Molecular and clinical oncology* 2, 175-181 (2014).
23. K. Guo, J. P. Tang, C. P. B. Tan, H. Wang, Q. Zeng, Monoclonal antibodies target intracellular PRL phosphatases to inhibit cancer metastases in mice. *Cancer Biol Ther* 7, 750-757 (2008).
24. K. Guo, J. Li, J. P. Tang, C. P. B. Tan, C. W. Hong, A. Q. O. Al-Aidaroos, L. Varghese, C. Huang, Q. Zeng, Targeting intracellular oncoproteins with antibody therapy or vaccination. *Sci Transl Med* 3, 99ra85 (2011).
25. S. Ferrone, Hidden immunotherapy targets challenge dogma. *Science translational medicine* 3, 99ps38 (2011).
26. C. W. Hong, Q. Zeng, Awaiting a new era of cancer immunotherapy. *Cancer Res* 72, 3715-3719 (2012).
27. K. Guo, J. P. Tang, L. Jie, A. Q. O. Al-Aidaroos, C. W. Hong, C. P. B. Tan, J. E. Park, L. Varghese, Z. Feng, J. Zhou, W. J. Chng, Q. Zeng, Engineering the first chimeric antibody in targeting intracellular PRL-3 oncoprotein for cancer therapy in mice. *Oncotarget* 3, 158-171 (2012).
28. C. T. Guy, R. D. Cardiff, W. J. Muller, Induction of mammary tumors by expression of polyomavirus middle T oncogene: a transgenic mouse model for metastatic disease. *Mol Cell Biol* 12, 954-961 (1992).
29. H. Wang, L. A. Vardy, C. P. Tan, J. M. Loo, K. Guo, J. Li, S. G. Lim, J. Zhou, W. J. Chng, S. B. Ng, H. X. Li, Q. Zeng, PCBP1 Suppresses the Translation of Metastasis-Associated PRL-3 Phosphatase. *Cancer Cell* 18, 52-62 (2010).
30. M. W. Zimmerman, G. E. Homanics, J. S. Lazo, Targeted deletion of the metastasis-associated phosphatase Ptp4a3 (PRL-3) suppresses murine colon cancer. *PloS one* 8, e58300 (2013).
31. Z. Wang, Y. L. He, S. R. Cai, W. H. Zhan, Z. R. Li, B. H. Zhu, C. Q. Chen, J. P. Ma, Z. X. Chen, W. Li, L. J. Zhang, Expression and prognostic impact of PRL-3 in lymph node metastasis of gastric cancer: its molecular mechanism was investigated using artificial microRNA interference. *Int J Cancer* 123, 1439-1447 (2008).
32. Z. Wang, S. R. Cai, Y. L. He, W. H. Zhan, C. Q. Chen, J. Cui, W. H. Wu, H. Wu, W. Song, C. H. Zhang, J. J. Peng, X. H. Huang, High expression of PRL-3 can promote growth of gastric cancer and exhibits a poor prognostic impact on patients. *Ann Surg Oncol* 16, 208-219 (2009).
33. C. Wilmanns, D. Fan, C. A. O'Brian, C. D. Bucana, I. J. Fidler, Orthotopic and ectopic organ environments differentially influence the sensitivity of murine colon carcinoma cells to doxorubicin and 5-fluorouracil. *Int J Cancer* 52, 98-104 (1992).
34. L. Rasmussen, A. Arvin, Chemotherapy-induced immunosuppression. *Environ Health Perspect* 43, 21-25 (1982).
35. *BALB/c Nude Mouse Hematology*. Charles River Laboratories International, Inc. (2012)
36. T. Sano, M. Sasako, S. Yamamoto, A. Nashimoto, A. Kurita, M. Hiratsuka, T. Tsujinaka, T. Kinoshita, K. Arai, Y. Yamamura, K. Okajima, Gastric cancer surgery: morbidity and mortality results from a prospective randomized controlled trial comparing D2 and extended para-aortic lymphadenectomy—Japan Clinical Oncology Group study 9501. *J Clin Oncol* 22, 2767-2773 (2004).
37. L. S. Menuck, J. R. Amberg, Metastatic disease involving the stomach. *Am J Dig Dis* 20, 903-913 (1975).
38. L. K. Green, Hematogenous metastases to the stomach. A review of 67 cases. *Cancer* 65, 1596-1600 (1990).
39. Oda, H. Kondo, T. Yamao, D. Saito, H. Ono, T. Gotoda, H. Yamaguchi, S. Yoshida, T. Shimoda, Metastatic tumors to the stomach: analysis of 54 patients diagnosed at endoscopy and 347 autopsy cases. *Endoscopy* 33, 507-510 (2001).
40. T. Saito, T. Iizuka, H. Kato, H. Watanabe, Esophageal carcinoma metastatic to the stomach. A clinicopathologic study of 35 cases. *Cancer* 56, 2235-2241 (1985).

41. G. Gallino, F. Belli, G. Bonfanti, A. Ditto, S. Andreola, G. Tragni, P. P. Massone, E. Civelli, M. Vitellaro, E. Leo, N. Cascinelli, Surgical treatment of gastric metastases from cutaneous melanoma: experience of the National Cancer Institute of Milan. *Tumori* 87, 229-231 (2001).
42. G. Davis, R. Zollinger, Metastatic melanoma of the stomach. *Am* 99, 94-96 (1960).
43. A. V. Vlassov, S. Magdaleno, R. Setterquist, R. Conrad, Exosomes: current knowledge of their composition, biological functions, and diagnostic and therapeutic potentials. *Biochim Biophys Acta* 1820, 940-948 (2012).
44. M. S. Pols, J. Klumperman, Trafficking and function of the tetraspanin CD63. *Exp Cell Res* 315, 1584-1592 (2009).
45. J. P. Caulfield, M. G. Farquhar, The permeability of glomerular capillaries to graded dextrans. Identification of the basement membrane as the primary filtration barrier. *J Cell Biol* 63, 883-903 (1974).
46. A. M. Scott, J. D. Wolchok, L. J. Old, Antibody therapy of cancer. *Nat Rev Cancer* 12, 278-287 (2012).
47. F. Nimmerjahn, J. V. Ravetch, Fc-receptors as regulators of immunity. *Adv Immunol* 96, 179-204 (2007).
48. R. Ito, T. Takahashi, I. Katano, M. Ito, Current advances in humanized mouse models. *Cell Mol Immunol* 9, 208-214 (2012).
49. J. M. McKim, Building a tiered approach to in vitro predictive toxicity screening: a focus on assays with in vivo relevance. *Comb Chem High Throughput Screen* 13, 188-206 (2010).
50. W. H. Leung, Q. P. Vong, W. Lin, D. Bouck, S. Wendt, E. Sullivan, Y. Li, R. Bari, T. Chen, W. Leung, PRL-3 Mediates the Protein Maturation of ULBP2 by Regulating the Tyrosine Phosphorylation of HSP60. *J Immunol* 194, 2930-2941 (2015).
51. C. Rubio-Perez, D. Tamborero, M. P. Schroeder, A. A. Antolin, J. Deu-Pons, C. Perez-Llamas, J. Mestres, A. Gonzalez-Perez, N. Lopez-Bigas, In silico prescription of anticancer drugs to cohorts of 28 tumor types reveals targeting opportunities. *Cancer Cell* 27, 382-396 (2015).
52. J. S. de Bono, A. Ashworth, Translating cancer research into targeted therapeutics. *Nature* 467, 543-549 (2010).
53. J. Li, K. Guo, V. W. C. Koh, J. P. Tang, B. Q. Gan, H. Shi, H. X. Li, Q. Zeng, Generation of PRL-3- and PRL-1-specific monoclonal antibodies as potential diagnostic markers for cancer metastases. *Clin Cancer Res* 11, 2195-2204 (2005).

Example 3: Investigation of PRL3Zumab Mechanism of Action

In this study, we mainly focus on the molecular mechanism of action (MOA) to address how PRL-3 antibody could possible bind to its intracellular PRL-3 antigen using 'seed and soil' Liver orthotopic tumor model. We investigate from different aspects to reach an important conclusion that indeed 'Intracellular oncoprotein' has higher rate in vivo than in vitro to be re-localized to the cell surface as 'Extracellular oncoprotein', thus follow a rational basis for tumor elimination via antibody conventional pathways against Extracellular Oncotargets. Consistently, we mechanistically found that PRL3-zumab blocks tumors expressing PRL-3 'Intracellular' antigen required: 1. host FcγII/III receptor interaction, as both FcγII/III blockers abolished treatment efficacy. 2. full antibody activities, mini-body lacking Fc-fragments (CH1 and Ch2 domains) dismiss treatment efficacy, 3. Increase M1 (but not M2) macrophages, B lymphocytes, natural killer cells to enhance host immunity. These results suggest the MOA of antibody targeting 'Intracellular oncoprotein' is indeed following the similar principles of targeting 'Extracellular Oncoprotein' via classical antibody-dependent cell cytotoxicity (ADCC) or phagocytotic (ADCP) pathways to eliminate tumors. Finally, using 110 precious fresh-frozen human tumors or their matched normal tissues, we further showed that PRL-3 is an excellent tumor-specific oncotarget broadly overexpressed on an average ≥78% from 9 different human cancer types: liver, lung, colon, breast, stomach, bladder, prostate, AML, and kidney patient tumor samples, but not in matched normal tissues. These findings warrant PRL3-zumab clinical trials as the next frontier of targeted immunotherapy for most 'hard-to-treat' cancers.

Materials and Methods

Cell lines. The human HCC cell lines Hep3B2.1, HepG2, Huh-7, PLC, SNU449 were purchased from American Type Cell Culture (Manassas, Va., USA). The murine HCC cell line Hep53.4 was purchased from CLS Cell Lines Service GmbH (Eppelheim, Germany). All cell lines were cultured in their recommended media. The MHCC-LM3 human HCC cancer cell line was routinely maintained in Dr Kam-Man Hui laboratory (National Cancer Center, Singapore).

Western blotting. For patient tissues, a 5 mm3 piece were suspended in RIPA lysis buffer (Sigma) containing a protease-phosphatase inhibitor cocktail (Pierce), and disrupted completely with a tissue homogenizer (Polytron). Lysates were clarified by centrifugation at 13,000×g for 40 min at 4° C. For cell lines, 5×106 cells were lysed in RIPA lysis buffer containing a protease-phosphatase inhibitor and clarified as described above. Tissue lysates (40 µg) or cell lysates (200 µg) were resolved in 12% SDS-polyacrylamide gels and transferred to nitrocellulose membranes before blocking and probing with murine anti-PRL-3 34 or anti-GAPDH antibodies (clone MAB374, Milipore) overnight at 4° C. After thorough washing with TBS-T buffer (20 mM Tris pH 7.6, 140 mM NaCl, 0.2% Tween-20), the membrane was incubated with the respective horseradish peroxidase (HRP)-conjugated secondary antibodies at a 1:5,000 dilution for 1 h, washed with TBS-T buffer, and visualized using a chemiluminescent substrate (Pierce).

Animal models and treatments. Eight-week-old male BALB/c nude mice obtained from the Biological Resource Centre (A*STAR, Singapore) were used for all animal models in this study. Mice were anesthetized with 2.5% avertin (100 µl per 10 g body weight). Abdomens of anesthetized mice were opened in layers by a 1-cm midline incision starting just below the xiphoid sternum. The left lobe of liver was taken out through the abdominal incision and 3×106 MHCC-LM3 liver cancer cells were inoculated into the subcapsular layer. Livers were returned back into the abdominal cavity and abdominal wall sutured back in layers. The treatment regime commenced on Day 5 post-inoculation of cancer cells. For tumor growth/volume experiments, treated mice were administered i.v. bi-weekly, for 5 weeks, with 100 µg each of PRL3-zumab, human IgG isotype control (catalog BE0092; Bio X Cell), or PRL3-minibody. Where indicated, co-treatment was performed by co-administration of 100 ug anti-CD16/32 antibody (clone 2.4G2; Bio X Cell). All antibodies were diluted into 100 µL (final) of PBS for injection. Final tumor volumes were calculated using the formula: volume=0.4×tumor length×tumor width× tumor width. For survival studies, treated mice were administered i.v. with 100 µg of PRL3-zumab diluted in 100 µl PBS twice a week, for a total of 10 times. Untreated mice were administered i.v. with an equivalent volume of placebo (buffer alone) as a control. When mice displayed reduced physical activity and appeared ill, they were euthanized and recorded as a "death" event in survival analysis.

Cell isolation. Tumor cells. Orthotopic MHCC-LM3 liver tumors were harvested and gently dissociated using a MACS tissue dissociation kit (130-095-929; Miltenyi Biotec) according to the manufacturer's instructions. The kit is optimized for high yield of tumor cells, while preserving important cell surface epitopes. Isolated tumor cells were subsequently counted, resuspended in RPMI, and kept on ice till analysis. Cultured cells. MHCC-LM3 PRL-3+ liver cancer cells, exponentially growing at 80% confluence in full RPMI media (RPMI supplemented with 10% FBS and 1% antibiotics) in T-75 flasks, were washed once with PBS and incubated with non-enzymatic cell dissociation buffer (C5914; Sigma) for 5 minutes to dislodge the adherent cells into suspension. Cells were washed once with PBS, counted, resuspended in full RPMI media, and kept on ice till analysis.

Cell surface labeling and flow cytometry analysis. $4 \times 10^5$ cells were incubated with 2 μg of either cetuximab (anti-EGFR, chimeric Ab), herceptin (anti-HER2, humanized Ab), PRL3-zumab (anti-PRL-3, humanized Ab) in a total volume of 100 μl for 30 min at 4° C. A separate tube without any added primary antibody served as a negative control. After incubation, 1 mL PBS was added to each sample, centrifuged, and the cell pellet resuspended in 100 μL PBS containing 1.5 μL anti-human-FITC antibody. After a 15 min incubation at 4° C., the cells were washed with PBS as previously, and finally resuspended in 200 μL PBS. Cells were passed through a cell strainer to obtain single cell suspensions, and immediately acquired on a BD FACSCanto II flow cytometer equipped with 2 lasers (488 nm and 633 nm) using FACS Diva software. Data was stored as FCS3 files and analyzed using Flowing Software version 2.5.1. Live cells were gated based on FSC and SSC. Single cells were gated using FSC and SSC width. Single antibody stained cells (secondary alone) and unstained control cells were used for compensation.

Preparation of recombinant GST-tagged proteins and ELISA. The preparation of recombinant GST-PRL-1, GST-PRL-2, and GST-PRL-3 fusion proteins and ELISA assay have been described previously (59). Briefly, 96-well ELISA plates coated with the indicated antigen amounts were blocked with 3% bovine serum albumin prior to incubation with 0.5 ng or 1 ng of PRL-3 minibody for 2 h at 37° C. After extensive washing and secondary antibody incubation, colorimetric development was performed using a Turbo-TMB substrate (Pierce) and stopped by acidification with 2M $H_2SO_4$. Absorbance was measured at 450 nm using a plate reader (Dynatech).

Immunofluorescence imaging. Fresh-frozen specimens of MHCC orthotopic liver tumors were sectioned into 10 μm slices using a cryostat (Leica) at 16° C. The slides were fixed with 4% paraformaldehyde for 20 min, washed with PBS-0.05% Tween-20, and blocked in PBS-FDB (PBS pH 7.0, 2% BSA, 5% goat serum, 5% fetal bovine serum) for 1 h at RT. Slides were subsequently incubated with the indicated primary antibodies at a 1:200 dilution 4° C. overnight, washed, and incubated for 2 h with the corresponding fluorochrome-conjugated secondary antibodies (Life Technologies). Washed slides were mounted with a DAPI-containing anti-fade mounting reagent (Vector Laboratories) and sealed using nail polish. Confocal imaging was performed with an LSM 800 confocal microscope (Zeiss AG). Representative images (n=3) of tumor infiltrating lymphocytes (TILs) in the tumor area adjacent to tumor capsule (junction of normal and tumor tissue) were taken. Total numbers of immune cells (green) and DAPI positive cells (blue) were analysed by Image J software, and the percentage of TILs determined by taking the ratio of immune cells to DAPI. Averaging the result of 3 images represents the data of 1 sample.

Results

PRL-3 'Intracellular Oncoprotein' can be Identified as 'Extracellular Oncoprotein' In Vivo.

Figure 20A:
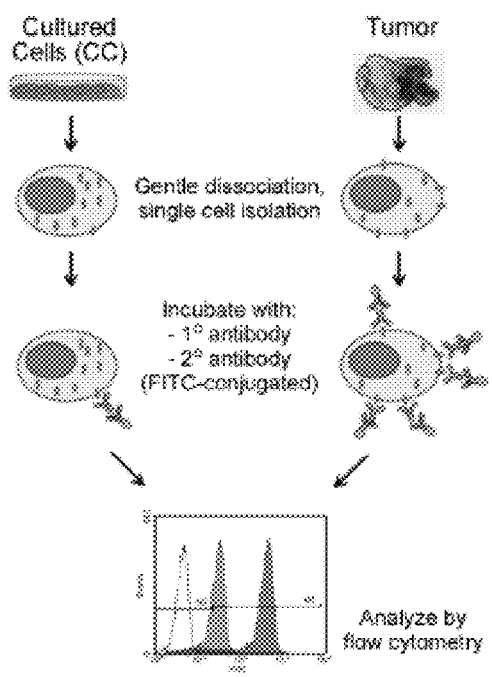
FIG. 20. PRL-3 is highly upregulated on the surface of tumor cells in vivo, but not cultured cancer cells in vitro. (a) Experimental outline for cytometry analysis of cell-surface profiles of in vitro cultured cells and ex vivo tumor cells. (b) Representative histograms of cell-surface staining with control (clear), PRL3-zumab (pink), or cetuximab (CTX; grey) antibodies. The positive gate (% pos) was determined after subtracting background signals inferred from control staining. (c) % cell-surface positive population for different antibodies tested as in (b). Data representing mean±SEM. (d) Western blot for EGFR and PRL-3, showing altered levels of the proteins in cultured cells versus tumors. GAPDH, loading control.
Figure 20B:
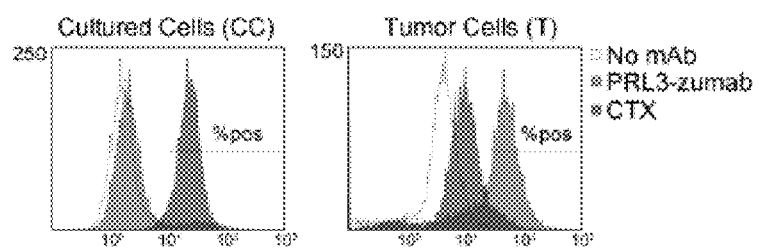
Figure 20C:
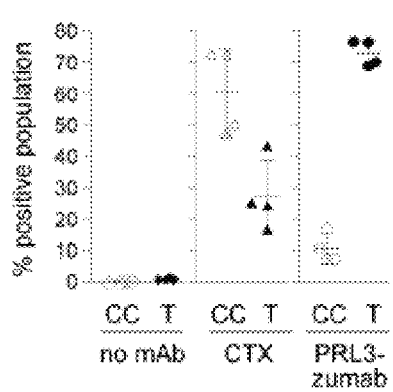
Figure 20D:
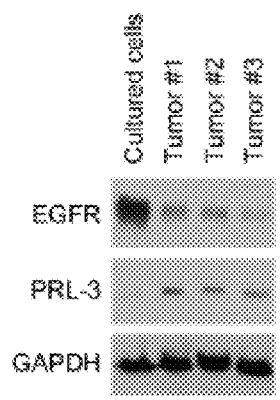
Figure 22D:
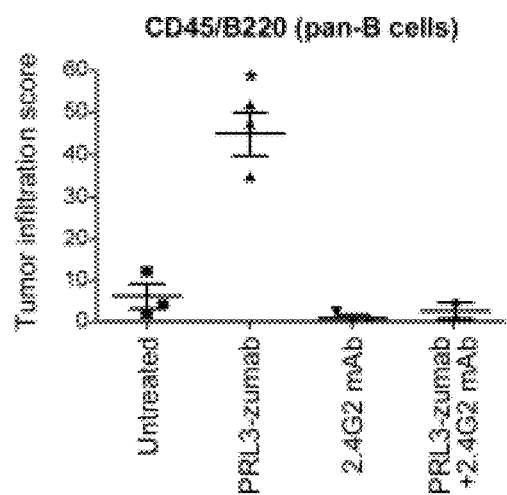
FIG. 22: Interactions with host FcγII/III receptors are essential for PRL3-zumab-induced recruitment of NK cells, B cells, and M1 macrophages into the tumor niche. Orthotopic MHCC-LM3 liver tumor tissue cryo-sections from mice subject to various treatments were analyzed by immunofluorescence with antibodies against (a) F4/80 (pan-macrophage), (b) CD206 (M2 macrophages), (c) CD86 (M1 macrophages), (d) CD45/B220 (B cells), or (e) CD335 (NK cells). Tumor infiltration scores were calculated as described in Materials and Methods. *p<0.05, one-way ANOVA; data representing mean±SEM.
Figure 22E:
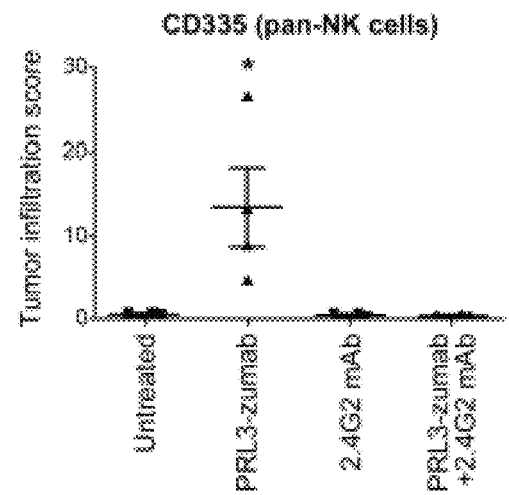

PRL-3 antibodies have shown efficacy against PRL-3-expressing xenograft tumors, metastatic lung tumors, and orthotopic gastric tumors. To understand these unconventional antibody therapies against an Intracellular oncoprotein, how could PRL3-antibody bridge intracellular PRL-3 with FcγR on immune cells? A possible hypothesis is that some portion of PRL-3 itself might be flipped over to expose at the cell surface in vivo to trigger cycling effects, thereby permitting direct PRL3-zumab binding, like other cell surface (extracellular) antigens. To test this, we prepared single cell suspensions from solid liver tumors using gentle enzymatic dissociation, and compared the cell surface expression of these ex vivo tumor cells versus in vitro cultured cells using a flow cytometry approach (FIG. 20a). Cytometric analysis of these un-permeabilized cell pools revealed major antigen-specific differences between them. Cetuximab, an anti-epidermal growth factor receptor (EGFR) chimeric antibody, showed dramatically lower surface expression of EGFR in ex vivo tumors compared to cultured cells where high amount of growth factors were artificially added into, whereas the reverse was true for PRL-3 (representative flow histograms in FIG. 20b). Quantification revealed a 3-fold reduction decrease in surface EGFR staining in ex vivo tumor cells (T) relative to cultured cells (CC; FIG. 20c, columns 3 vs 4). In contrast, PRL-3 expression, as analysed with PRL3-zumab staining, increased approximately 7-fold in ex vivo tumor cells where In vivo, cancer cells are under hypoxic stress and serum deprivation, conditions that might enhance the abilities of cancer cells to externalize intracellular PRL-3 proteins compared to cultured cells condition (CC; FIG. 20c, columns 5 vs 6). To validate if these changes seen in flow cytometry might be due to changes in total cellular levels of these antigens, we performed Western blotting of lysates in parallel. In agreement with the earlier cytometric observation, compared to cultured cells, total levels of EGFR were notably downregulated in ex vivo tumor cells (FIG. 20d). In contrast, PRL-3 expression clearly increased in tumors relative to original cells (FIG. 20d). However, since the increase in total PRL-3 levels was much smaller compared to the increase in PRL-3 surface levels, we reason that the latter observation might be mainly attributed to a re-localization of intracellular PRL-3. To validate this, transmission electron microscopy (TEM) of cultured MHCC cells and MHCC tumors was performed, where a marked increase in anti-PRL-3 immunogold staining on the extracellular leaflet of the cell membrane in MHCC tumors compared to MHCC cells was observed, without a significant difference on the intracellular leaflet of the cell membrane.

PRL3-Zumab Displays Therapeutic Efficacy in an Fc-Dependent Manner in 'Seed & Soil' Orthotopic Liver Tumor Models in Mice These higher levels of 'extracellular' PRL-3 antigens in vivo could then be recognized by PRL-3 antibody to recruit immunocytes and to follow classical ADCC and ADCP of antibody therapeutics against traditional extracellular oncoproteins. Orthotopic tumor models, wherein human cancer cells ("seeds") are allowed to grow in their natural locations ("soils"), replicate human disease with high fidelity. We recently reported that PRL3-zumab could suppress PRL-3-expressing orthotopic Gastric tumors formed by human gastric cancer cells (8). Additionally, we showed that PRL3-zumab could also block PRL-3-expressing tumor relapse after resection.

In this study, to better recapitulate clinically-relevant therapeutic HCC therapeutic responses 16, we established an orthotopic HCC model to test the ability for PRL3-zumab to suppress Liver tumors within their natural niche (FIG. 21a). In a panel of six human (1 mouse?) liver cancer cell lines screened for PRL-3 protein expression status (FIG. 21b), only PRL-3+ MHCC-LM3 cells robustly formed liver tumors within a reasonable timeframe (6 weeks), and were selected for subsequent treatment experiments. Similar to orthotopic gastric tumors 6, orthotopic liver tumor formation was visibly reduced in PRL3-zumab-treated mice compared to untreated mice (FIG. 21c). Measurement of tumor volume revealed a significant, 7-fold reduction in mean tumor burden in treated mice compared to untreated mice (FIG. 21d; 0.30±0.36 vs 2.41±1.20 cm3, P=0.0001). To study if treatment would have longer-term effects on mice survival, we treated mice with PRL3-zumab for four weeks, stopped treatment, and monitored the time taken till appearance of morbid characteristics ("death" event). Following this treatment schedule, treated mice had a significantly longer overall survival compared to untreated mice, with a median survival time of 12 weeks versus 8 weeks, respectively (FIG. 21e; Kaplan-Meier survival analysis, P=0.002). Collectively, our findings established that PRL3-zumab retained therapeutic efficacy in this clinically-relevant HCC model, with significant tumor burden reduction and longer survival.

Figure 24:
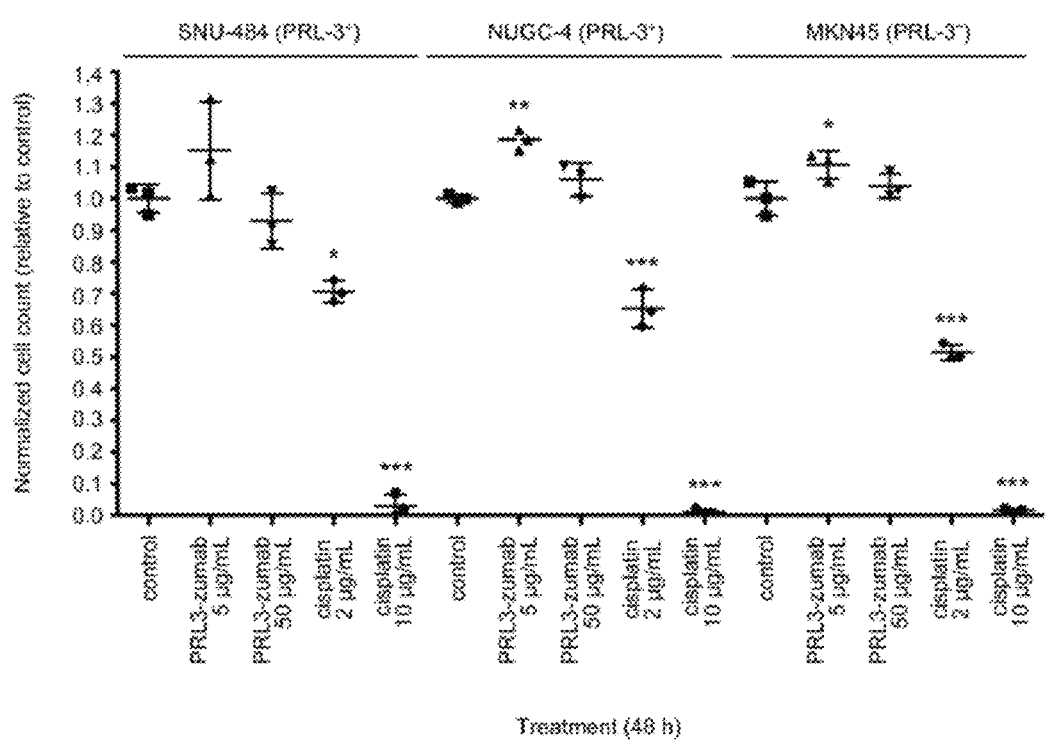
FIG. 24: in vitro assays analysing if PRL3-zumab could directly inhibit PRL-3+ cancer cells.
Figure 25:
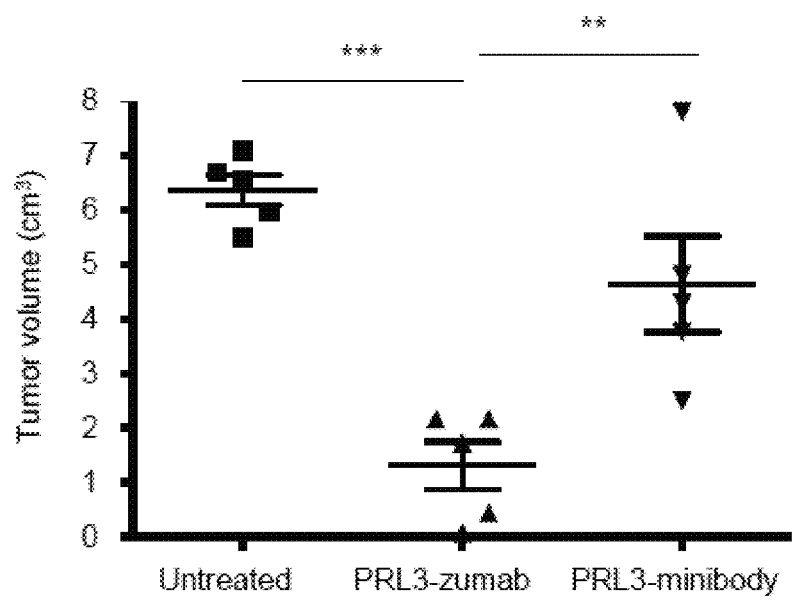
FIG. 25: Efficacy of the (scFv-CH3)2 PRL3-minibody was against orthotopic PRL-3+ SNU-484 gastric tumors.

To understand the molecular mechanism(s) involved, we first performed in vitro assays to analyse if PRL3-zumab could directly inhibit PRL-3+ cancer cells. Despite profound suppression of PRL-3+ tumors in vivo, PRL3-zumab treatment did not inhibit PRL-3+ nor PRL-3− cancer cell growth in vitro, even at high doses of 50 mg/mL (FIG. 24). In contrast, cisplatin treatment resulted in a dose-dependent, nonspecific cell killing of both PRL-3+ and PRL-3− cells (FIG. 24). This finding re-affirmed that PRL3-zumab, like other therapeutic antibodies, required specific host factors for anti-tumor effects 15. In conventional antibody therapy, Fc receptors (FcR) on immune cells bind to the constant (Fc) region of antigen-antibody complexes, resulting in their recruitment and activation of effector pathways for target antigen/cell clearance via antibody-dependent cell-mediated cytotoxicity (ADCC) or phagocytosis (ADCP) 17. To investigate the involvement of host FcRs in PRL3-zumab's mechanism of action, we designed 2 complementary experiments (FIG. 21f), namely 1) co-treatment of mice inoculated with PRL-3+ orthotopic liver tumors with PRL3-zumab and anti-CD16/32 antibody (2.4G2 mAb), a potent inhibitor of IgG FcR-mediated immune clearance by blocking the binding site of FcγII and FcγIII receptors 18, and 2) substitution of intact PRL3-zumab with an engineered (scFv-CH3)2 PRL3-minibody lacking the CH1 and CH2 domains shown to be essential for binding to Fc receptors 19,20. Upon blockage of FcγII/III receptors using the 2.4G2 mAb, there was a complete loss of PRL3-zumab treatment efficacy, resulting in mean tumor volumes without significant difference from untreated, 2.4G2 mAb, or isotype-matched control (IgG)-treated mice (FIG. 21g). Likewise, liver tumors treated with (scFv-CH3)2 PRL3-minibody were also devoid of therapeutic response (FIG. 21g). Notably, a similar lack in therapeutic efficacy of the (scFv-CH3)2 PRL3-minibody was also evident against orthotopic PRL-3+ SNU-484 gastric tumors (FIG. 25), illustrating that this was not a tissue-specific defect. Furthermore, deletion of PRL3-zumab's CH1 and CH2 domains did not affect the resulting minibody's binding to PRL-3, as evidenced by Western blotting, ELISA, and immunofluorescence (data not shown), indicating that the loss of therapeutic effect was not due to potential antigen binding defects from antibody miniaturization. Taken together, our results establish that the interaction between the Fc domain of PRL3-zumab and host FcγII/III receptors are essential for anti-tumor effects of PRL3-zumab.

PRL3-Zumab Recruits B Lymphocytes, Natural Killer Cells, and M1 Macrophage to PRL-3-Expressing Tumor Niches for Cancer Cells Killing In Vivo Fc-FcR interactions are important in tumor cell clearance via ADCC and ADCP. Whereas NK cells are the major effectors of ADCC, macrophages are the effectors of ADCP, the latter being increasingly recognized as the major mechanism of action behind most antibodies approved to treat cancer 21. Tumor-associated macrophages (TAMs) are an important element of the tumor stoma which can play dynamic, opposing roles during tumorigenesis, varying between immune-stimulatory and tumoricidal activities (M1 macrophages) to immuno-suppression and pro-metastatic activities (M2 macrophages) 22. To determine whether PRL3-zumab promoted the infiltration and accumulation of macrophages and other immune cells within the tumor niche, immunofluorescence was performed on PRL-3+ MHCC liver tumor sections using various antibodies specific to different macrophage subtypes: M1 macrophages (CD86), pan-macrophage (F4180); M2 macrophages (CD206), B cells (CD45/B220), and NK cells (CD335). Interestingly, a significant increase in CD86+ M1 macrophages was evident (FIG. 21c; F(5,12)=7.127, p<0.0053), whereas no significant differences were observed between group means for accumulation of F4/80+ macrophages and CD206+ M2 macrophages (FIGS. 2a,b). Similarly, a significant accumulation in B cells (FIG. 21d; F(5,12)=40.14, P<0.001) and NK cells (FIG. 21e; F(5,12)=7.386, P<0.0046) across all treatment groups was also observed. Remarkably, combination therapy with PRL3-zumab and 2.4G2 mAb resulted in a reversal in this PRL3-zumab induced accumulation (FIGS. 2c-e), establishing that PRL3-zumab promoted the specific accumulation of these cells in an FcR-dependent manner. Taken together, our results establish that interaction between the Fc domain of PRL3-zumab and FcγII/III receptors was essential for recruitment of tumoricidal M1 macrophages, B cells, and NK cells, and that these correlated closely with anti-tumor efficacy in vivo (FIG. 21f).

Figure 23A:
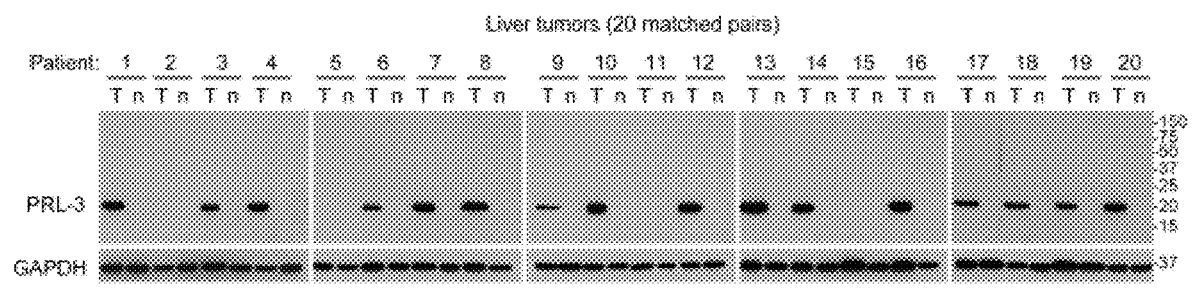
FIG. 23: PRL-3 is a general oncotarget frequently overexpressed in multiple human tumors. (a-e) Full western blot analysis of PRL-3 in tumor (T) versus patient-matched normal tissues (n) pairs of (a) liver tumors, (b) lung tumors, (c) colon tumors, (d) breast tumors, and (e) kidney tumors. (f-j) Full western blot analysis of (f) kidney tumors, (g) bladder tumors, (h) acute myeloid leukemia (AML), (i) stomach tumors, and (j) prostate tumors in additional patient samples without matched normal tissues. GAPDH, loading control. Relative molecular masses (in kDa) are indicated on the right of each result set.
Figure 23B:
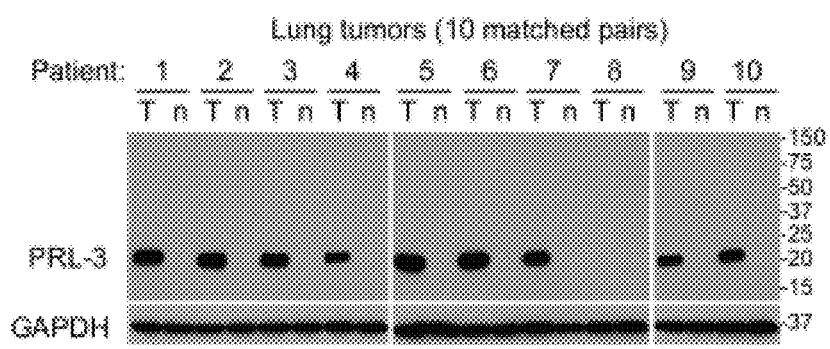
Figure 23C:
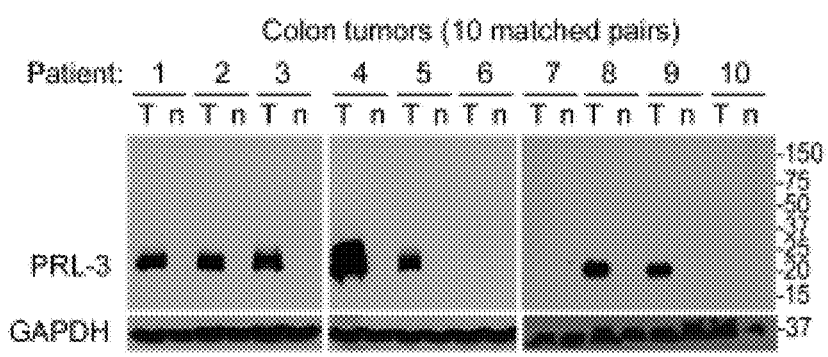
Figure 23D:
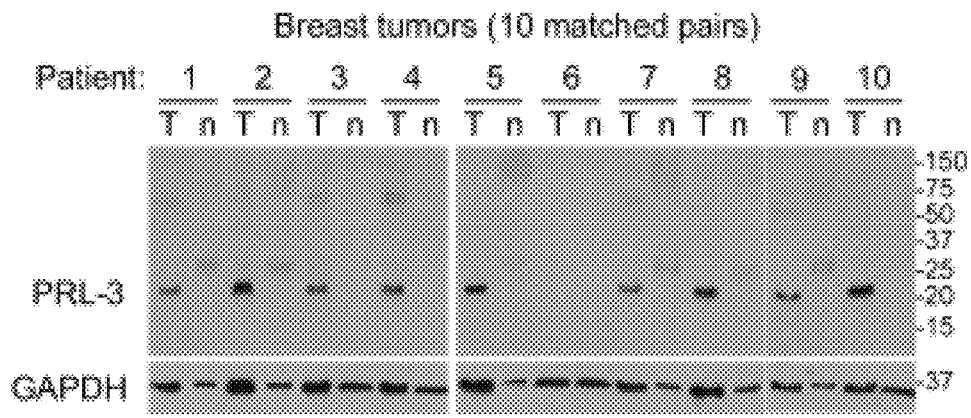
Figure 23E:
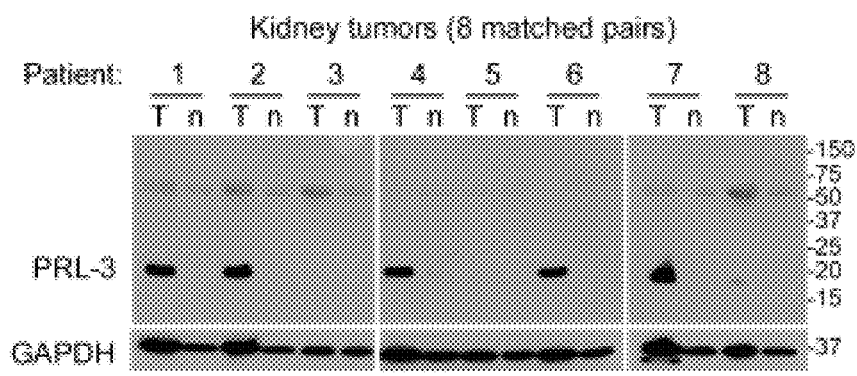
Figure 23F:
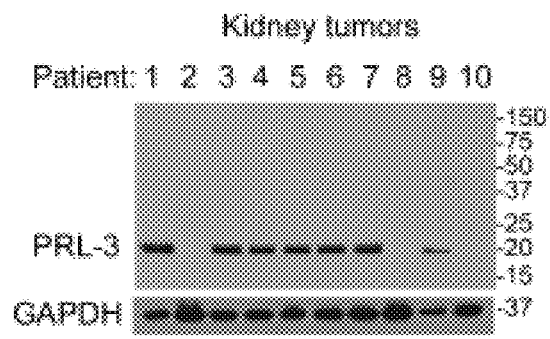
Figure 23G:
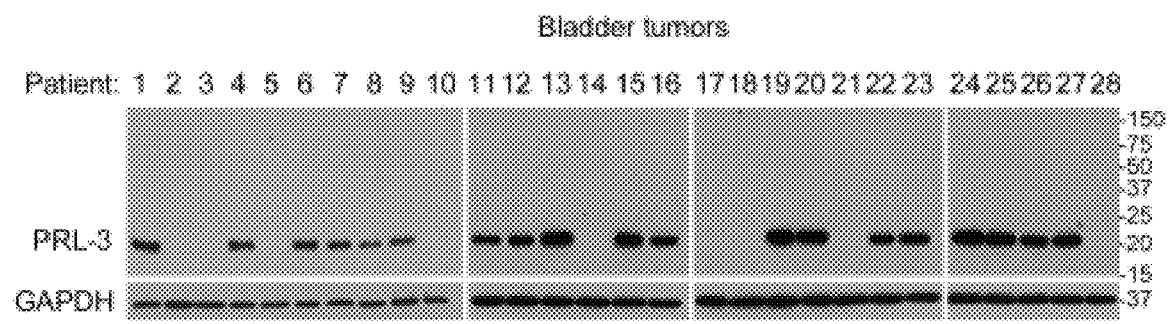

PRL-3, a Novel Oncotarget, is Frequently Overexpressed in Multiple Human Cancers; PRL3-Zumab Will Serve for Urgent Unmet Medical Needs to Treat these Multiple PRL-3 Positive Human Cancers We previously demonstrated the value of PRL-3 as a novel gastric cancer oncotarget, where PRL-3 expression was detected in 85% of fresh frozen gastric tumor tissues, but not in patient-matched normal gastric tissues 6. Since elevated PRL-3 transcript expression has been described in many other tumor types 2, we sought to broadly characterize PRL-3 protein expression in hard-to-obtain 110 fresh-frozen patient tumor samples from 9 different cancer types, particularly aggressive malignancies with unmet medical needs. In these randomly-allocated fresh-frozen samples from our clinical collaborators, we detected robust PRL-3 expression in 16/20 liver tumors (80%; FIG. 23a), 9/10 lung tumors (90%; FIG. 23b), 7/10 colon tumors (70%; FIG. 23c), 9/10 breast tumors (90%; FIG. 23d), 13/18 kidney tumors (72%; FIGS. 23e,f), 19/28 bladder tumors (68%; FIG. 23g), 6/12

Figure 23H:
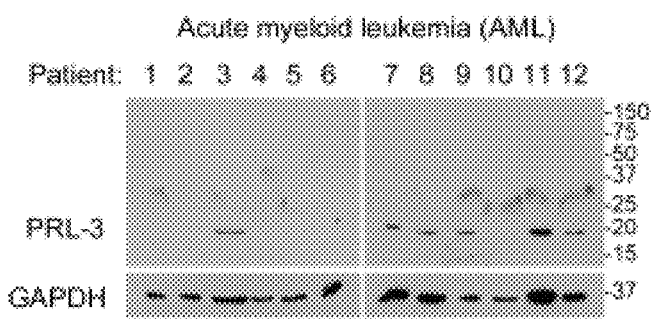
Figures 23I, 23J:
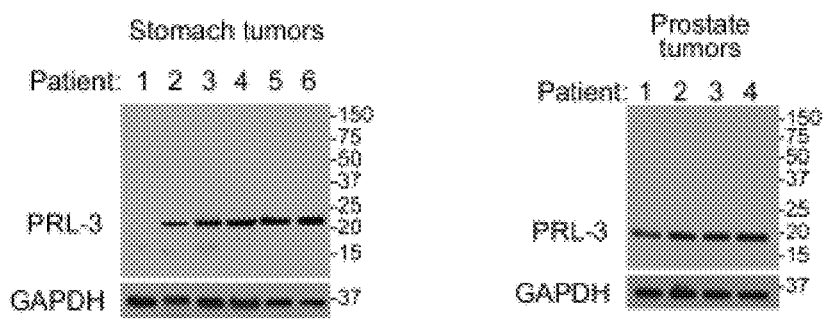

AML samples (50%; FIG. 23h), 5/6 stomach tumors (83%; FIG. 23i), and 4/4 prostate tumors (100%; FIG. 23j). For liver, lung, colon, breast and kidney tumors, we managed to obtain fresh-frozen, patient-matched non-cancerous tissues from the same organs, which allowed precious insight into the specificity of PRL-3 expression. Remarkably, PRL-3 was not detected in any of the matched normal tissues, despite high expression in corresponding matched tumors (FIGS. 4a-e). In summary, these results demonstrate that PRL-3 is a broad, tumor-associated oncotarget expressed on average ≥78% in a variety of 9 tumor types (Table 1), and highlights PRL-3 as an excellent oncotarget in multiple cancer types, particularly those with urgent, unmet medical needs. PRL3-zumab will serve as an urgent need for novel cancer therapy.

TABLE 1

Summary of PRL3 expression across different tumor types
No. of patient samples

| Tumor type | PRL-3+ | PRL-3− | Total | % PRL-3+ |
|---|---|---|---|---|
| Liver | 16 | 4 | 20 | 80 |
| Lung | 9 | 1 | 10 | 90 |
| Colon | 7 | 3 | 10 | 70 |
| Breast | 9 | 1 | 10 | 90 |
| Stomach | 5 | 1 | 6 | 83 |
| Bladder | 19 | 9 | 28 | 68 |
| Prostate | 4 | 0 | 4 | 100 |
| AML | 6 | 6 | 12 | 50 |
| Kidney | 7 | 3 | 10 | 70 |

Discussion

This study builds on our previous work, providing conclusive evidence on the molecular of action to further dissect how possible antibody could target 'Intracellular oncoprotein' and the future therapeutic value of PRL3-zumab against multiple PRL-3-positive human cancer types. Our finding of PRL-3 is a tumor-associated oncotarget present at >78% frequency in 110 randomly-analyzed fresh-frozen human cancer samples, and having demonstrated the significant therapeutic benefit of PRL3-zumab in orthotopic liver and lung tumors in this and previous study on orthotopic stomach tumor models (ref.), we again demonstrate PRL3-zumab as a breakthrough immunotherapy candidate for these acute malignancies with urgent, unmet medical needs, in addition to other cancers in general.

The pathophysiologic complexity of HCC, which includes underlying functional liver insufficiency, has made medical treatment of HCC challenging. The recurrence of HCC, post-transplant, also remains a clinically relevant problem. Previous efforts to identify specific molecular changes involved in HCC progression have yielded few practical hits, particularly due to the diverse etiology of HCC: more than 90% of HCC develops from cirrhosis, which in turn is caused by diverse factors including alcoholism, infection with hepatitis B or C, or the build-up of fat in the liver. Testament to the heterogeneity of HCC, at least five major Phase III trials of novel, molecular-targeted agents against advanced liver cancer have failed in the past six years 32. Sorafenib was the original therapy that demonstrated an improvement in mortality for advanced HCC with extended median survival of 2.8 months 12. Yet, treatment of sorafenib in patients with advanced HCC and liver dysfunction (Child-Pugh B patients) resulted in worse survival outcomes 33. Thus, there is a pressing need to discover novel molecularly-targeted drugs with both high therapeutic efficacy and low toxicity for HCC patients. Here, PRL-3 overexpression was detected in 80% of randomly-analyzed liver cancer patient samples, providing the first clinical evidence that PRL-3 protein could be a common marker of this morbid disease. Notably, as most major human organs lack PRL-3 protein expression 6, PRL3-zumab has been proven to be well-tolerated in nonhuman primate toxicology studies, with a high no-observed-adverse-event-level (NOAEL) dose of 36 mg/kg (unpublished observations). The anti-tumor efficacy of PRL3-zumab in orthotopic mouse models reported here lends strong support for commencing early trials for PRL3-zumab in PRL-3+ HCC patients as a safe, effective treatment modality.

To address how antibodies could recognize Intracellular oncoproteins, previously, we provided three possible models on the mechanism of action (MOA), including antibodies can be uptake by the cancer cells. (CBT, 2008). In this study, we consolidated the MOA by providing evidences on how an 'intracellular oncoprotein' can be externalized to be 'extracellular oncoprotein', thus, following classical pathways of cancer cells killing effects, a mechanistic explanation for the safe and efficient anti-tumor effects of PRL3-zumab, underpinned by the specific and consistent upregulation of PRL-3 in tumors but not normal tissues. Indeed, cell-surface relocalization of tumor-associated intracellular antigens provides novel opportunities for therapeutic intervention. Inflamentry, tumor necrosis, tumor cell killing lysates, apoptosis, may also contribute to intracellular proteins to leak into tumor microenvironments and trigger immune responses in vivo. Besides PRL-3, tumor-associated, in fact, cell-surface relocation of other intracellular proteins have also been described heat-shock protein 70 (HSP70), heat-shock protein 90 (HSP90), glucose-regulated protein 78 (GRP78), actin, cytokeratins, vimentin, nucleolin, nucleosomes, estrogen receptor-alpha variant 36 (ER-a36), and feto-acinar pancreatic protein (FAPP) (5). Since considerable efforts have been invested in identifying new antigen targets that are suitable for antibody-based therapies in cancer, our results here reaffirm that cell-surface relocalization of classically "intracellular" cytosolic and nuclear proteins during malignant progression might be a common tumor-specific phenomenon worth more attention, and form a basis for increasingly innovative and rational drug design to reduce cancer morbidity and mortality.

We understand the challenges to reflect an in vivo tumor cell killing event in cell culture system where artificial conditions limited cell types, in 10% FBS culture media, impossible to mimic in vivo complexity. We realize drugs that kill cancer cells in dishes likely due to drugs' own toxicities. Nevertheless, we show that despite PRL3-zumab treatment of PRL-3+ cancer cells in vitro did not result in any suppression of cell growth, tumors derived from these cells could be potently suppressed by PRL3-zumab in vivo.

Our findings herein provide two explanations for this phenomenon. Firstly, amount of 'extracellular PRL-3' is insignificant in culture system to perform ADCC in vitro, but get highly upregulated on tumor cells to levels sufficient to trigger PRL3-zumab-mediated cancer cell killing effects. Secondly, unlike in vivo systems, in vitro systems fail to recapitulate the complex host factors essential for induction of immune-mediated tumor cell killing by PRL3-zumab.

These results provide sound evidence that the in vivo environment plays an important part in influencing the druggability of target proteins and their therapeutic responses, a phenomenon which could be overlooked in assays based on simplified culture conditions. In this vein, we found that Fc-host FcγR interactions were essential for anti-tumor effects of PRL3-zumab, blockage of FcγR in host cells resulted in a complete loss of PRL3-zumab anti-tumor effects, concomitant with reduced infiltration of B cells, NK cells and M1 macrophages which are important to participate in ADCC and ADCP. Macrophages are one of the major populations of tumour-infiltrating immune cells, and are generally advantageous for tumor growth and metastasis. This is primarily because macrophage-polarizing events during tumour progression promote tumor escape by inducing a differentiation from an M1 to an M2 phenotype, as observed in advanced cancers. M1 cells have high microbicidal activity, immuno-stimulatory functions and tumour cytotoxicity. Recent meta-analysis studies have identified a significant correlation between increased tumoricidal M1 infiltration and favourable survival in lung 23 and gastric 24 cancer patients. Importantly, PRL3-zumab treatment resulted in a specific increase in M1, but not M2, macrophage accumulation. Whether this reflects a reversal in M1/M2 polarization towards an anti-tumor phenotype, or the specific promotion of M1 macrophage recruitment, requires further study. Interestingly, this enhancement of M1 tumoricidal activity by PRL3-zumab ranks it alongside other cutting-edge TAM-targeted anti-tumor strategies, such as targeting the NF-kB and STAT1 pathways, as well as treatment with cytokines (e.g. GM-CSF, IFN-g, IL-12) to promote M1 TAM polarization 25. Besides M1 macrophages, PRL3-zumab also promoted the infiltration of NK cells and B cells, and anti-tumor effects, in an FcγR-dependent manner. Whereas NK cells are well-known as major effectors of ADCC, little is known about the functional role of B cells in the anti-tumor response. Previously, we implicated an anti-tumor role for B cells when we found that anti-PRL-3 mAbs failed to suppress PRL-3+ tumors in genetically engineered mice strains (muMT mice) deficient in B cell maturation and activation. Studies have shown that tumor-associated B cells can contribute to cancer immunosurveillance and suppress metastasis. Higher infiltration of B cells into primary human breast and ovarian tumors have been found to correlate with better prognosis. Chemotherapy has been shown to promote anti-tumor B cell activation and intratumoral accumulation, in a manner correlating with better anti-tumor response. Conversely, B cell depletion impairs T-cell-dependent anti-tumor cytotoxic responses and promotes tumor growth. Interestingly, in a retrospective analysis of lymphoma patients receiving high-dose chemotherapy with subsequent autologous transplantation, it was noted that depletion of B cells during a high-dose chemotherapy regimen resulted in a significantly higher incidence of solid tumors. Taken together, we hypothesize that B cells play important, but under-recognized roles in mechanistic efficacy of general anti-tumor therapy, The important evidences of Fc function of antibodies and Fc-receptors, together with key immunocytes recruitments in this study, we propose that the mechanism of action of PRL3-zumab mainly involves binding cell surface PRL-3, followed by anti-tumor clearance via classical ADCC or ADCP, akin to other receptor-targeting antibodies such as trastuzumab and rituximab. Our unconventional antibody targets 'Intracellular Oncoprotein' warrants further study on a large intracellular treasure of potential cancer-specific therapeutic targets tapped with antibody therapies since both 'infra-cellular and extra-cellular oncoproteins' follow immune-mediated tumour cell killing through ADCC and/or ADCP. Our pioneer novel cancer treatments will await a new era of cancer immunotherapies to benefit cancer patients soon.

References For Example 2

1. Lazo J S, Sharlow E R. Drugging Undruggable Molecular Cancer Targets. Annu Rev Pharmacol Toxicol. 2016; 56:23-40.
2. Guzińska-Ustymowicz K, Pryczynicz A. PRL-3, an emerging marker of carcinogenesis, is strongly associated with poor prognosis. Anticancer Agents Med Chem. 2011; 11(1):99-108.
3. Al-Aidaroos A Q O, Zeng Q. PRL-3 phosphatase and cancer metastasis. J Cell Biochem. 2010; 111(5):1087-98.
4. Guo K, Tang J P, Tan C P B, Wang H, Zeng Q. Monoclonal antibodies target intracellular PRL phosphatases to inhibit cancer metastases in mice. Cancer Biol Ther. 2008; 7(5): 750-7.
5. Guo K, Tang J P, Jie L, Al-Aidaroos A Q O, Hong C W, Tan C P B et al. Engineering the first chimeric antibody in targeting intracellular PRL-3 oncoprotein for cancer therapy in mice. Oncotarget. 2012; 3(2):158-71.
6. Thura M, Al-Aidaroos A Q O, Yong W P, Kono K, Gupta A, Lin Y B et al. PRL3-zumab, a first-in-class humanized antibody for cancer therapy. JCI insight. 2016; 1(9): e87607.
7. Guo K, Li J, Tang J P, Tan C P B, Hong C W, Al-Aidaroos A Q O et al. Targeting intracellular oncoproteins with antibody therapy or vaccination. Science translational medicine. 2011; 3(99):99ra85.
8. Wang Y, Wang X, Ferrone C R, Schwab J H, Ferrone S. Intracellular antigens as targets for antibody based immunotherapy of malignant diseases. Molecular oncology. 2015; 9(10):1982-93.
9. Hong C W, Zeng Q. Awaiting a new era of cancer immunotherapy. Cancer Res. 2012; 72(15):3715-9.
10. Ferlay J, Soerjomataram I, Ervik M, Dikshit R, Eser S, Mathers C et al. GLOBOCAN 2012 v1.1, Cancer Incidence and Mortality Worldwide: IARC CancerBase No. 11 [Internet]. 2014 [cited 31 Mar. 2017]. Available from: globocan.iarc.fr
11. Raza A, Sood G K. Hepatocellular carcinoma review: current treatment, and evidence-based medicine. World journal of gastroenterology. 2014; 20(15):4115-27.
12. Bruix J, Raoul J L, Sherman M, Mazzaferro V, Bolondi L, Craxi A et al. Efficacy and safety of sorafenib in patients with advanced hepatocellular carcinoma: subanalyses of a phase III trial. J Hepatol. 2012; 57(4):821-9.
13. Zhao W B, Li Y, Liu X, Zhang L Y, Wang X. Evaluation of PRL-3 expression, and its correlation with angiogenesis and invasion in hepatocellular carcinoma. Int J Mol Med. 2008; 22(2):187-92.
14. Xu Y, Zhu M, Zhang S, Liu H, Li T, Qin C. Expression and prognostic value of PRL-3 in human intrahepatic cholangiocarcinoma. Pathol Oncol Res. 2010; 16(2):169-75.
15. Hong C W, Zeng Q. Tapping the treasure of intracellular oncotargets with immunotherapy. FEBS Lett. 2014; 588 (2):350-5.
16. He L, Tian D A, Li P Y, He X X. Mouse models of liver cancer: Progress and recommendations. Oncotarget. 2015; 6(27):23306-22.
17. Nimmerjahn F, Ravetch J V. Fc-receptors as regulators of immunity. Adv Immunol. 2007; 96:179-204.
18. Kurlander R J, Ellison D M, Hall J. The blockade of Fc receptor-mediated clearance of immune complexes in vivo by a monoclonal antibody (2.4G2) directed against Fc receptors on murine leukocytes. J Immunol. 1984; 133(2):855-62.

19. Canfield S M, Morrison S L. The binding affinity of human IgG for its high affinity Fc receptor is determined by multiple amino acids in the CH2 domain and is modulated by the hinge region. J Exp Med. 1991; 173(6):1483-91.
20. Greenwood J, Clark M, Waldmann H. Structural motifs involved in human IgG antibody effector functions. Eur J Immunol. 1993; 23(5):1098-104.
21. Weiskopf K, Weissman I L. Macrophages are critical effectors of antibody therapies for cancer. mAbs. 2015; 7(2):303-10.
22. Mills C D. M1 and M2 Macrophages: Oracles of Health and Disease. Crit Rev Immunol. 2012; 32(6):463-88.
23. Wu P, Wu D, Zhao L, Huang L, Chen G, Shen G et al. Inverse role of distinct subsets and distribution of macrophage in lung cancer prognosis: a meta-analysis. Oncotarget. 2016; 7(26):40451-60.
24. Wang X L, Jiang J T, Wu C P. Prognostic significance of tumor-associated macrophage infiltration in gastric cancer: a meta-analysis. Genet Mol Res. 2016; 15(4)
25. Tang X, Mo C, Wang Y, Wei D, Xiao H. Anti-tumour strategies aiming to target tumour-associated macrophages. Immunology. 2013; 138(2):93-104.
26. Wang W, Erbe A K, Hank J A, Morris Z S, Sondel P M. NK Cell-Mediated Antibody-Dependent Cellular Cytotoxicity in Cancer Immunotherapy. Frontiers in immunology. 2015; 6:368.
27. DiLillo D J, Yanaba K, Tedder T F. B cells are required for optimal CD4+ and CD8+ T cell tumor immunity: therapeutic B cell depletion enhances B16 melanoma growth in mice. J Immunol. 2010; 184(7):4006-16.
28. Quan N, Zhang Z, Demetrikopoulos M K, Kitson R P, Chambers W H, Goldfarb R H et al. Evidence for involvement of B lymphocytes in the surveillance of lung metastasis in the rat. Cancer Res. 1999; 59(5):1080-9.
29. Martinet L, Garrido I, Filleron T, Le Guellec S, Bellard E, Fournie J J et al. Human solid tumors contain high endothelial venues: association with T- and B-lymphocyte infiltration and favorable prognosis in breast cancer. Cancer Res. 2011; 71(17):5678-87.
30. Montfort A, Pearce O, Maniati E, Vincent B G, Bixby L, Böhm S et al. A Strong B-cell Response Is Part of the Immune Landscape in Human High-Grade Serous Ovarian Metastases. Clin Cancer Res. 2017; 23(1):250-62.
31. Tarella C, Passera R, Magni M, Benedetti F, Rossi A, Gueli A et al. Risk factors for the development of secondary malignancy after high-dose chemotherapy and autograft, with or without rituximab: a 20-year retrospective follow-up study in patients with lymphoma. J Clin Oncol. 2011; 29(7):814-24.
32. Scudellari M. Drug development: try and try again. Nature. 2014; 516(7529):54-6.
33. DA Fonseca L G, Barroso-Sousa R, Bento A D S A, Blanco B P, Valente G L, Pfiffer T E F et al. Safety and efficacy of sorafenib in patients with Child-Pugh B advanced hepatocellular carcinoma. Molecular and clinical oncology. 2015; 3(4):793-6.
34. Li J, Guo K, Koh V W C, Tang J P, Gan B Q, Shi H et al. Generation of PRL-3- and PRL-1-specific monoclonal antibodies as potential diagnostic markers for cancer metastases. Clin Cancer Res. 2005; 11(6):2195-204.

The invention claimed is:

1. An antibody or antigen binding fragment thereof that binds PRL3, having at least one light chain variable region comprising the following CDRS:

```
                                            (SEQ ID NO: 4)
        LC-CDR1: KASQSVEDDGENYMN, (SEQ ID NO: 5)
        LC-CDR2: AASNLES,
        and (SEQ ID NO: 6)
        LC-CDR3: QQSNEDPFT;
``` and at least one heavy chain variable region comprising the following CDRs:

```
                                            (SEQ ID NO: 1)
        HC-CDR1: GYTFTNYYMH, (SEQ ID NO: 2)
        HC-CDR2: WIYPGNVNTYYNEKFRG,
        and (SEQ ID NO: 3)
        HC-CDR3: EEKNYPWFAY.
```

2. The antibody or antigen binding fragment thereof of claim 1, wherein the antibody or antigen binding fragment thereof contains a CH1 and a CH2 domain.

3. The antibody or antigen binding fragment thereof of claim 1, wherein the antibody or antigen binding fragment thereof comprises: a heavy chain variable region sequence selected from the group consisting of SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; and SEQ ID NO: 25; and a light chain variable region sequence selected from the group consisting of SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; and SEQ ID NO: 15.

4. A method of treating cancer in a patient with a cancer that expresses PRL3, comprising administering the antibody or antigen binding fragment thereof according to claim 1 to said patient.

5. The method according to claim 4 wherein the cancer is gastric cancer or metastatic gastric cancer.

6. The method according to claim 4 wherein the antibody or antigen binding fragment thereof is administered intravenously.

7. The method according to claim 4 wherein the antibody or antigen binding fragment thereof is administered at a location distant to the cancer to be treated.

8. The method according to claim 4 wherein the method comprises administering the antibody or antigen binding fragment thereof to a patient with gastric cancer, wherein the patient has not previously received antimetabolite therapy.

9. The method according to claim 8 wherein the antimetabolite therapy is 5-fluorouracil.

10. The method according to claim 4 wherein the patient has been determined not to have an impaired immune system.

11. The antibody or antigen binding fragment thereof of claim 1, which is a humanized antibody or antigen binding fragment thereof.

12. The method according to claim 4 wherein the cancer is nasopharyngeal cancer, bladder cancer, lung cancer, breast cancer, kidney cancer, liver cancer, prostate cancer, acute myeloid leukemia, colon cancer or ovarian cancer.

* * * * *

SEQUENCE LISTING

```
<160> NUMBER OF SEQ ID NOS: 77

<210> SEQ ID NO 1
<211> LENGTH: 10
<212> TYPE: PRT
<213> ORGANISM: Artificial Sequence
<220> FEATURE:
<223> OTHER INFORMATION: HC-CDR1

<400> SEQUENCE: 1

Gly Tyr Thr Phe Thr Asn Tyr Tyr Met His
1               5                   10

<210> SEQ ID NO 2
<211> LENGTH: 17
<212> TYPE: PRT
<213> ORGANISM: Artificial Sequence
<220> FEATURE:
<223> OTHER INFORMATION: HC-CDR2

<400> SEQUENCE: 2

Trp Ile Tyr Pro Gly Asn Val Asn Thr Tyr Tyr Asn Glu Lys Phe Arg
1               5                   10                  15

Gly

<210> SEQ ID NO 3
<211> LENGTH: 10
<212> TYPE: PRT
<213> ORGANISM: Artificial Sequence
<220> FEATURE:
<223> OTHER INFORMATION: HC-CDR3

<400> SEQUENCE: 3
```

```
Glu Glu Lys Asn Tyr Pro Trp Phe Ala Tyr
1               5                  10

<210> SEQ ID NO 4
<211> LENGTH: 15
<212> TYPE: PRT
<213> ORGANISM: Artificial Sequence
<220> FEATURE:
<223> OTHER INFORMATION: LC-CDR1

<400> SEQUENCE: 4

Lys Ala Ser Gln Ser Val Glu Asp Asp Gly Glu Asn Tyr Met Asn
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: LC-CDR2

<400> SEQUENCE: 5

Ala Ala Ser Asn Leu Glu Ser
1               5

<210> SEQ ID NO 6
<211> LENGTH: 9
<212> TYPE: PRT
<213> ORGANISM: Artificial Sequence
<220> FEATURE:
<223> OTHER INFORMATION: LC-CDR3

<400> SEQUENCE: 6

Gln Gln Ser Asn Glu Asp Pro Phe Thr
1               5

<210> SEQ ID NO 7
<211> LENGTH: 108
<212> TYPE: PRT
<213> ORGANISM: Artificial Sequence
<220> FEATURE:
<223> OTHER INFORMATION: Humanized light chain protein HZD_K1

<400> SEQUENCE: 7

Asp Thr Gln Leu Thr Gln Ser Pro Ser Ser Leu Ser Ala Ser Val Gly
1               5                   10                  15

Asp Arg Val Thr Ile Cys Lys Ala Ser Gln Ser Val Glu Asp Asp Gly
            20                  25                  30

Glu Asn Tyr Met Asn Trp Tyr Gln Gln Lys Pro Gly Ser Pro Lys Leu
        35                  40                  45

Leu Ile Tyr Ala Ala Ser Asn Leu Glu Ser Gly Ile Pro Ala Arg Phe
    50                  55                  60

Ser Gly Ser Gly Ser Gly Thr Asp Phe Thr Leu Thr Ile Ser Ser Leu
65                  70                  75                  80

Pro Glu Asp Phe Ala Thr Tyr Tyr Cys Gln Gln Ser Asn Glu Asp Pro
                85                  90                  95

Phe Thr Phe Gly Ser Gly Thr Lys Leu Glu Ile Lys
            100                 105

<210> SEQ ID NO 8
<211> LENGTH: 108
<212> TYPE: PRT
<213> ORGANISM: Artificial Sequence
<220> FEATURE:
```

<223> OTHER INFORMATION: Humanized light chain protein HZD_K2

<400> SEQUENCE: 8

Asp Thr Gln Leu Thr Gln Ser Pro Ser Ser Leu Ser Ala Ser Val Gly
1               5                   10                  15

Asp Arg Val Thr Ile Cys Lys Ala Ser Gln Ser Val Glu Asp Asp Gly
            20                  25                  30

Glu Asn Tyr Met Asn Trp Tyr Gln Gln Lys Pro Gly Ser Pro Lys Leu
        35                  40                  45

Leu Ile Tyr Ala Ala Ser Asn Leu Glu Ser Gly Ile Pro Ala Arg Phe
    50                  55                  60

Ser Gly Ser Gly Ser Gly Thr Asp Phe Thr Leu Thr Ile Ser Ser Leu
65                  70                  75                  80

Pro Glu Asp Phe Ala Thr Tyr Tyr Cys Gln Gln Ser Asn Glu Asp Pro
                85                  90                  95

Phe Thr Phe Gly Gln Gly Thr Lys Leu Glu Ile Lys
            100                 105

<210> SEQ ID NO 9
<211> LENGTH: 108
<212> TYPE: PRT
<213> ORGANISM: Artificial Sequence
<220> FEATURE:
<223> OTHER INFORMATION: Humanized light chain protein HZD_K3

<400> SEQUENCE: 9

Asp Thr Gln Leu Thr Gln Ser Pro Ser Ser Leu Ser Ala Ser Val Gly
1               5                   10                  15

Asp Arg Val Thr Ile Cys Lys Ala Ser Gln Ser Val Glu Asp Asp Gly
            20                  25                  30

Glu Asn Tyr Met Asn Trp Tyr Gln Gln Lys Pro Gly Ser Pro Lys Leu
        35                  40                  45

Leu Ile Tyr Ala Ala Ser Asn Leu Glu Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Pro Glu Asp Phe Ala Thr Tyr Tyr Cys Gln Gln Ser Asn Glu Asp Pro
                85                  90                  95

Phe Thr Phe Gly Gln Gly Thr Lys Leu Glu Ile Lys
            100                 105

<210> SEQ ID NO 10
<211> LENGTH: 108
<212> TYPE: PRT
<213> ORGANISM: Artificial Sequence
<220> FEATURE:
<223> OTHER INFORMATION: Humanized light chain protein HZD_K4

<400> SEQUENCE: 10

Asp Thr Gln Leu Thr Gln Ser Pro Ser Ser Leu Ser Ala Ser Val Gly
1               5                   10                  15

Asp Arg Val Thr Ile Cys Lys Ala Ser Gln Ser Val Glu Asp Asp Gly
            20                  25                  30

Glu Asn Tyr Met Asn Trp Tyr Gln Gln Lys Pro Gly Ser Pro Lys Leu
        35                  40                  45

Leu Ile Tyr Ala Ala Ser Asn Leu Glu Ser Gly Ile Pro Ser Arg Phe
    50                  55                  60

Ser Gly Ser Gly Ser Gly Thr Asp Phe Thr Leu Thr Ile Ser Ser Leu

```
                65                  70                  75                  80
Pro Glu Asp Phe Ala Thr Tyr Tyr Cys Gln Gln Ser Asn Glu Asp Pro
                        85                  90                  95

Phe Thr Phe Gly Pro Gly Thr Lys Val Asp Ile Lys
                100                 105

<210> SEQ ID NO 11
<211> LENGTH: 108
<212> TYPE: PRT
<213> ORGANISM: Artificial Sequence
<220> FEATURE:
<223> OTHER INFORMATION: Humanized light chain protein HZD_K5

<400> SEQUENCE: 11

Asp Thr Gln Leu Thr Gln Ser Pro Ser Ser Leu Ser Ala Ser Val Gly
1               5                   10                  15

Asp Arg Val Thr Ile Cys Lys Ala Ser Gln Ser Val Glu Asp Asp Gly
                20                  25                  30

Glu Asn Tyr Met Asn Trp Tyr Gln Gln Lys Pro Gly Ser Pro Lys Leu
            35                  40                  45

Leu Ile Tyr Ala Ala Ser Asn Leu Glu Ser Gly Ile Pro Ser Arg Phe
        50                  55                  60

Ser Gly Ser Gly Ser Gly Thr Asp Phe Thr Leu Thr Ile Ser Ser Leu
65                  70                  75                  80

Pro Glu Asp Phe Ala Thr Tyr Tyr Cys Gln Gln Ser Asn Glu Asp Pro
                85                  90                  95

Phe Thr Phe Gly Pro Gly Thr Lys Val Asp Ile Lys
                100                 105

<210> SEQ ID NO 12
<211> LENGTH: 108
<212> TYPE: PRT
<213> ORGANISM: Artificial Sequence
<220> FEATURE:
<223> OTHER INFORMATION: Humanized light chain protein HZD_K6

<400> SEQUENCE: 12

Asp Thr Val Leu Thr Gln Ser Pro Ser Ser Leu Ser Ala Ser Val Gly
1               5                   10                  15

Asp Arg Val Thr Ile Cys Lys Ala Ser Gln Ser Val Glu Asp Asp Gly
                20                  25                  30

Glu Asn Tyr Met Asn Trp Tyr Gln Gln Lys Pro Gly Ser Pro Lys Leu
            35                  40                  45

Leu Ile Tyr Ala Ala Ser Asn Leu Glu Ser Gly Ile Pro Ser Arg Phe
        50                  55                  60

Ser Gly Ser Gly Ser Gly Thr Asp Phe Thr Leu Thr Ile Ser Ser Leu
65                  70                  75                  80

Pro Glu Asp Phe Ala Thr Tyr Tyr Cys Gln Gln Ser Asn Glu Asp Pro
                85                  90                  95

Phe Thr Phe Gly Pro Gly Thr Lys Val Asp Ile Lys
                100                 105

<210> SEQ ID NO 13
<211> LENGTH: 113
<212> TYPE: PRT
<213> ORGANISM: Artificial Sequence
<220> FEATURE:
<223> OTHER INFORMATION: Humanized light chain protein K

<400> SEQUENCE: 13
```

Asp Ile Gln Met Thr Gln Ser Pro Ser Ser Leu Ser Ala Ser Val Gly
1               5                   10                  15

Asp Arg Val Thr Ile Ser Cys Lys Ala Ser Gln Ser Val Glu Asp Asp
            20                  25                  30

Gly Glu Asn Tyr Met Asn Trp Tyr Gln Gln Lys Pro Gly Lys Ser Pro
            35                  40                  45

Lys Leu Leu Ile Tyr Ala Ala Ser Asn Leu Glu Ser Gly Ile Pro Ala
        50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Phe Thr Phe Gly Ser Gly Thr Lys Leu Gly Ile Lys Arg
            100                 105                 110

Thr

<210> SEQ ID NO 14
<211> LENGTH: 113
<212> TYPE: PRT
<213> ORGANISM: Artificial Sequence
<220> FEATURE:
<223> OTHER INFORMATION: Humanized light chain protein L1

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Glu Asp Asp
            20                  25                  30

Gly Glu Asn Tyr Met Asn Trp Tyr Gln Gln Lys Pro Gly Lys Ala Pro
            35                  40                  45

Lys Leu Leu Ile Tyr Ala Ala Ser Asn Leu Glu Ser Gly Val Pro Ser
        50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Phe Thr Phe Gly Pro Gly Thr Lys Val Asp Ile Lys Arg
            100                 105                 110

Thr

<210> SEQ ID NO 15
<211> LENGTH: 113
<212> TYPE: PRT
<213> ORGANISM: Artificial Sequence
<220> FEATURE:
<223> OTHER INFORMATION: Humanized light chain protein L2

<400> SEQUENCE: 15

Asp Thr Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Glu Asp Asp
            20                  25                  30

Gly Glu Asn Tyr Met Asn Trp Tyr Gln Gln Lys Pro Gly Lys Ala Pro
            35                  40                  45

Lys Leu Leu Ile Tyr Ala Ala Ser Asn Leu Glu Ser Gly Ile Pro Ser
        50                  55                  60

```
Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ser Asn
                 85                  90                  95

Glu Asp Pro Phe Thr Phe Gly Pro Gly Thr Lys Val Asp Ile Lys Arg
            100                 105                 110

Thr

<210> SEQ ID NO 16
<211> LENGTH: 115
<212> TYPE: PRT
<213> ORGANISM: Artificial Sequence
<220> FEATURE:
<223> OTHER INFORMATION: Humanized heavy chain proten HZD_H1

<400> SEQUENCE: 16

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
                 20                  25                  30

Tyr Met His Trp Val Arg Gln Ala Pro Gly Gln Leu Glu Trp Met Gly
             35                  40                  45

Trp Ile Tyr Pro Gly Asn Val Asn Thr Tyr Tyr Asn Glu Lys Phe Arg
     50                  55                  60

Gly Arg Val Thr Ile Thr Ala Asp Thr Ser Ala Ser Thr Ala Tyr Met
 65                  70                  75                  80

Leu Ser Ser Leu Arg Ser Glu Asp Thr Ala Val Tyr Tyr Cys Ala Ser
                 85                  90                  95

Glu Glu Lys Asn Tyr Pro Trp Phe Ala Tyr Trp Gly Gln Gly Thr Leu
            100                 105                 110

Val Thr Ser
        115

<210> SEQ ID NO 17
<211> LENGTH: 115
<212> TYPE: PRT
<213> ORGANISM: Artificial Sequence
<220> FEATURE:
<223> OTHER INFORMATION: Humanized heavy chain protein HZD_H2

<400> SEQUENCE: 17

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
                 20                  25                  30

Tyr Met His Trp Val Arg Gln Ala Pro Gly Gln Leu Glu Trp Ile Gly
             35                  40                  45

Trp Ile Tyr Pro Gly Asn Val Asn Thr Tyr Tyr Asn Glu Lys Phe Arg
     50                  55                  60

Gly Arg Ala Thr Leu Thr Ala Asp Lys Ser Ala Ser Thr Ala Tyr Met
 65                  70                  75                  80

Leu Ser Ser Leu Arg Ser Glu Asp Thr Ala Val Tyr Tyr Cys Ala Ser
                 85                  90                  95

Glu Glu Lys Asn Tyr Pro Trp Phe Ala Tyr Trp Gly Gln Gly Thr Leu
            100                 105                 110

Val Thr Ser
        115
```

<210> SEQ ID NO 18
<211> LENGTH: 115
<212> TYPE: PRT
<213> ORGANISM: Artificial Sequence
<220> FEATURE:
<223> OTHER INFORMATION: Humanized heavy chain protein HZD_H3

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met His Trp Val Arg Gln Ala Pro Gly Gln Leu Glu Trp Ile Gly
            35                  40                  45

Trp Ile Tyr Pro Gly Asn Val Asn Thr Tyr Tyr Asn Glu Lys Phe Arg
        50                  55                  60

Gly Arg Ala Thr Ile Thr Ala Asp Thr Ser Ala Ser Thr Ala Tyr Met
65                  70                  75                  80

Leu Ser Ser Leu Arg Ser Glu Asp Thr Ala Val Tyr Tyr Cys Ala Ser
                85                  90                  95

Glu Glu Lys Asn Tyr Pro Trp Phe Ala Tyr Trp Gly Gln Gly Thr Leu
            100                 105                 110

Val Thr Ser
        115

<210> SEQ ID NO 19
<211> LENGTH: 115
<212> TYPE: PRT
<213> ORGANISM: Artificial Sequence
<220> FEATURE:
<223> OTHER INFORMATION: Humanized heavy chain protein HZD_H4

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met His Trp Val Arg Gln Ala Pro Gly Gln Leu Glu Trp Ile Gly
            35                  40                  45

Trp Ile Tyr Pro Gly Asn Val Asn Thr Tyr Tyr Asn Glu Lys Phe Arg
        50                  55                  60

Gly Lys Ala Thr Leu Thr Ala Asp Lys Ser Ala Ser Thr Ala Tyr Met
65                  70                  75                  80

Leu Ser Ser Leu Arg Ser Glu Asp Thr Ala Val Tyr Tyr Cys Ala Ser
                85                  90                  95

Glu Glu Lys Asn Tyr Pro Trp Phe Ala Tyr Trp Gly Gln Gly Thr Leu
            100                 105                 110

Val Thr Ser
        115

<210> SEQ ID NO 20
<211> LENGTH: 115
<212> TYPE: PRT
<213> ORGANISM: Artificial Sequence
<220> FEATURE:
<223> OTHER INFORMATION: Humanized heavy chain protein HZD_H5

<400> SEQUENCE: 20

Gln Val Gln Leu Val Gln Ser Gly Ala Glu Val Lys Lys Pro Gly Ala

```
               1               5                  10                 15
            Ser Val Lys Val Ser Cys Lys Ala Ser Gly Tyr Thr Phe Thr Asn Tyr
                        20                 25                 30

Tyr Met His Trp Val Lys Gln Arg Pro Gly Gln Leu Glu Trp Ile Gly
                        35                 40                 45

Trp Ile Tyr Pro Gly Asn Val Asn Thr Tyr Tyr Asn Glu Lys Phe Arg
                        50                 55                 60

Gly Lys Ala Thr Leu Thr Ala Asp Lys Ser Ala Ser Thr Ala Tyr Met
             65                 70                 75                 80

Leu Ser Ser Leu Arg Ser Glu Asp Thr Ala Val Tyr Tyr Cys Ala Ser
                        85                 90                 95

Glu Glu Lys Asn Tyr Pro Trp Phe Ala Tyr Trp Gly Gln Gly Thr Leu
                        100                105                110

Val Thr Ser
                        115

<210> SEQ ID NO 21
<211> LENGTH: 115
<212> TYPE: PRT
<213> ORGANISM: Artificial Sequence
<220> FEATURE:
<223> OTHER INFORMATION: Humanized heavy chain protein HZD_H6

<400> SEQUENCE: 21

Gln Val Gln Leu Val Gln Ser Gly Ala Glu Val Lys Lys Pro Gly Ala
             1               5                  10                 15

Ser Val Lys Val Ser Cys Lys Ala Ser Gly Tyr Thr Phe Thr Asn Tyr
                        20                 25                 30

Tyr Met His Trp Val Arg Gln Arg Pro Gly Gln Leu Glu Trp Ile Gly
                        35                 40                 45

Trp Ile Tyr Pro Gly Asn Val Asn Thr Tyr Tyr Asn Glu Lys Phe Arg
                        50                 55                 60

Gly Lys Ala Thr Ile Thr Ala Asp Lys Ser Ala Ser Thr Ala Tyr Met
             65                 70                 75                 80

Leu Ser Ser Leu Arg Ser Glu Asp Thr Ala Val Tyr Tyr Cys Ala Ser
                        85                 90                 95

Glu Glu Lys Asn Tyr Pro Trp Phe Ala Tyr Trp Gly Gln Gly Thr Leu
                        100                105                110

Val Thr Ser
                        115

<210> SEQ ID NO 22
<211> LENGTH: 117
<212> TYPE: PRT
<213> ORGANISM: Artificial Sequence
<220> FEATURE:
<223> OTHER INFORMATION: Humanized heavy chain protein HZD_H7

<400> SEQUENCE: 22

Gln Val Gln Leu Val Gln Ser Gly Ala Glu Val Lys Lys Pro Gly Ala
             1               5                  10                 15

Ser Val Lys Val Ser Cys Lys Ala Ser Gly Tyr Thr Phe Thr Asn Tyr
                        20                 25                 30

Tyr Met His Trp Val Arg Gln Ala Pro Gly Gln Gly Leu Glu Trp Ile
                        35                 40                 45

Gly Trp Ile Tyr Pro Gly Asn Val Asn Thr Tyr Tyr Asn Glu Lys Phe
                        50                 55                 60
```

```
Arg Gly Lys Ala Thr Ile Thr Ala Asp Thr Ser Ala Ser Thr Ala Tyr
 65                  70                  75                  80

Met Glu Leu Ser Ser Leu Arg Ser Glu Asp Thr Ala Val Tyr Phe Cys
                 85                  90                  95

Ala Ser Glu Glu Lys Asn Tyr Pro Trp Phe Ala Tyr Trp Gly Gln Gly
            100                 105                 110

Thr Leu Val Thr Ser
            115

<210> SEQ ID NO 23
<211> LENGTH: 121
<212> TYPE: PRT
<213> ORGANISM: Artificial Sequence
<220> FEATURE:
<223> OTHER INFORMATION: Humanized heavy chain protein H1

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met His Trp Val Arg Gln Arg Pro Gly Gln Gly Leu Glu Trp Ile
            35                  40                  45

Gly Trp Ile Tyr Pro Gly Asn Val Asn Thr Tyr Tyr Asn Glu Lys Phe
        50                  55                  60

Arg Gly Lys Ala Thr Ile Thr Ala Asp Lys Ser Ala Ser Thr Ala Tyr
 65                  70                  75                  80

Met Glu Leu Ser Ser Leu Arg Ser Glu Asp Thr Ala Val Tyr Phe Cys
                 85                  90                  95

Ala Ser Glu Glu Lys Asn Tyr Pro Trp Phe Ala Tyr Trp Gly Gln Gly
            100                 105                 110

Thr Leu Val Thr Val Ser Ser Ala Ser
            115                 120

<210> SEQ ID NO 24
<211> LENGTH: 121
<212> TYPE: PRT
<213> ORGANISM: Artificial Sequence
<220> FEATURE:
<223> OTHER INFORMATION: Humanized heavy chain protein H2

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met His Trp Val Arg Gln Ala Pro Gly Gln Gly Leu Glu Trp Ile
            35                  40                  45

Gly Trp Ile Tyr Pro Gly Asn Val Asn Thr Tyr Tyr Asn Glu Lys Phe
        50                  55                  60

Arg Gly Lys Ala Thr Ile Thr Ala Asp Thr Ser Ala Ser Thr Ala Tyr
 65                  70                  75                  80

Met Glu Leu Ser Ser Leu Arg Ser Glu Asp Thr Ala Val Tyr Phe Cys
                 85                  90                  95

Ala Ser Glu Glu Lys Asn Tyr Pro Trp Phe Ala Tyr Trp Gly Gln Gly
            100                 105                 110

Thr Leu Val Thr Val Ser Ser Ala Ser
            115                 120
```

```
<210> SEQ ID NO 25
<211> LENGTH: 121
<212> TYPE: PRT
<213> ORGANISM: Artificial Sequence
<220> FEATURE:
<223> OTHER INFORMATION: Humanized heavy chain protein H3

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Ile
        35                  40                  45

Gly Trp Ile Tyr Pro Gly Asn Val Asn Thr Tyr Tyr Asn Glu Lys Phe
    50                  55                  60

Arg Gly Lys Ala Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Ser Glu Glu Lys Asn Tyr Pro Trp Phe Ala Tyr Trp Gly Gln Gly
            100                 105                 110

Thr Leu Val Thr Val Ser Ser Ala Ser
        115                 120

<210> SEQ ID NO 26
<211> LENGTH: 15
<212> TYPE: PRT
<213> ORGANISM: Artificial Sequence
<220> FEATURE:
<223> OTHER INFORMATION: Important light chain domain sequence

<400> SEQUENCE: 26

Gln Ser Pro Ser Ser Leu Ser Ala Ser Val Gly Asp Arg Val Thr
1               5                   10                  15

<210> SEQ ID NO 27
<211> LENGTH: 20
<212> TYPE: PRT
<213> ORGANISM: Artificial Sequence
<220> FEATURE:
<223> OTHER INFORMATION: Important light chain domain sequence

<400> SEQUENCE: 27

Lys Ala Ser Gln Ser Val Glu Asp Asp Gly Glu Asn Tyr Met Asn Trp
1               5                   10                  15

Tyr Gln Gln Lys
        20

<210> SEQ ID NO 28
<211> LENGTH: 35
<212> TYPE: PRT
<213> ORGANISM: Artificial Sequence
<220> FEATURE:
<223> OTHER INFORMATION: Important light chain domain sequence

<400> SEQUENCE: 28

Ser Gly Ser Gly Ser Gly Thr Asp Phe Thr Leu Thr Ile Ser Ser Leu
1               5                   10                  15

Gln Pro Glu Asp Phe Ala Thr Tyr Tyr Cys Gln Gln Ser Asn Glu Asp
            20                  25                  30
```

Pro Phe Thr
        35

<210> SEQ ID NO 29
<211> LENGTH: 33
<212> TYPE: PRT
<213> ORGANISM: Artificial Sequence
<220> FEATURE:
<223> OTHER INFORMATION: Important heavy chain domain sequence

<400> SEQUENCE: 29

Val Gln Ser Gly Ala Glu Val Lys Lys Pro Gly Ala Ser Val Lys Val
1               5                   10                  15

Ser Cys Lys Ala Ser Gly Tyr Thr Phe Thr Asn Tyr Tyr Met His Trp
            20                  25                  30

Val

<210> SEQ ID NO 30
<211> LENGTH: 16
<212> TYPE: PRT
<213> ORGANISM: Artificial Sequence
<220> FEATURE:
<223> OTHER INFORMATION: Important heavy chain domain sequence

<400> SEQUENCE: 30

Trp Ile Tyr Pro Gly Asn Val Asn Thr Tyr Tyr Asn Glu Lys Phe Arg
1               5                   10                  15

<210> SEQ ID NO 31
<211> LENGTH: 14
<212> TYPE: PRT
<213> ORGANISM: Artificial Sequence
<220> FEATURE:
<223> OTHER INFORMATION: Important heavy chain domain sequence

<400> SEQUENCE: 31

Ala Ser Thr Ala Tyr Met Glu Leu Ser Ser Leu Arg Ser Glu
1               5                   10

<210> SEQ ID NO 32
<211> LENGTH: 20
<212> TYPE: PRT
<213> ORGANISM: Artificial Sequence
<220> FEATURE:
<223> OTHER INFORMATION: Important heavy chain domain sequence

<400> SEQUENCE: 32

Ala Ser Glu Glu Lys Asn Tyr Pro Trp Phe Ala Tyr Trp Gly Gln Gly
1               5                   10                  15

Thr Leu Val Thr
        20

<210> SEQ ID NO 33
<211> LENGTH: 157
<212> TYPE: PRT
<213> ORGANISM: Artificial Sequence
<220> FEATURE:
<223> OTHER INFORMATION: Monoclonal antibody 223 heavy chain variable
      region

<400> SEQUENCE: 33

Glu Phe Met Glu Trp Ser Trp Val Ile Leu Phe Leu Leu Ser Ile Ile
1               5                   10                  15

Ala Gly Val His Cys Gln Val Gln Leu Gln Gln Ser Gly Pro Glu Leu

```
                20                  25                  30
Val Lys Pro Gly Ala Ser Val Arg Ile Ser Cys Lys Ala Ser Gly Tyr
            35                  40                  45

Thr Phe Thr Ser Tyr Tyr Ile His Trp Val Lys Gln Arg Pro Gly Gln
    50                  55                  60

Gly Leu Glu Trp Ile Gly Trp Ile Tyr Pro Gly Asn Val Asn Thr Glu
65                  70                  75                  80

Tyr Asn Glu Lys Phe Arg Gly Lys Ala Thr Leu Thr Ala Asp Lys Ser
                85                  90                  95

Ser Ser Thr Ala Tyr Met Gln Leu Ser Ser Leu Thr Ser Glu Asp Ser
            100                 105                 110

Ala Val Tyr Phe Cys Ala Ser Glu Glu Arg Asn Tyr Pro Trp Phe Ala
        115                 120                 125

Tyr Trp Gly Gln Gly Thr Leu Val Thr Val Ser Ala Ala Lys Thr Thr
    130                 135                 140

Pro Pro Pro Val Tyr Pro Leu Val Pro Gly Ser Leu Gly
145                 150                 155

<210> SEQ ID NO 34
<211> LENGTH: 152
<212> TYPE: PRT
<213> ORGANISM: Artificial Sequence
<220> FEATURE:
<223> OTHER INFORMATION: Monoclonal antibody 223 light chain variable
      region

<400> SEQUENCE: 34

Trp Glu Phe Met Glu Thr Asp Thr Leu Leu Leu Trp Val Leu Leu Leu
1               5                   10                  15

Trp Val Pro Gly Ser Thr Gly Asp Ile Val Leu Thr Gln Ser Pro Ala
            20                  25                  30

Ser Leu Ala Val Ser Leu Gly Gln Arg Ala Thr Ile Ser Cys Lys Ala
        35                  40                  45

Ser Gln Ser Val Glu Asp Asp Gly Glu Asn Tyr Met Asn Trp Tyr Gln
    50                  55                  60

Gln Lys Pro Gly Gln Ser Pro Lys Leu Leu Ile Tyr Ala Ala Ser Asn
65                  70                  75                  80

Leu Glu Ser Gly Ile Pro Ala Arg Phe Ser Gly Ser Gly Ser Gly Thr
                85                  90                  95

Asp Phe Thr Leu Asn Ile His Pro Val Glu Glu Glu Asp Ala Ala Thr
            100                 105                 110

Tyr Tyr Cys Gln Gln Ser Asn Glu Asp Pro Phe Thr Phe Gly Ser Gly
        115                 120                 125

Thr Lys Leu Glu Ile Lys Arg Ala Asp Ala Ala Pro Thr Val Ser Ile
    130                 135                 140

Phe Pro Pro Ser Ser Lys Leu Gly
145                 150

<210> SEQ ID NO 35
<211> LENGTH: 154
<212> TYPE: PRT
<213> ORGANISM: Artificial Sequence
<220> FEATURE:
<223> OTHER INFORMATION: Monoclonal antibody 318 heavy chain variable
      region

<400> SEQUENCE: 35

Glu Phe Met Glu Trp Ser Trp Val Phe Leu Phe Leu Leu Ser Ile Ile
```

```
                1               5                    10                   15
        Ala Gly Val His Cys Gln Val Gln Leu Gln Gln Ser Gly Pro Glu Leu
                        20                  25                  30
        Val Lys Pro Gly Ala Ser Val Arg Ile Ser Cys Lys Ala Ser Gly Tyr
                        35                  40                  45
        Thr Phe Thr Asn Tyr Tyr Met His Trp Val Lys Gln Arg Pro Gly Gln
                        50                  55                  60
        Gly Leu Glu Trp Ile Gly Trp Ile Tyr Pro Gly Asn Val Asn Thr Tyr
         65                 70                  75                  80
        Tyr Asn Glu Lys Phe Arg Ala Arg Pro His Leu Gln Thr Asn Pro Pro
                        85                  90                  95
        Ala Gln Pro Thr Cys Ser Ser Ala Ala Pro Leu Arg Thr Leu Arg Ser
                        100                 105                 110
        Ile Ser Val Gln Val Arg Arg Glu Leu Pro Leu Val Cys Leu Leu Gly
                        115                 120                 125
        Pro Arg Asp Ser Gly His Cys Leu Cys Ser Gln Asn Asp Thr Pro Ile
                        130                 135                 140
        Arg Leu Ser Pro Gly Pro Trp Lys Leu Gly
        145                 150

<210> SEQ ID NO 36
<211> LENGTH: 131
<212> TYPE: PRT
<213> ORGANISM: Artificial Sequence
<220> FEATURE:
<223> OTHER INFORMATION: Monoclonal antibody 318 light chain variable
      region

<400> SEQUENCE: 36

Leu Val Asp Met Glu Ser Asp Thr Leu Leu Trp Val Leu Leu Leu
         1                 5                  10                  15
        Trp Val Pro Gly Ser Thr Gly Asp Ile Val Leu Thr Gln Ser Pro Ala
                        20                  25                  30
        Ser Leu Ala Val Ser Leu Gly Gln Arg Ala Thr Ile Ser Tyr Arg Ala
                        35                  40                  45
        Ser Lys Ser Val Ser Thr Ser Gly Tyr Ser Tyr Met His Trp Asn Gln
                        50                  55                  60
        Gln Lys Pro Gly Gln Pro Pro Arg Leu Leu Ile Tyr Leu Val Ser Asn
         65                 70                  75                  80
        Leu Glu Ser Gly Val Pro Ala Arg Phe Ser Gly Ser Gly Ser Gly Thr
                        85                  90                  95
        Asp Phe Thr Leu Asn Ile His Pro Val Glu Glu Glu Asp Ala Ala Thr
                        100                 105                 110
        Tyr Tyr Cys Gln His Ile Arg Glu Leu Thr Arg Ser Glu Gly Gly Pro
                        115                 120                 125
        Ser Trp Lys
            130

<210> SEQ ID NO 37
<211> LENGTH: 173
<212> TYPE: PRT
<213> ORGANISM: Artificial Sequence
<220> FEATURE:
<223> OTHER INFORMATION: Human PRL3 sequence

<400> SEQUENCE: 37

Met Ala Arg Met Asn Arg Pro Ala Pro Val Glu Val Ser Tyr Lys His
         1                 5                  10                  15
```

```
Met Arg Phe Leu Ile Thr His Asn Pro Thr Asn Ala Thr Leu Ser Thr
             20                  25                  30

Phe Ile Glu Asp Leu Lys Lys Tyr Gly Ala Thr Thr Val Arg Val
         35                  40                  45

Cys Glu Val Thr Tyr Asp Lys Thr Pro Leu Glu Lys Asp Gly Ile Thr
 50                  55                  60

Val Val Asp Trp Pro Phe Asp Asp Gly Ala Pro Pro Gly Lys Val
 65              70                  75                  80

Val Glu Asp Trp Leu Ser Leu Val Lys Ala Lys Phe Cys Glu Ala Pro
                 85                  90                  95

Gly Ser Cys Val Ala Val His Cys Val Ala Gly Leu Gly Arg Ala Pro
             100                 105                 110

Val Leu Val Ala Leu Ala Leu Ile Glu Ser Gly Met Lys Tyr Glu Asp
             115                 120                 125

Ala Ile Gln Phe Ile Arg Gln Lys Arg Gly Ala Ile Asn Ser Lys
 130                 135                 140

Gln Leu Thr Tyr Leu Glu Lys Tyr Arg Pro Lys Gln Arg Leu Arg Phe
145                 150                 155                 160

Lys Asp Pro His Thr His Lys Thr Arg Cys Cys Val Met
                 165                 170

<210> SEQ ID NO 38
<211> LENGTH: 6
<212> TYPE: PRT
<213> ORGANISM: Artificial Sequence
<220> FEATURE:
<223> OTHER INFORMATION: binding sequence

<400> SEQUENCE: 38

Lys Ala Lys Phe Tyr Asn
1               5

<210> SEQ ID NO 39
<211> LENGTH: 6
<212> TYPE: PRT
<213> ORGANISM: Artificial Sequence
<220> FEATURE:
<223> OTHER INFORMATION: binding sequence

<400> SEQUENCE: 39

His Thr His Lys Thr Arg
1               5

<210> SEQ ID NO 40
<211> LENGTH: 58
<212> TYPE: PRT
<213> ORGANISM: Artificial Sequence
<220> FEATURE:
<223> OTHER INFORMATION: synthetic polypeptide

<400> SEQUENCE: 40

Asp Thr Gln Leu Thr Gln Ser Pro Ser Ser Leu Ser Ala Ser Val Gly
1               5                   10                  15

Asp Arg Val Thr Ile Cys Lys Ala Ser Gln Ser Val Glu Asp Asp Gly
             20                  25                  30

Glu Asn Tyr Met Asn Trp Tyr Gln Gln Lys Pro Gly Ser Pro Lys Leu
             35                  40                  45

Leu Ile Tyr Ala Ala Ser Asn Leu Glu Ser
             50                  55
```

<210> SEQ ID NO 41
<211> LENGTH: 58
<212> TYPE: PRT
<213> ORGANISM: Artificial Sequence
<220> FEATURE:
<223> OTHER INFORMATION: synthetic polypeptide

<400> SEQUENCE: 41

```
Asp Thr Gln Leu Thr Gln Ser Pro Ser Ser Leu Ser Ala Ser Val Gly
1               5                   10                  15

Asp Arg Val Thr Ile Cys Lys Ala Ser Gln Ser Val Glu Asp Asp Gly
                20                  25                  30

Glu Asn Tyr Met Asn Trp Tyr Gln Gln Lys Pro Gly Ser Pro Lys Leu
            35                  40                  45

Leu Ile Tyr Ala Ala Ser Asn Leu Glu Ser
        50                  55
```

<210> SEQ ID NO 42
<211> LENGTH: 58
<212> TYPE: PRT
<213> ORGANISM: Artificial Sequence
<220> FEATURE:
<223> OTHER INFORMATION: synthetic polypeptide

<400> SEQUENCE: 42

```
Asp Thr Gln Leu Thr Gln Ser Pro Ser Ser Leu Ser Ala Ser Val Gly
1               5                   10                  15

Asp Arg Val Thr Ile Cys Lys Ala Ser Gln Ser Val Glu Asp Asp Gly
                20                  25                  30

Glu Asn Tyr Met Asn Trp Tyr Gln Gln Lys Pro Gly Ser Pro Lys Leu
            35                  40                  45

Leu Ile Tyr Ala Ala Ser Asn Leu Glu Ser
        50                  55
```

<210> SEQ ID NO 43
<211> LENGTH: 58
<212> TYPE: PRT
<213> ORGANISM: Artificial Sequence
<220> FEATURE:
<223> OTHER INFORMATION: synthetic polypeptide

<400> SEQUENCE: 43

```
Asp Thr Gln Leu Thr Gln Ser Pro Ser Ser Leu Ser Ala Ser Val Gly
1               5                   10                  15

Asp Arg Val Thr Ile Cys Lys Ala Ser Gln Ser Val Glu Asp Asp Gly
                20                  25                  30

Glu Asn Tyr Met Asn Trp Tyr Gln Gln Lys Pro Gly Ser Pro Lys Leu
            35                  40                  45

Leu Ile Tyr Ala Ala Ser Asn Leu Glu Ser
        50                  55
```

<210> SEQ ID NO 44
<211> LENGTH: 58
<212> TYPE: PRT
<213> ORGANISM: Artificial Sequence
<220> FEATURE:
<223> OTHER INFORMATION: synthetic polypeptide

<400> SEQUENCE: 44

```
Asp Thr Gln Leu Thr Gln Ser Pro Ser Ser Leu Ser Ala Ser Val Gly
1               5                   10                  15
```

```
Asp Arg Val Thr Ile Cys Lys Ala Ser Gln Ser Val Glu Asp Gly
            20                  25                  30

Glu Asn Tyr Met Asn Trp Tyr Gln Gln Lys Pro Gly Ser Pro Lys Leu
        35                  40                  45

Leu Ile Tyr Ala Ala Ser Asn Leu Glu Ser
    50                  55

<210> SEQ ID NO 45
<211> LENGTH: 58
<212> TYPE: PRT
<213> ORGANISM: Artificial Sequence
<220> FEATURE:
<223> OTHER INFORMATION: synthetic polypeptide

<400> SEQUENCE: 45

Asp Thr Val Leu Thr Gln Ser Pro Ser Ser Leu Ser Ala Ser Val Gly
1               5                   10                  15

Asp Arg Val Thr Ile Cys Lys Ala Ser Gln Ser Val Glu Asp Asp Gly
            20                  25                  30

Glu Asn Tyr Met Asn Trp Tyr Gln Gln Lys Pro Gly Ser Pro Lys Leu
        35                  40                  45

Leu Ile Tyr Ala Ala Ser Asn Leu Glu Ser
    50                  55

<210> SEQ ID NO 46
<211> LENGTH: 60
<212> TYPE: PRT
<213> ORGANISM: Artificial Sequence
<220> FEATURE:
<223> OTHER INFORMATION: synthetic polypeptide

<400> SEQUENCE: 46

Asp Ile Gln Met Thr Gln Ser Pro Ser Ser Leu Ser Ala Ser Val Gly
1               5                   10                  15

Asp Arg Val Thr Ile Ser Cys Lys Ala Ser Gln Ser Val Glu Asp Asp
            20                  25                  30

Gly Glu Asn Tyr Met Asn Trp Tyr Gln Gln Lys Pro Gly Lys Ser Pro
        35                  40                  45

Lys Leu Leu Ile Tyr Ala Ala Ser Asn Leu Glu Ser
    50                  55                  60

<210> SEQ ID NO 47
<211> LENGTH: 60
<212> TYPE: PRT
<213> ORGANISM: Artificial Sequence
<220> FEATURE:
<223> OTHER INFORMATION: synthetic polypeptide

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Glu Asp Asp
            20                  25                  30

Gly Glu Asn Tyr Met Asn Trp Tyr Gln Gln Lys Pro Gly Lys Ala Pro
        35                  40                  45

Lys Leu Leu Ile Tyr Ala Ala Ser Asn Leu Glu Ser
    50                  55                  60

<210> SEQ ID NO 48
<211> LENGTH: 60
<212> TYPE: PRT
```

```
<213> ORGANISM: Artificial Sequence
<220> FEATURE:
<223> OTHER INFORMATION: synthetic polypeptide

<400> SEQUENCE: 48

Asp Thr Gln Leu Thr Gln Ser Pro Ser Leu Ser Ala Ser Val Gly
1               5                  10                  15

Asp Arg Val Thr Ile Thr Cys Lys Ala Ser Gln Ser Val Glu Asp Asp
            20                  25                  30

Gly Glu Asn Tyr Met Asn Trp Tyr Gln Gln Lys Pro Gly Lys Ala Pro
        35                  40                  45

Lys Leu Leu Ile Tyr Ala Ala Ser Asn Leu Glu Ser
    50                  55                  60

<210> SEQ ID NO 49
<211> LENGTH: 50
<212> TYPE: PRT
<213> ORGANISM: Artificial Sequence
<220> FEATURE:
<223> OTHER INFORMATION: synthetic polypeptide

<400> SEQUENCE: 49

Gly Ile Pro Ala Arg Phe Ser Gly Ser Gly Ser Gly Thr Asp Phe Thr
1               5                  10                  15

Leu Thr Ile Ser Ser Leu Pro Glu Asp Phe Ala Thr Tyr Tyr Cys Gln
            20                  25                  30

Gln Ser Asn Glu Asp Pro Phe Thr Phe Gly Ser Gly Thr Lys Leu Glu
        35                  40                  45

Ile Lys
    50

<210> SEQ ID NO 50
<211> LENGTH: 50
<212> TYPE: PRT
<213> ORGANISM: Artificial Sequence
<220> FEATURE:
<223> OTHER INFORMATION: synthetic polypeptide

<400> SEQUENCE: 50

Gly Ile Pro Ala Arg Phe Ser Gly Ser Gly Ser Gly Thr Asp Phe Thr
1               5                  10                  15

Leu Thr Ile Ser Ser Leu Pro Glu Asp Phe Ala Thr Tyr Tyr Cys Gln
            20                  25                  30

Gln Ser Asn Glu Asp Pro Phe Thr Phe Gly Gln Gly Thr Lys Leu Glu
        35                  40                  45

Ile Lys
    50

<210> SEQ ID NO 51
<211> LENGTH: 50
<212> TYPE: PRT
<213> ORGANISM: Artificial Sequence
<220> FEATURE:
<223> OTHER INFORMATION: synthetic polypeptide

<400> SEQUENCE: 51

Gly Val Pro Ser Arg Phe Ser Gly Ser Gly Ser Gly Thr Asp Phe Thr
1               5                  10                  15

Leu Thr Ile Ser Ser Leu Pro Glu Asp Phe Ala Thr Tyr Tyr Cys Gln
            20                  25                  30

Gln Ser Asn Glu Asp Pro Phe Thr Phe Gly Gln Gly Thr Lys Leu Glu
```

<210> SEQ ID NO 52
<211> LENGTH: 50
<212> TYPE: PRT
<213> ORGANISM: Artificial Sequence
<220> FEATURE:
<223> OTHER INFORMATION: synthetic polypeptide

<400> SEQUENCE: 52

Gly Ile Pro Ser Arg Phe Ser Gly Ser Gly Ser Gly Thr Asp Phe Thr
1               5                   10                  15

Leu Thr Ile Ser Ser Leu Pro Glu Asp Phe Ala Thr Tyr Tyr Cys Gln
            20                  25                  30

Gln Ser Asn Glu Asp Pro Phe Thr Phe Gly Pro Gly Thr Lys Val Asp
        35                  40                  45

Ile Lys
    50

<210> SEQ ID NO 53
<211> LENGTH: 50
<212> TYPE: PRT
<213> ORGANISM: Artificial Sequence
<220> FEATURE:
<223> OTHER INFORMATION: synthetic polypeptide

<400> SEQUENCE: 53

Gly Ile Pro Ser Arg Phe Ser Gly Ser Gly Ser Gly Thr Asp Phe Thr
1               5                   10                  15

Leu Thr Ile Ser Ser Leu Pro Glu Asp Phe Ala Thr Tyr Tyr Cys Gln
            20                  25                  30

Gln Ser Asn Glu Asp Pro Phe Thr Phe Gly Pro Gly Thr Lys Val Asp
        35                  40                  45

Ile Lys
    50

<210> SEQ ID NO 54
<211> LENGTH: 50
<212> TYPE: PRT
<213> ORGANISM: Artificial Sequence
<220> FEATURE:
<223> OTHER INFORMATION: synthetic polypeptide

<400> SEQUENCE: 54

Gly Ile Pro Ser Arg Phe Ser Gly Ser Gly Ser Gly Thr Asp Phe Thr
1               5                   10                  15

Leu Thr Ile Ser Ser Leu Pro Glu Asp Phe Ala Thr Tyr Tyr Cys Gln
            20                  25                  30

Gln Ser Asn Glu Asp Pro Phe Thr Phe Gly Pro Gly Thr Lys Val Asp
        35                  40                  45

Ile Lys
    50

<210> SEQ ID NO 55
<211> LENGTH: 53
<212> TYPE: PRT
<213> ORGANISM: Artificial Sequence
<220> FEATURE:
<223> OTHER INFORMATION: synthetic polypeptide

```
<400> SEQUENCE: 55

Gly Ile Pro Ala Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

Gln Gln Ser Asn Glu Asp Pro Phe Thr Phe Gly Ser Gly Thr Lys Leu
        35                  40                  45

Glu Ile Lys Arg Thr
    50

<210> SEQ ID NO 56
<211> LENGTH: 53
<212> TYPE: PRT
<213> ORGANISM: Artificial Sequence
<220> FEATURE:
<223> OTHER INFORMATION: synthetic polypeptide

<400> SEQUENCE: 56

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

Gln Gln Ser Asn Glu Asp Pro Phe Thr Phe Gly Pro Gly Thr Lys Val
        35                  40                  45

Asp Ile Lys Arg Thr
    50

<210> SEQ ID NO 57
<211> LENGTH: 53
<212> TYPE: PRT
<213> ORGANISM: Artificial Sequence
<220> FEATURE:
<223> OTHER INFORMATION: synthetic polypeptide

<400> SEQUENCE: 57

Gly Ile Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

Gln Gln Ser Asn Glu Asp Pro Phe Thr Phe Gly Pro Gly Thr Lys Val
        35                  40                  45

Asp Ile Lys Arg Thr
    50

<210> SEQ ID NO 58
<211> LENGTH: 59
<212> TYPE: PRT
<213> ORGANISM: Artificial Sequence
<220> FEATURE:
<223> OTHER INFORMATION: synthetic polypeptide

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Leu Glu Trp Met Gly
        35                  40                  45

Trp Ile Tyr Pro Gly Asn Val Asn Thr Tyr Tyr
    50                  55
```

<210> SEQ ID NO 59
<211> LENGTH: 59
<212> TYPE: PRT
<213> ORGANISM: Artificial Sequence
<220> FEATURE:
<223> OTHER INFORMATION: synthetic polypeptide

<400> SEQUENCE: 59

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Leu Glu Trp Ile Gly
        35                  40                  45

Trp Ile Tyr Pro Gly Asn Val Asn Thr Tyr Tyr
    50                  55

<210> SEQ ID NO 60
<211> LENGTH: 59
<212> TYPE: PRT
<213> ORGANISM: Artificial Sequence
<220> FEATURE:
<223> OTHER INFORMATION: synthetic polypeptide

<400> SEQUENCE: 60

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Leu Glu Trp Ile Gly
        35                  40                  45

Trp Ile Tyr Pro Gly Asn Val Asn Thr Tyr Tyr
    50                  55

<210> SEQ ID NO 61
<211> LENGTH: 59
<212> TYPE: PRT
<213> ORGANISM: Artificial Sequence
<220> FEATURE:
<223> OTHER INFORMATION: synthetic polypeptide

<400> SEQUENCE: 61

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Leu Glu Trp Ile Gly
        35                  40                  45

Trp Ile Tyr Pro Gly Asn Val Asn Thr Tyr Tyr
    50                  55

<210> SEQ ID NO 62
<211> LENGTH: 59
<212> TYPE: PRT
<213> ORGANISM: Artificial Sequence
<220> FEATURE:
<223> OTHER INFORMATION: synthetic polypeptide

<400> SEQUENCE: 62

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Lys Gln Arg Pro Gly Gln Leu Glu Trp Ile Gly
        35                  40                  45

Trp Ile Tyr Pro Gly Asn Val Asn Thr Tyr Tyr
    50                  55

<210> SEQ ID NO 63
<211> LENGTH: 59
<212> TYPE: PRT
<213> ORGANISM: Artificial Sequence
<220> FEATURE:
<223> OTHER INFORMATION: synthetic polypeptide

<400> SEQUENCE: 63

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Arg Pro Gly Gln Leu Glu Trp Ile Gly
        35                  40                  45

Trp Ile Tyr Pro Gly Asn Val Asn Thr Tyr Tyr
    50                  55

<210> SEQ ID NO 64
<211> LENGTH: 60
<212> TYPE: PRT
<213> ORGANISM: Artificial Sequence
<220> FEATURE:
<223> OTHER INFORMATION: synthetic polypeptide

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Ile
        35                  40                  45

Gly Trp Ile Tyr Pro Gly Asn Val Asn Thr Tyr Tyr
    50                  55                  60

<210> SEQ ID NO 65
<211> LENGTH: 60
<212> TYPE: PRT
<213> ORGANISM: Artificial Sequence
<220> FEATURE:
<223> OTHER INFORMATION: synthetic polypeptide

<400> SEQUENCE: 65

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Arg Pro Gly Gln Gly Leu Glu Trp Ile
        35                  40                  45

Gly Trp Ile Tyr Pro Gly Asn Val Asn Thr Tyr Tyr
    50                  55                  60

<210> SEQ ID NO 66
<211> LENGTH: 60

```
<212> TYPE: PRT
<213> ORGANISM: Artificial Sequence
<220> FEATURE:
<223> OTHER INFORMATION: synthetic polypeptide

<400> SEQUENCE: 66

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Ile
        35                  40                  45

Gly Trp Ile Tyr Pro Gly Asn Val Asn Thr Tyr Tyr
    50                  55                  60

<210> SEQ ID NO 67
<211> LENGTH: 60
<212> TYPE: PRT
<213> ORGANISM: Artificial Sequence
<220> FEATURE:
<223> OTHER INFORMATION: synthetic polypeptide

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Ile
        35                  40                  45

Gly Trp Ile Tyr Pro Gly Asn Val Asn Thr Tyr Tyr
    50                  55                  60

<210> SEQ ID NO 68
<211> LENGTH: 56
<212> TYPE: PRT
<213> ORGANISM: Artificial Sequence
<220> FEATURE:
<223> OTHER INFORMATION: synthetic polypeptide

<400> SEQUENCE: 68

Asn Glu Lys Phe Arg Gly Arg Val Thr Ile Thr Ala Asp Thr Ser Ala
1               5                   10                  15

Ser Thr Ala Tyr Met Leu Ser Ser Leu Arg Ser Glu Asp Thr Ala Val
            20                  25                  30

Tyr Tyr Cys Ala Ser Glu Glu Lys Asn Tyr Pro Trp Phe Ala Tyr Trp
        35                  40                  45

Gly Gln Gly Thr Leu Val Thr Ser
    50                  55

<210> SEQ ID NO 69
<211> LENGTH: 56
<212> TYPE: PRT
<213> ORGANISM: Artificial Sequence
<220> FEATURE:
<223> OTHER INFORMATION: synthetic polypeptide

<400> SEQUENCE: 69

Asn Glu Lys Phe Arg Gly Arg Ala Thr Leu Thr Ala Asp Lys Ser Ala
1               5                   10                  15

Ser Thr Ala Tyr Met Leu Ser Ser Leu Arg Ser Glu Asp Thr Ala Val
            20                  25                  30
```

Tyr Tyr Cys Ala Ser Glu Glu Lys Asn Tyr Pro Trp Phe Ala Tyr Trp
            35                  40                  45

Gly Gln Gly Thr Leu Val Thr Ser
        50                  55

<210> SEQ ID NO 70
<211> LENGTH: 56
<212> TYPE: PRT
<213> ORGANISM: Artificial Sequence
<220> FEATURE:
<223> OTHER INFORMATION: synthetic polypeptide

<400> SEQUENCE: 70

Asn Glu Lys Phe Arg Gly Arg Ala Thr Ile Thr Ala Asp Thr Ser Ala
1               5                   10                  15

Ser Thr Ala Tyr Met Leu Ser Ser Leu Arg Ser Glu Asp Thr Ala Val
            20                  25                  30

Tyr Tyr Cys Ala Ser Glu Glu Lys Asn Tyr Pro Trp Phe Ala Tyr Trp
            35                  40                  45

Gly Gln Gly Thr Leu Val Thr Ser
        50                  55

<210> SEQ ID NO 71
<211> LENGTH: 56
<212> TYPE: PRT
<213> ORGANISM: Artificial Sequence
<220> FEATURE:
<223> OTHER INFORMATION: synthetic polypeptide

<400> SEQUENCE: 71

Asn Glu Lys Phe Arg Gly Lys Ala Thr Leu Thr Ala Asp Lys Ser Ala
1               5                   10                  15

Ser Thr Ala Tyr Met Leu Ser Ser Leu Arg Ser Glu Asp Thr Ala Val
            20                  25                  30

Tyr Tyr Cys Ala Ser Glu Glu Lys Asn Tyr Pro Trp Phe Ala Tyr Trp
            35                  40                  45

Gly Gln Gly Thr Leu Val Thr Ser
        50                  55

<210> SEQ ID NO 72
<211> LENGTH: 56
<212> TYPE: PRT
<213> ORGANISM: Artificial Sequence
<220> FEATURE:
<223> OTHER INFORMATION: synthetic polypeptide

<400> SEQUENCE: 72

Asn Glu Lys Phe Arg Gly Lys Ala Thr Leu Thr Ala Asp Lys Ser Ala
1               5                   10                  15

Ser Thr Ala Tyr Met Leu Ser Ser Leu Arg Ser Glu Asp Thr Ala Val
            20                  25                  30

Tyr Tyr Cys Ala Ser Glu Glu Lys Asn Tyr Pro Trp Phe Ala Tyr Trp
            35                  40                  45

Gly Gln Gly Thr Leu Val Thr Ser
        50                  55

<210> SEQ ID NO 73
<211> LENGTH: 56
<212> TYPE: PRT
<213> ORGANISM: Artificial Sequence
<220> FEATURE:
<223> OTHER INFORMATION: synthetic polypeptide

<400> SEQUENCE: 73

Asn Glu Lys Phe Arg Gly Lys Ala Thr Ile Thr Ala Asp Lys Ser Ala
1               5                   10                  15

Ser Thr Ala Tyr Met Leu Ser Ser Leu Arg Ser Glu Asp Thr Ala Val
            20                  25                  30

Tyr Tyr Cys Ala Ser Glu Glu Lys Asn Tyr Pro Trp Phe Ala Tyr Trp
        35                  40                  45

Gly Gln Gly Thr Leu Val Thr Ser
    50                  55

<210> SEQ ID NO 74
<211> LENGTH: 57
<212> TYPE: PRT
<213> ORGANISM: Artificial Sequence
<220> FEATURE:
<223> OTHER INFORMATION: synthetic polypeptide

<400> SEQUENCE: 74

Asn Glu Lys Phe Arg Gly Lys Ala Thr Ile Thr Ala Asp Thr Ser Ala
1               5                   10                  15

Ser Thr Ala Tyr Met Glu Leu Ser Ser Leu Arg Ser Glu Asp Thr Ala
            20                  25                  30

Val Tyr Phe Cys Ala Ser Glu Glu Lys Asn Tyr Pro Trp Phe Ala Tyr
        35                  40                  45

Trp Gly Gln Gly Thr Leu Val Thr Ser
    50                  55

<210> SEQ ID NO 75
<211> LENGTH: 61
<212> TYPE: PRT
<213> ORGANISM: Artificial Sequence
<220> FEATURE:
<223> OTHER INFORMATION: synthetic polypeptide

<400> SEQUENCE: 75

Asn Glu Lys Phe Arg Gly Lys Ala Thr Ile Thr Ala Asp Lys Ser Ala
1               5                   10                  15

Ser Thr Ala Tyr Met Glu Leu Ser Ser Leu Arg Ser Glu Asp Thr Ala
            20                  25                  30

Val Tyr Phe Cys Ala Ser Glu Glu Lys Asn Tyr Pro Trp Phe Ala Tyr
        35                  40                  45

Trp Gly Gln Gly Thr Leu Val Thr Val Ser Ser Ala Ser
    50                  55                  60

<210> SEQ ID NO 76
<211> LENGTH: 61
<212> TYPE: PRT
<213> ORGANISM: Artificial Sequence
<220> FEATURE:
<223> OTHER INFORMATION: synthetic polypeptide

<400> SEQUENCE: 76

Asn Glu Lys Phe Arg Gly Lys Ala Thr Ile Thr Ala Asp Thr Ser Ala
1               5                   10                  15

Ser Thr Ala Tyr Met Glu Leu Ser Ser Leu Arg Ser Glu Asp Thr Ala
            20                  25                  30

Val Tyr Phe Cys Ala Ser Glu Glu Lys Asn Tyr Pro Trp Phe Ala Tyr
        35                  40                  45

Trp Gly Gln Gly Thr Leu Val Thr Val Ser Ser Ala Ser

```
<210> SEQ ID NO 77
<211> LENGTH: 61
<212> TYPE: PRT
<213> ORGANISM: Artificial Sequence
<220> FEATURE:
<223> OTHER INFORMATION: synthetic polypeptide

<400> SEQUENCE: 77

Asn Glu Lys Phe Arg Gly Lys Ala Thr Leu Thr Ala Asp Lys Ser Ala
1               5                  10                  15

Ser Thr Ala Tyr Met Glu Leu Ser Ser Leu Arg Ser Glu Asp Thr Ala
            20                  25                  30

Val Tyr Phe Cys Ala Ser Glu Glu Lys Asn Tyr Pro Trp Phe Ala Tyr
        35                  40                  45

Trp Gly Gln Gly Thr Leu Val Thr Val Ser Ser Ala Ser
    50                  55                  60
```